(12) United States Patent
Andersson et al.

(10) Patent No.: US 6,630,600 B1
(45) Date of Patent: Oct. 7, 2003

(54) 3-ARYL PROPIONIC ACID DERIVATIVES AND ANALOGS

(75) Inventors: Kjell Andersson, Fjärås (SE); Maria Boije, Torslanda (SE); Johan Gottfries, Göteborg (SE); Tord Inghardt, Frillesås (SE); Lanna Li, Göteborg (SE); Eva-Lotte Lindstedt Alstermark, Göteborg (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/341,931

(22) PCT Filed: May 31, 1999

(86) PCT No.: PCT/SE99/00942

§ 371 (c)(1),
(2), (4) Date: Jul. 20, 1999

(87) PCT Pub. No.: WO99/26871

PCT Pub. Date: Dec. 9, 1999

(30) Foreign Application Priority Data

Jun. 4, 1998 (SE) ................................. 9801990
Jun. 4, 1998 (SE) ................................. 9801991
Jun. 4, 1998 (SE) ................................. 9801992

(51) Int. Cl.[7] ............................. C07C 69/76
(52) U.S. Cl. ............... 560/55; 560/11; 560/23; 560/41; 562/429; 562/465; 564/162; 558/335; 574/533; 574/534; 574/538; 574/539; 574/562; 574/570

(58) Field of Search .............. 560/11, 23, 41, 560/55; 562/429, 465; 564/162; 558/335; 574/533, 534, 538, 539, 562, 570

(56) References Cited

U.S. PATENT DOCUMENTS

| 5,232,945 A | 8/1993 | Hulin |
| 5,306,726 A | 4/1994 | Hulin |
| 6,258,850 B1 | 7/2001 | Andersson .................. 514/571 |
| 6,362,360 B1 | 3/2002 | Andersson et al. ........... 560/27 |

FOREIGN PATENT DOCUMENTS

| EP | 0428423 | 5/1991 |
| WO | 9119702 | 12/1991 |
| WO | 9731907 | 9/1997 |

OTHER PUBLICATIONS

STN International, File CAPLUS, CAPLUS accession No. 1997:684384; Sankyo Co., Ltd., et al: "Preparation of phenylalkyl–carboxylic acid derivatives lowering blood sugar level", WO,A1,9737970, Oct. 16, 1997.

Tetrahedron Letters, vol. 35, No. 19, 1994, Geoffrey G. Cox et al, "Competing O–H Insertion and Beta–Elimination in Rhodium Carbenoid Reactions; Synthesis of 2–Alkoxy–3–arylpropanoates", pp 3139–3142.

*Primary Examiner*—Paul J. Killos
(74) *Attorney, Agent, or Firm*—White & Case LLP

(57) ABSTRACT

Novel 3-aryl propionic acid derivatives and analogs, process and intermediate for their manufacture, pharmaceutical preparations containing them and the use of the compounds in clinical conditions associated with insulin resistance.

47 Claims, No Drawings

3-ARYL PROPIONIC ACID DERIVATIVES AND ANALOGS

FIELD OF INVENTION

The present invention relates to certain novel 3-aryl-2-hydroxypropionic acid derivatives and analogs, to a process for preparing such compounds, having the utility in clinical conditions associated with insulin resistance, to methods for their therapeutic use and to pharmaceutical compositions containing them.

BACKGROUND OF THE INVENTION

Insulin resistance, defined as reduced sensitivity to the actions of insulin in the whole body or individual tissues such as skeletal muscle, myocardium, fat and liver, prevails in many individuals with or without diabetes mellitus. The insulin resistance syndrome, IRS, refers to a cluster of manifestations including insulin resistance with accompanying hyperinsulinemia, possibly non insulin dependent diabetes mellitus (NIDDM), arterial hypertension, central (visceral) obesity, dyslipidemia observed as deranged lipoprotein levels typically characterized by elevated VLDL (very low density lipoproteins) and reduced HDL (high density lipoproteins) concentrations and reduced fibrinolysis.

Recent epidemiological research has documented that individuals with insulin resistance run a greatly increased risk of cardiovascular morbidity and mortality, notably suffering from myocardial infarction and stroke. In non-insulin dependent diabetes mellitus these atherosclerosis related conditions cause up to 80% of all deaths.

In clinical medicine there is at present only limited awareness of the need to increase the insulin sensitivity in IRS and thus to correct the dyslipidemia which is considered to cause the accelerated progress of atherosclerosis.

Furthermore there is at present no pharmacotherapy available to adequately correct the metabolic derangements associated with IRS. To date, the treatment of NIDDM has been focused on correction of the deranged control of carbohydrate metabolism associated with the disease. Stimulation of endogenous insulin secretion by means of secretagogues, like sulphonylureas, and if necessary administration of exogenous insulin are methods frequently used to normalize blood sugar but that will, if anything, further enhance insulin resistance and will not correct the other manifestations of IRS nor reduce cardiovascular morbidity and mortality. In addition such treatment involves a significant risk of hypoglycemia with associated complications.

Other therapeutic strategies have focused on aberrations in glucose metabolism or absorption, including biguanides, such as methformin, or glucosidase inhibitors, such as acarbose. Although these agents have been efficacious to a degree, their limited clinical effect is associated with side effects.

A novel therapeutic strategy involves the use of insulin sensitizing agents, such as the thiazolidinediones which at least in part mediate their effects via an agonistic action on nuclear receptors. Ciglitazone is the prototype in this class. In animal models of IRS these compounds seem to correct insulin resistance and the associated hypertriglyceridaemia and hyperinsulinemia, as well as hyperglycemia in diabetes, by improving insulin sensitivity via an effect on lipid transport and handling, leading to enhanced insulin action in skeletal muscle, liver and adipose tissue.

Ciglitazone as well as later described thiazolidinediones in clinical development either have been discontinued reportedly due to unacceptable toxicity or show inadequate potency. Therefore there is a need for new and better compounds with insulin sensitizing properties.

Prior Art

Compounds of the Formula

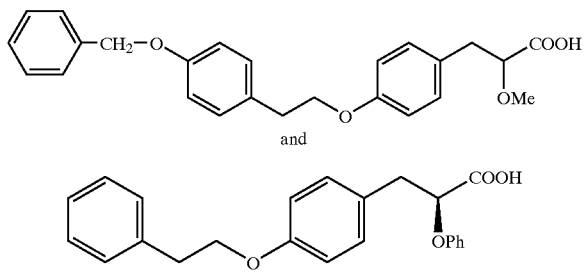

and and certain derivatives thereof disclosed in U.S. Pat. No. 5,306,726 and WO 91/19702 are said to be useful as hypoglycemic and hypocholesterolemic agents, and in U.S. Pat. No. 5,232,945 said to be useful in the treatment of hypertension.

AU 650 429 discloses structurally related compounds, but claimed to have different properties: diuretic, antihypertensive, platelets anti-aggregating and anti-lipoxygenase properties.

EP 139 421 discloses compounds having the ability to lower blood lipid and blood sugar levels. Among these compounds is troglitazone, a compound that has reached the market for treatment of NIDDM or decreased glucose tolerance. WO 97/31907 discloses compounds which are claimed to show good goblood-glucose lowering activity and therefore to be of use in the treatment and/or prophylaxis of hyperglycaemia, dyslipidemia, and are of particular use in the treatment of Type II diabetes.

These compounds are also claimed to be of use for the treatment and/or prophylaxis of other diseases including Type I diabetes, hypertriglyceridemia, syndrome X, insulin resistance, heart failure, diabetic dyslipidemia, hyperlipidemia, hypercholesteremia, hypertension and cardiovascular disease, especially atherosclerosis.

Description of the Invention

The invention relates to compounds of the general formula (I)

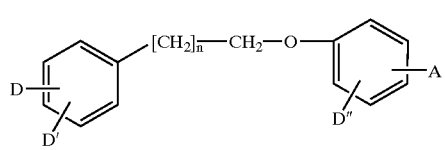

and stereo and optical isomers and racemates thereof as well as pharmaceutically acceptable salts, solvates and crystalline forms thereof, in which formula A is situated in the ortho, meta or para position and represents

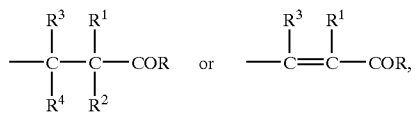

R is hydrogen;
- —$OR^a$, wherein $R^a$ represents hydrogen, alkyl, aryl or alkylaryl;
- —$NR^aR^b$, wherein $R^a$ and $R^b$ are the same or different and $R^a$ is as defined above and $R^b$ represents hydrogen, alkyl, aryl, alkylaryl, cyano, —OH, —Oalkyl, —Oaryl, —Oalkylaryl, —$COR^c$ or —$SO_2R^d$, wherein $R^c$ represents hydrogen, alkyl, aryl or alkylaryl and $R^d$ represents alkyl, aryl or alkylaryl;

$R^1$ is alkyl, aryl, alkene, alkyne, cyano;
- —$OR^e$, wherein $R^e$ is alkyl, acyl, aryl or alkylaryl;
- —O—$[CH_2]_m$—$OR^f$, wherein $R^f$ represents hydrogen, alkyl, acyl, aryl or alkylaryl and m represents an integer 1–8;
- —$OCONR^aR^c$, wherein $R^a$ and $R^c$ are as defined above;
- —$SR^d$, wherein $R^d$ is as defined above;
- —$SO_2NR^aR^f$, wherein $R^f$ and $R^a$ are as defined above;
- —$SO_2OR^a$, wherein $R^a$ is as defined above;
- —$COOR^d$, wherein $R^d$ is as defined above;

$R^2$ is hydrogen, halogen, alkyl, aryl, or alkylaryl,
$R^3$ and $R^4$ are the same or different and each represents hydrogen, alkyl, aryl, or alkylaryl,
n is an integer 1–6,
D is situated in the ortho, meta or para position and represents
- —$OSO_2R^d$, wherein $R^d$ is as defined above;
- —$OCONR^fR^a$, wherein $R^f$ and $R^a$ are as defined above;
- —$NR^cCOOR^d$, wherein $R^c$ and $R^d$ are as defined above;
- —$NR^cCOR^a$, wherein $R^c$ and $R^a$ are as defined above;
- —$NR^cCOR^a$, wherein $R^c$ and $R^a$ are as defined above;
- —$NR^cR^d$, wherein $R^c$ and $R^d$ are as defined above;
- —$NR^cSO_2R^d$, wherein $R^c$ and $R^d$ are as defined above;
- —$NR^cCONR^aR^k$, wherein $R^a$, $R^c$ and $R^k$ are the same or different and each represents hydrogen, alkyl, aryl, or alkylaryl;
- —$NR^cCSNR^aR^k$, wherein $R^a$, $R^c$ and $R^k$ are the same or different and each represents hydrogen, alkyl, aryl or alkylaryl;
- —$SO_2R^d$, wherein $R^d$ is as defined above;
- —$SOR^d$, wherein $R^d$ is as defined above;
- —$SR^c$, wherein $R^c$ is as defined above;
- —$SO_2NR^aR^f$, wherein $R^f$ and $R^a$ are as defined above;
- —$SO_2OR^a$, wherein $R^a$ is as defined above;
- —CN,
- —$CONR^cR^a$, wherein $R^c$ and $R^a$ are as defined above;

D' is situated in the ortho, meta or para position and represents hydrogen, alkyl, acyl, aryl, alkylaryl, halogen, —CN, —$NO_2$, —$NR^fR^b$, wherein $R^f$ and $R^b$ are as defined above;
- —$OR^f$, wherein $R^f$ is as defined above;
- —$OSO_2R^d$, wherein $R^d$ is as defined above;

D" is situated in the ortho, meta or para position and represents hydrogen, alkyl, acyl, aryl, alkylaryl, halogen, —CN, —$NO_2$, —$NR^fR^b$ wherein $R^f$ and $R^b$ are as defined above;
- —$OR^f$, wherein $R^f$ is as defined above.
- —$OSO_2R^d$, wherein $R^d$ is as defined above.

For ease of reference the definitions of formula I above are henceforth referred to as defined in Category A. Unless otherwise stated the definitions of the various substituents are as defined under Category A throughout the present application.

The compounds of the formula I are surprisingly effective in conditions associated with insulin resistance.

Category A2: In one embodiment the present invention does not comprise (S)-2-ethoxy-3-[4-(2-{4-[methanesulfonyloxyphenyl}ethoxy)phenyl]propanoic acid, and 3-{4-[2-(4-tert-butoxycarbonylaminophenyl)ethoxy]phenyl}-(S)-2-ethoxypropanoic acid.

Category A3: preferred compounds of the present invention are those of formula I, wherein A is situated in the meta or para position and represents,

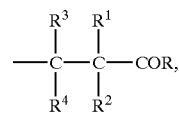

R is hydrogen;
- —$OR^a$, wherein $R^a$ is as defined in Category A;
- —$NR^aR^b$, wherein $R^a$ and $R^b$ are the same or different and $R^a$ is as defined in Category A and $R^b$ represents hydrogen, alkyl, aryl, alkylaryl, cyano, —OH, —Oalkyl or —Oalkylaryl;

$R^1$ is cyano;
- —$OR^d$, wherein $R^d$ is as defined in Category A;
- —O—$[CH_2]_m$—$OR^a$, wherein m and $R^a$ are as defined in Category A;

$R^2$ is hydrogen or alkyl;
$R^3$ is hydrogen or alkyl;
$R^4$ is hydrogen;
n is an integer 1–3;
D is situated in the ortho, meta or para position and represents
- —$OSO_2R^d$, wherein $R^d$ is as defined in Category A;
- —$OCONR^aR^c$, wherein $R^a$ and $R^c$ are as defined in Category A;
- —$NR^cCOOR^d$, wherein $R^c$ and $R^d$ are as defined in Category A;
- —$NR^cCOR^a$, wherein $R^c$ and $R^a$ are as defined in Category A;
- —$NR^cR^d$, wherein $R^c$ and $R^d$ are as defined in Category A;
- —$NR^cSO_2R^d$, wherein $R^c$ and $R^d$ are as defined in Category A;
- —$NR^cCONR^kR^c$, wherein $R^a$, $R^c$ and $R^k$ are as defined in Category A;
- —$NR^cCSNR^aR^k$, wherein $R^a$, $R^c$ and $R^k$ are as defined in Category A;
- —$SO_2R^d$, wherein $R^d$ is as defined in Category A;
- —$SR^c$, wherein $R^c$ is as defined in Category A;
- —CN;
- —$CONR^aR^c$, wherein $R^a$ and $R^c$ are as defined in in Category A;

D' is situated in the ortho, meta or para position and represents hydrogen, alkyl, alkylaryl, halogen, —CN or —$NO_2$;
- —$OR^h$, wherein $R^h$ is hydrogen or alkyl;

D" is situated in the ortho, meta or para position and represents hydrogen, alkyl, alkylaryl, halogen, —CN or —$NO_2$;
- —$OR^h$, wherein $R^h$ is as defined above.

Category A4: further preferred compounds of the present invention are those within Category A3, wherein
  A is situated in the meta or para position;
  R is —$OR^a$, wherein $R^a$ is hydrogen, alkyl or alkylaryl;
    —$NHR^b$, wherein $R^b$ is hydrogen, alkyl, alkylaryl, cyano, —Oalkyl or —Oalkylaryl;
  $R^1$ is —Oalkyl;
  $R^2$ is hydrogen or alkyl;
  $R^3$ is hydrogen or alkyl;
  $R^4$ is hydrogen;
  n is an integer 1–3,
  D is situated in the ortho, meta or para position and represents
    —$NR^cCOOR^d$, wherein $R^c$, and $R^d$ are as defined in Category A;
  D' is hydrogen.
  D" is hydrogen.

Category A5: further preferred compounds of the present invention are those within Category A4, wherein
  A is situated in the para position;
  R is —OH, —Oalkyl or —Oalkylaryl;
    —$NH_2$, —NHOalkylaryl or —NHCN;
  $R^1$ is —Oalkyl, preferably —Olower alkyl;
  $R^2$ is hydrogen;
  $R^3$ is hydrogen;
  n is the integer 1;
  D is situated in the para position, and represents —$NR^hCOOR^d$, wherein
    $R^d$ is as defined in Category A and $R^h$ represents hydrogen or alkyl.

Category A6: further preferred compounds of the present invention are those within Category A5, wherein
  D is —$NR^jCOOalkyl$ wherein $R^j$ represents hydrogen and lower alkyl.

Category A7: further preferred compounds of the present invention are those within Category A3, wherein
  A is situated in the meta or para position.
  R is —$OR^a$, wherein $R^a$ is hydrogen, alkyl or alkylaryl;
    —$NHR^b$, wherein $R^b$ is hydrogen, alkyl, alkylaryl, cyano, —Oalkyl or —Oalkylaryl;
  $R^1$ is —Oalkyl;
  $R^2$ is hydrogen or alkyl;
  $R^3$ is hydrogen or alkyl;
  $R^4$ is hydrogen;
  n is an integer 1–3;
  D is situated in the ortho, meta or para position and represents
    —$NR^cCOR^a$, wherein $R^c$ and $R^a$ are as defined in Category A;
  D' is hydrogen.
  D" is hydrogen.

Category A8: further preferred compounds of the present invention are those within Category A7 wherein
  A is situated in the para position;
  R is —OH, —Oalkyl or —Oalkylaryl;
    —$NH_2$, —NHOalkylaryl or —NHCN;
  $R^1$ is —Oalkyl, preferably —Olower alkyl;
  $R^2$ is hydrogen;
  $R^3$ is hydrogen;
  n is the integer 1;
  D is situated in the para position, and represents —$NR^hCOR^d$, wherein
    $R^d$ is as defined in Category A and $R^h$ represents hydrogen or alkyl.

Category A9: further preferred compounds of the present invention are those within Category A8, wherein
  D is —$NHCOR^d$, wherein $R^d$ is as defined in Category A.

Category A10: further preferred compounds of the present invention are those within Category A3, wherein
  A is situated in the meta or para position,
  R is —$OR^a$, wherein $R^a$ is hydrogen, alkyl or alkylaryl;
    —$NHR^b$, wherein $R^b$ is hydrogen, alkyl, alkylaryl, cyano, —Oalkyl or —Oalkylaryl;
  $R^1$ is —Oalkyl,
  $R^2$ is hydrogen;
  $R^3$ is hydrogen or alkyl;
  $R^4$ is hydrogen;
  n is an integer 1–3;
  D is situated in the ortho, meta or para position and represents
    —$SO_2R^d$, wherein $R^d$ is as defined in Category A;
  D' is hydrogen;
  D" is hydrogen.

Category A11: further preferred compounds of the present invention are those within Category A10, wherein
  A is situated in the para position;
  R is —OH, —Oalkyl or —Oalkylaryl;
    —$NH_2$, —NHOalkylaryl or —NHCN;
  $R^1$ is —Oalkyl, preferably —Olower alkyl;
  $R^3$ is hydrogen;
  n is the integer 1;
  D is situated in the para position and represents —$SO_2R^d$, wherein $R^d$ is as defined in Category A.

Category A12: further preferred compounds of the present invention are those within Category A3, wherein
  A is situated in the meta or para position,
  R is —$OR^a$, wherein $R^a$ is hydrogen, alkyl or alkylaryl;
    —$NHR^b$, wherein $R^b$ is hydrogen, alkyl, alkylaryl, cyano, —Oalkyl or —Oalkylaryl;
  $R^1$ is —Oalkyl;
  $R^2$ is hydrogen;
  $R^3$ is hydrogen or alkyl,
  $R^4$ is hydrogen;
  n is an integer 1–3;
  D is situated in the ortho, meta or para position and represents
    —$SR^d$, wherein $R^d$ is as defined in Category A;
  D' is hydrogen;
  D" is hydrogen.

Category A13: further preferred compounds of the present invention are those within Category A12, wherein
  A is situated in the para position;
  R is —OH, —Oalkyl, —Oalkylaryl;
    —$NH_2$, —NHOalkylaryl or —NHCN;
  $R^1$ is —Oalkyl, preferably —Olower alkyl;
  $R^3$ is hydrogen;
  n is the integer 1;
  D is situated in the para position and represents —$SR^d$, wherein $R^d$ is as defined in Category A.

Category A14: further preferred compounds of the present invention are those within Category A3, wherein
- A is situated in the meta or para position,
- R is —OR$^a$, wherein R$^a$ is hydrogen, alkyl, alkylaryl; —NHR$^b$, wherein R$^b$ is hydrogen, alkyl, alkylaryl, cyano, —Oalkyl or —Oalkylaryl;
- R$^1$ is —Oalkyl;
- R$^2$ is hydrogen or alkyl;
- R$^3$ is hydrogen or alkyl;
- R$^4$ is hydrogen;
- n is an integer 1–3,
- D is situated in the ortho, meta or para position and represents
  - —OCONR$^a$R$^c$, wherein R$^a$ and R$^c$ are as defined in Category A;
- D' is hydrogen;
- D" is hydrogen.

Category A15: further preferred compounds of the present invention are those within Category A14, wherein
- A is situated in the para position;
- R is —OH, —Oalkyl, —Oalkylaryl; —NH$_2$, —NHOalkylaryl, —NHCN;
- R$^2$ is hydrogen;
- R$^3$ is hydrogen;
- n is the integer 1;
- D is situated in the para position, and represents
  - —OCONHR$^d$, wherein R$^d$ is as defined in Category A.

Category A16: further preferred compounds of the present invention are those within Category A15, wherein
- R$^1$ is —Oalkyl, preferably —Olower alkyl;
- D is —OCONHalkyl.

Category A17: further preferred compounds of the present invention are those within
Category A3, wherein
- A is situated in the meta or para position,
- R is —OR$^a$, wherein R$^a$ is hydrogen, alkyl, alkylaryl; —NHR$^b$, wherein R$^b$ is hydrogen, alkyl, alkylaryl, cyano, —Oalkyl or —Oalkylaryl;
- R$^1$ is —Oalkyl,
- R$^2$ is hydrogen or alkyl;
- R$^3$ is hydrogen or alkyl,
- R$^4$ is hydrogen;
- n is an integer 1–3;
- D is situated in the ortho, meta or para position and represents
  - —NR$^c$SO$_2$R$^d$, wherein R$^c$ and R$^d$ are as defined in Category A;
- D' is hydrogen;
- D" is hydrogen.

Category A18: further preferred compounds of the present invention are those within Category A17, wherein
- A is situated in the para position;
- R is —OH, —Oalkyl, —Oalkylaryl; —NH$_2$, —NHOalkylaryl or —NHCN;
- R$^2$ is hydrogen;
- R$^3$ is hydrogen;
- n is the integer 1;
- D is situated in the para position, and represents
  - —NR$^h$SO$_2$R$^d$, wherein R$^d$ is as defined in Category A and R$^h$ is hydrogen or alkyl.

Category A19: further preferred compounds of the present invention are those within Category A18, wherein
- R$^1$ is —Oalkyl, preferably —Olower alkyl;
- D is —NR$^h$SO$_2$alkyl wherein R$^h$ is as defined above.

Category A20: further preferred compounds of the present invention are those within Category A3, wherein
- A is situated in the meta or para position;
- R is —OR$^a$, wherein R$^a$ is hydrogen, alkyl or alkylaryl; NHR$^b$, wherein R$^b$ is hydrogen, alkyl, alkylaryl, cyano, —Oalkyl or —Oalkylaryl;
- R$^1$ is —Oalkyl;
- R$^2$ is hydrogen or alkyl;
- R$^3$ is hydrogen or alkyl;
- R$^4$ is hydrogen;
- n is an integer 1–3;
- D is situated in the ortho, meta or para position and represents
  - —NR$^c$R$^d$, wherein R$^c$ and R$^d$ are as defined in Category A;
- D' is hydrogen;
- D" is hydrogen.

Category A21: further preferred compounds of the present invention are those within Category A20, wherein
- A is situated in the para position;
- R is —OH, —Oalkyl, —Oalkylaryl; —NH$_2$, —NHOalkylaryl or —NHCN;
- R$^2$ is hydrogen;
- R$^3$ is hydrogen;
- n is the integer 1;
- D is situated in the para position, and represents
  - —NR$^h$R$^d$ wherein R$^d$ is as defined in Category A and R$^h$ is hydrogen or alkyl.

Category A22: further preferred compounds of the present invention are those within Category A21, wherein
- R$^1$ is —Oalkyl, preferably —Olower alkyl;
- D is —NR$^h$alkyl wherein R$^h$ is hydrogen or alkyl.

Category A23: further preferred compounds of the present invention are those within Category A3, wherein
- A is situated in the meta or para position;
- R is —OR$^a$, wherein R$^a$ is hydrogen, alkyl or alkylaryl; —NHR$^b$, wherein R$^b$ is hydrogen, alkyl, alkylaryl, cyano, —Oalkyl or —Oalkylaryl;
- R$^1$ is —Oalkyl;
- R$^2$ is hydrogen or alkyl;
- R$^3$ is hydrogen or alkyl,
- R$^4$ is hydrogen;
- n is an integer 1–3;
- D is situated in the ortho, meta or para position and represents
  - —NR$^c$CONR$^a$R$^k$, wherein R$^a$, R$^c$ and R$^k$ are as defined in Category A;
- D' is hydrogen;
- D" is hydrogen.

Category A24: further preferred compounds of the present invention are those within Category A23, wherein
- A is situated in the para position;
- R is —OH, —Oalkyl, —Oalkylaryl; —NH$_2$, —NHOalkylaryl or —NHCN;
- R$^2$ is hydrogen;
- R$^3$ is hydrogen;
- n is the integer 1;
- D is situated in the para position, and represents
  - —NHCONHR$^d$, wherein R$^d$ is as defined in Category A.

Category A25: further preferred compounds of the present invention are those within Category A24, wherein
$R^1$ is —Oalkyl, preferably —Olower alkyl;
D is —NHCONHalkyl.

Category A26: further preferred compounds of the present invention are those within Category A3, wherein
A is situated in the meta or para position;
R is —$OR^a$, wherein $R^a$ is hydrogen, alkyl or alkylaryl; $NHR^b$, wherein $R^b$ is hydrogen, alkyl, alkylaryl, cyano, —Oalkyl or —Oalkylaryl;
$R^1$ is —Oalkyl;
$R^2$ is hydrogen or alkyl;
$R^3$ is hydrogen or alkyl;
$R^4$ is hydrogen;
n is an integer 1–3;
D is situated in the ortho, meta or para position and represents
—$NR^cCSNR^aR^k$, wherein $R^a$, $R^c$ and $R^k$ are as defined in Category A;
D' is hydrogen;
D" is hydrogen.

Category A27: further preferred compounds of the present invention are those within Category A26, wherein
A is situated in the para position;
R is —OH, —Oalkyl, —Oalkylaryl; —$NH_2$, —NHOalkylaryl or —NHCN;
$R^2$ is hydrogen;
$R^3$ is hydrogen;
n is the integer 1;
D is situated in the para position, and represents —$NHCSNHR^d$, wherein $R^d$ is as defined in Category A.

Category A28: further preferred compounds of the present invention are those within Category A27, wherein
$R^1$ is —Olower alkyl.
D is —NHCSNHalkyl.

Category A29: further preferred compounds of the present invention are those within Category A3, wherein
A is situated in the meta or para position;
R is —$OR^a$, wherein $R^a$ is hydrogen, alky, alkylaryl; —$NHR^b$, wherein $R^b$ is hydrogen, alkyl, alkylaryl, cyano, —Oalkyl or —Oalkylaryl;
$R^1$ is —Oalkyl;
$R^2$ is hydrogen or alkyl;
$R^3$ is hydrogen or alkyl;
$R^4$ is hydrogen;
n is an integer 1–3;
D is situated in the ortho, meta or para position and represents
—$OSO_2R^d$, wherein $R^d$ is as defined in Category A;
D' is hydrogen;
D" is hydrogen.

Category A30: further prefered compounds of the present invention are those within Category A29, wherein
A is situated in the para position;
R is —OH, —Oalkyl, —Oalkylaryl; —$NH_2$, —NHOalkylaryl or —NHCN;
$R^2$ is hydrogen;
$R^3$ hydrogen;
n is the integer 1;
D is situated in the para position and represents —$OSO_2$alkyl or —$OSO_2$alkylaryl.

Category A31: further preferred compounds of the present invention are those within Category A30, wherein
$R^1$ is —Oalkyl, preferably —Olower alkyl;
D is —$OSO_2$ alkyl.

Category A32: further preferred compounds of the invention are
2-Ethoxy-3-[4-(2-{4-methanesulfonyloxyphenyl}ethoxy)phenyl]propanoic acid;
3-{4-[2-(4-tert-Butoxycarbonylaminophenyl)ethoxy]phenyl}-2-ethoxypropanoic acid;
2-Ethoxy-3-{4-[2-(4-methanesulfonylphenyl)ethoxy]phenyl}propanoic acid;
2-Ethoxy-3-{4-[2-(4-methylsulfanylphenyl)ethoxy]phenyl}propanoic acid;
2-Ethoxy-3-[4-(2-{4-isobutyrylaminophenyl}ethoxy)phenyl]propanoic acid;
3-{4-[2-(4-tert-Butylcarbamoyloxyphenyl)ethoxy]phenyl}-2-ethoxypropanoic acid ethyl ester;
2-Ethoxy-3-{4-[2-(4-methanesulfonylaminophenyl)ethoxy]phenyl}propanoic acid;
N-Cyano-2-ethoxy-3-[4(2-{4-methanesulfonyloxyphenyl}ethoxy)phenyl]propanoic amide;
N-Benzyloxy-2-ethoxy-3-[4-(2-{4-methanesulfonyloxyphenyl}ethoxy)phenyl]propanoic amide;
2-Ethoxy-3-[4-(2-{4-methanesulfonyloxyphenyl}ethoxy)phenyl]propanoic amide;
2-Ethoxy-3-{4-[3-(3-methanesulfonyloxyphenyl)propoxy]phenyl}propanoic acid ethyl ester;
2-Ethoxy-3-(4-{2-[4-(2-propanesulfonyloxy)phenyl]ethoxy}phenyl)propanoic acid;
3-[4-{2-(4-[tert-Butoxycarbonyl(methyl)amino]phenyl)ethoxy}phenyl]-(S)-2-ethoxypropanoic acid;
(S)-2-Ethoxy-3-[4-{2-[4-(methoxycarbonylamino)phenyl)ethoxy]phenyl}propanoic acid;
2-Ethoxy-3-{4-[2-(4-methylcarbamoyloxyphenyl)ethoxy]phenyl}propanoic acid ethyl ester;
3-[4-{2-(4-[Benzyloxycarbonylamino]phenyl)ethoxy}phenyl]-(S)-2-ethoxypropanoic acid;
3-{4-[2-(4-tert-Butoxycarbonylaminophenyl)ethoxy]-3-methoxyphenyl}-2-ethoxypropanoic acid;
3-[4-(2-{4-tert-Butoxycarbonylaminophenyl}ethoxy)phenyl]-2-(2,2,2-trifluoroethoxy)propanoic acid methyl ester;
(S)-2-Ethoxy-3-(4-{2-[4-(phenylsulfonyl)phenyl]ethoxy}phenyl)propanoic acid;
and, where applicable, stereo and optical isomers and racemates thereof as well as pharmaceutically acceptable salts, solvates and crystalline forms thereof.

Category A33: further preferred compounds of the present invention are compounds which are one of the possible enantiomers.

When alkyl is included in the substituent D the preferred alkyls are methyl, ethyl, propyl, isopropyl and tertiary butyl.

When the substituent $R^1$ represents an alkyl group, the preferred alkyls are alkyl groups having from 2 to 6 carbon atoms.

When the substituent $OR^a$ represents an alkylaryl group, the preferred alkylaryl is benzyl.

In the present specification the expression "pharmaceutically acceptable salts" is intended to define but is not limited to such base salts as the alkali metal salts, alkaline earth metal salts, aluminium, zinc and bismuth salts, ammonium salts, salts with basic amino acids, and salts with organic amines.

Throughout the specification and the appended claims, a given chemical formula or name shall encompass all stereo and optical isomers and racemates thereof (with the exception of the compounds of Category A2), as well as mixtures in different proportions of the separate enantiomers, where such isomers and enantiomers exist, as well as pharmaceutically acceptable salts thereof and solvates thereof such as for instance hydrates. Isomers may be separated using conventional techniques, e.g. chromatography or fractional crystallization. The enantiomers may be isolated by separation of racemate for example by fractional crystallization, resolution or HPLC. The diastereomers may be isolated by separation of isomer mixtures for instance by fractional crystallization, HPLC or flash chromatography. Alternatively the stereoisomers may be made by chiral synthesis from chiral starting materials under conditions which will not cause racemisation or epimerisation, or by derivatisation, with a chiral reagent. All stereoisomers are included within the scope of the invention.

The following definitions shall apply throughout the specification and the appended claims.

Unless otherwise stated or indicated, the term "alkyl" denotes a straight or branched, substituted or unsubstituted alkyl group having from 1 to 6 carbon atoms or a cyclic alkyl having from 3 to 6 carbon atoms. The term "lower alkyl" denotes a straight or branched, substituted or unsubstituted alkyl group having from 1 to 3 carbon atoms or a cyclic alkyl having 3 carbon atoms. Examples of said alkyl and lower alkyl include methyl, ethyl, n-propyl, isopropyl, n-butyl, iso-butyl, sec-butyl, t-butyl and straight- and branched-chain pentyl and hexyl as well as cyclopropyl, cyclobutyl, cyclopentyl and cyclohexyl.

Unless otherwise stated or indicated, the term "alkoxy" denotes a group O-alkyl, wherein alkyl is as defined above.

Unless otherwise stated or indicated, the term "halogen" shall mean fluorine, chlorine, bromine or iodine.

Unless otherwise stated or indicated, the term "aryl" denotes a substituted or unsubstituted phenyl, furyl, thienyl or pyridyl group, or a fused ring system of any of these groups, such as naphthyl.

Unless otherwise stated or indicated, the term "substituted" denotes an alkyl or an aryl group as defined above which is substituted by one or more alkyl, alkoxy, halogen, amino, thiol, nitro, hydroxy, acyl, aryl or cyano groups.

Unless otherwise stated or indicated, the term "alkylaryl" denotes a

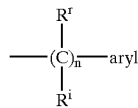

wherein n is an integer 1 to 6 and $R^r$ and $R^1$ are the same or different and each represents hydrogen or an alkyl or aryl group as defined above.

Unless otherwise stated or indicated, the term "acyl" denotes a group

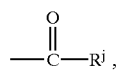

wherein $R^j$ is hydrogen, alkyl, alkoxy, aryl and alkylaryl as defined above.

Unless otherwise stated or indicated, the terms "alkenyl" and "alkynyl" denote a straight or branched, substituted or unsubstituted unsaturated hydrocarbon group having one or more double or triple bonds and having a maximum of 6 carbon atoms, preferably 3 carbon atoms.

Unless otherwise stated or indicated the term "protective group" ($R^p$) denotes a protecting group as described in the standard text "Protecting groups in Organic Synthesis", 2nd Edition (1991) by Greene and Wuts. The protective group may also be a polymer resin such as Wang resin or 2-chlorotrityl chloride resin.

Methods of Preparation

The compounds of the invention may be prepared as outlined below according to any of methods A–J. However, the invention is not limited to these methods, the compounds may also be prepared as described for structurally related compounds in the prior art.

A. The compounds of the invention of formula I wherein $R^2$ and $R^4$ are hydrogen can be prepared by a condensation reaction, such as a Knoevenagel or Wittig type reaction, of a carbonyl compound of the formula II

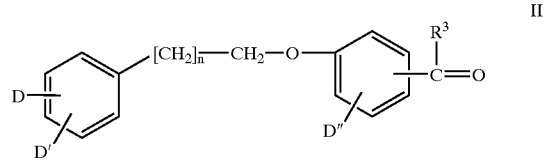

with a compound of the formula III or IV

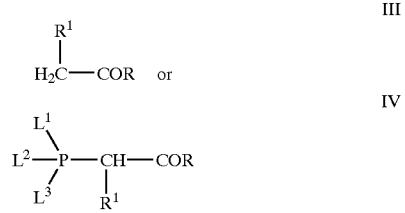

in which formulas D, D', D", n, R, $R^1$ and $R^3$ are as defined in Category A and $L^1=L^2=L^3$ are phenyl or $L^1=L^2$ are $OR^d$ (wherein $R^d$ is as defined in Category A) and $L^3$ is =O, and if desired, followed by reduction of the obtained double bond and removal of protective groups.

A1. In the condensation step approximately equimolar amounts of reactants are mixed in the presence of a base, such as sodium acetate, piperidine acetate, LDA or potassium tert-butoxide to provide the compound of formula I wherein A is the unsaturated moiety. This step may be carried out in the presence of an inert solvent or in the absence of solvent in which case the temperature should be sufficiently high to cause at least partial melting of the reaction mixture, a preferred such temperature is in the range of 100° C. to 250° C.

Sometimes it is necessary to add a dehydrating agent such as p-toluenesulfonic acid in order to achieve the formation of the double bond.

In a typical such reaction the aldehyde or ketone starting material and the compound of formula III are combined in approximately equimolar amounts and molar excess, preferably 1–5 fold, of anhydrous sodium acetate and the mixture is heated until it melts if necessary under vacuum. The compound of formula I wherein A is the unsaturated moiety, can then be isolated by mixing with water and acetone, followed by filtration of the formed precipitate. The crude product can be purified if desired, e.g. by recrystallization or by standard chromatographic methods.

This reaction can also be performed conveniently in a solvent such as toluene in the presence of piperidine acetate. The reaction mixture is refluxed in a Dean-Stark apparatus to remove water. The solution is then cooled and the olefin product isolated and purified, by standard methods.

The reaction can also be performed by mixing the aldehyde or ketone and the compound of formula II in dry tetrahydrofuran, slowly adding potassium tert-butoxide at −20° C. and quenching the reaction with acetic acid. The crude product is isolated and then dissolved in toluene and refluxed with p-toluenesulfonic acid in an Dean-Stark apparatus to remove the water. The product is then isolated and purified, by standard methods.

A2. The reaction can also be performed in the presence of titanium (IV) chloride and pyridine in an inert solvent, such as chloroform.

A3. The condensation step could also be performed as a Wittig-type reaction (cf. Comprehensive Organic Synthesis vol. 1 p. 755–781 Pergamon Press) or as described in the experimental part.

Approximately equimolar amounts of reactants II and IV, are mixed in the presence of a base such as tetramethylguanidine or potassium carbonate in a 1–5-fold molar excess. This reaction may be carried out in the presence of an inert solvent such as dichloromethane or isopropanol at a suitable temperature (−10° C.−+60° C.) and at a time long enough.

The compound of the formula II is prepared by coupling a compound of the formula V

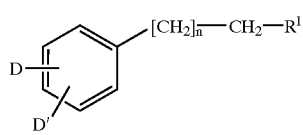

with a compound of the formula VI

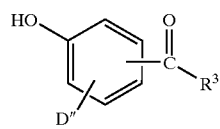

in which formulas D, D', D", n and $R^3$ are as defined in Category A, at, for example alkylation conditions or by a Mitsunobu reaction (Tsunoda, Tetr. Lett. 34, 163942 (1993), when necessary followed by modifications of the D-groups as described in the experimental section.

The group $R^1$ can be —OH or a leaving group, such as halogen, sulfonate or triflate.

The alkylation reaction and the Mitsunobu reaction can be carried out as described below or as in the experimental section.

The compounds of formula III, IV, V or VI are either commercially available or can be prepared by standard procedures known to anyone skilled in the art from commercially available starting materials or by procedures described in the experimental section. The reduction of the olefin may be carried out by using a wide variety of reducing methods known to reduce carbon-carbon double bonds, such as catalytic hydrogenation in the presence of an appropriate catalyst, magnesium or sodium amalgam in a lower alcohol such as methanol, or hydrogen transfer reagents such as diethyl-2,5-dimethyl-1,4-dihydropyridine-3,5-dicarboxylate.

The catalytic hydrogenation can be conducted in alcohol, cellosolves, protic polar organic solvents, ethers, lower alifatic acids, and particularly in methanol, ethanol, methoxyethanol, dimethylformamide, tetrahydrofuran, dioxane, dimetoxyethane, ethyl acetate or acetic acid, either used alone or in mixture. Examples of the catalyst used include palladium black, palladium on activated charcoal, platinum oxide or Wilkinson's catalyst. The reaction can proceed at different temperatures and pressures depending on the reactivity of the aimed reaction.

In case of hydrogen transfer reaction with diethyl-2,5-dimethyl-1,4-dihydropyridine-3,5-dicarboxylate, equimolar amounts of reactants are mixed and the mixture is warmed to melting (140° C.–250° C.) under inert atmosphere or under vacuum.

B. The compounds of the invention of formula I where A=—$CR^3R^4$—$CR^1R^2$—COR, wherein $R^4$ is hydrogen can be prepared by reacting a carbonyl compound of formula II

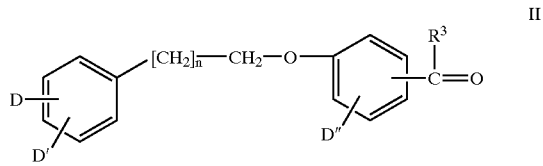

with a compound of formula VII

in which formulas D, D', D", n, $R^1$ and $R^3$ are as defined in Category A and $R^2$ is alkyl, aryl or alkylaryl, followed by dehydroxylation and if necessary by removal of protective groups.

In the reaction the compound of formula II is reacted with a compound of formula VII in the presence of a strong base such as LDA in an inert solvent followed by addition of a dehydroxylating agent such as borontrifluoride etherate.

The reaction can be carried out as described in the experimental section or by standard methods know to anyone skilled in the art.

The compound of formula VII are either commercially available or can be prepared by standard procedures.

C. The compounds of the invention of formula I where A=$CR^3R^4$—$CR^1R^2$—COR, can be prepared by an alkylation reaction with a compound of formula VIII

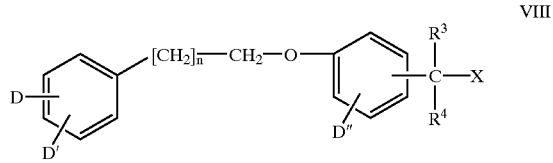

where in X is a leaving group, such as halogen, sulfonates or triflates, on a compound of formula VII,

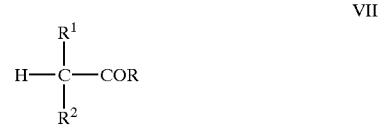

in which formulas D, D', D", n, R, $R^1$, $R^2$, $R^3$ and $R^4$ are as defined in Category A and, if desired, followed by removal of protective groups.

In the alkylation step the compound of formula VII is reacted with a compound of formula VIII in the presence of one or more bases such as potassium carbonate, triethylbenzylammonium chloride, sodium hydride, LDA, butyllithium or LHMDS and in a inert solvent such as acetonitrile, DMF or dichloromethane at a suitable temperature and time. The reaction can be carried out as described in the examples or by standard methods known in the literature. (Synth. Comm. 19(788)1167–1175 (1989)).

The compound of formula VIII can be prepared from an alcohol of formula IX

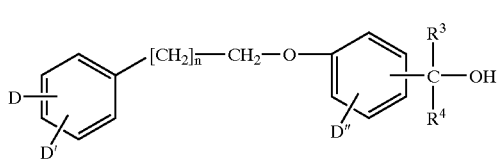

IX wherein D, D', D", n, $R^3$ and $R^4$ are as defined in Category A using standard methods or as described in the experimental section.

The compound of formula IX can be prepared from a compound of formula II either by reduction with a reducing agent known to convert a carbonyl group to a hydroxyl group such as lithium borohydride or sodium borohydride or by reaction with an organometallic compound such as an organolithium or a Grignard reagent by standard methods or as described in the experimental section.

D. The compounds of the invention of formula I can be prepared by reaction of a compound of the formula

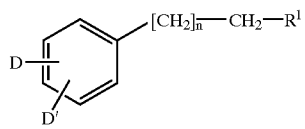

V with a compound of the formula X

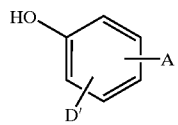

X in which formulas D, D', D", n and A are as defined in Category A, and $R^1$ is —OH or a leaving group such as halogen, sulfonate, triflate, either by an alkylation reaction or a Mitsunobu reaction, when nessecary followed by removal of protective groups.

The compound of formula X can be prepared in accordance to method A from commercially available starting materials and compounds of formula III or IV.

D1. In an alkylation reaction the leaving group $R^1$ can be a sulfonate such as mesylate, nosylate, tosylate, or a halogen, such as bromine or iodine. The compounds of formula V and X, in approximately equimolar amounts or with an excess of one of the compounds, are heated to reflux temperature in an inert solvent, such as isopropanol or acetonitrile, in the presence of a base, such as potassium carbonate or cesium carbonate.

The mixture is refluxed for the necessary time, typically between 0.5 h to 24 h, the work up procedure usually include filtration, for removal of solid salt, evaporation and extraction with water and an organic solvent such as dichloromethane, ethyl acetate, or diethyl ether. The crude product is purified if desired e.g. by recrystallization or by standard chromatographic methods.

D2. The Mitsunobu reaction can be carried out according to standard methods.

In a typical Mitsunobu reaction a compound of formula V, wherein the group $R^1$ is a hydroxyl group, and a compound of formula X are mixed, in approximately equimolar amounts or with an excess of one of the compounds, in an inert solvent, such as chloroform, dichloromethane, or tetrahydrofuran. A slight molar excess of an azodicarboxylate, (1–4 equivalents) such as DEAD or ADDP and a phosphine (1–4 equivalents), such as tributylphosphine or triphenylphosphine are added and the reaction mixture is stirred at a temperature high enough, for example room temperature, and a time long enough (1–24 hours) to obtain the crude product, which can be worked up according to standard litterature methods and if desired purified, e.g. by standard chromatographic methods.

E. The compounds of the invention of formula I, wherein A is —$CR^3R^4$—$CR^1RR^2$—COR, wherein R, $R^2$, $R^3$ and $R^4$ are as defined in Category A and $R^1$ is —$OR^e$, wherein $R^e$ is as defined in Category A, —O—$[CH_2]_m$—$OR^f$, wherein m and $R^f$ are as defined in Category A, —$OCONR^aR^c$, wherein $R^a$ and $R^c$ are as defined in Category A, can be prepared by converting a compound of formula XI

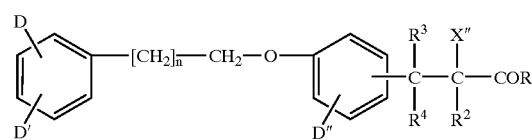

XI wherein D, D', D", n, R, $R^2$, $R^3$ and $R^4$ are as defined in Category A and X" is —OH followed, if necessary, by removal of protective groups.

The reaction may be carried out as an alkylating reaction, a Mitsunobu reaction, an esterfication reaction or by reaction with isocyanates. The alkylating reaction may be carried out using a variety of alkylating agents, such as alkyl halide. The esterfication reaction may be carried out using a variety of acylating agents such as Cl—CO—$R^d$ (wherein $R^d$ is as defined in Category A) and the Mitsunobu reaction may be carried out using an alcohol such as phenol. The reactions can be carried out in accordance with methods known to those skilled in the art or as described in the examples.

The compound of formula XI can be prepared by reaction of a compound of formula V

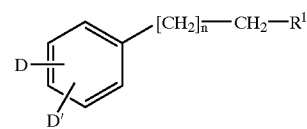

V with a compound of formula XII

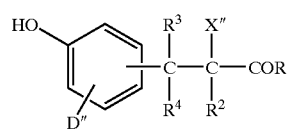

XII wherein D, D', D", n, R, $R^2$, $R^3$, $R^4$ are as defined in Category A and $R^1$ is —OH or a leaving group such as halogen, sulfonate or triflate and X" is —OH followed, if necessary, by removal of protective groups.

The reaction can be performed as described above or by standard methods know to anyone skilled in the art.

The compound of the formula XII can be prepared according to literature methods from commercially available starting materials.

F. The compounds of the formula I wherein A is —$CR^3R^4$—$CR^1R^2$—COR, and R, $R^2$, $R^3$ and $R^4$ are as defined in Category A and $R^1$ is —$SR^d$, wherein $R^d$ is as defined in Category A, can be prepared by reacting a compound of the formula XIII

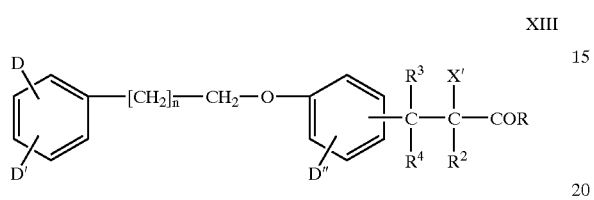

XIII wherein D, D', D", n, R, $R^2$, $R^3$, $R^4$ are as defined in Category A and X' is halogen, a thiol in a substitution reaction. The reaction can be carried out in accordance to methods known to those skilled in the art or as described in the examples.

The compound of formula XIII can be prepared in accordance to method D from either commercially available starting materials or from starting materials prepared by standard procedures from commercially available starting materials.

G. The compounds of the invention of formula I wherein D is —$OSO_2R^d$, —$SR^c$, —$OCONR^fR^a$, —$NR^cCOOR^d$, —$NR^cCOR^a$, —$NR^cR^d$, —$NR^cCONR^aR^k$, $NR^cSO_2R^d$ and —$NR^cCSNR^aR^k$, wherein $R^a$, $R^c$, $R^d$, $R^f$, $R^g$ and $R^k$ are as defined in Category A, can be prepared by reacting a compound of formula XIV

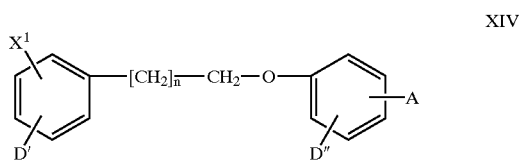

XIV wherein D', D", n and A are as defined in Category A and $X^1$=—OH, —SH or —$NR^cH$, with a suitable reagent, such as a sulfonylhalide, isocyanate, acylhalide, chloroformate, anhydride or an alkylhalide in an inert solvent such as dichloromethane or toluene and when necessary in the presence of a base, such as triethylamine or pyridine and eventually followed by removal of protective groups.

The reaction can be carried out in accordance with methods know to those skilled in the art or as described in the examples.

H. The compounds of the invention of formula I where R is —OH can be prepared from a compound of formula I where in R is —$OR^p$, wherein $R^p$ is a protective group such as alkyl, aryl, alkylaryl or a polymer resin such as Wang resin or 2-chlorotrityl chloride resin, by removal of the protective group by hydrolysis. The hydrolysis can be performed according to standard methods either under basic or acidic conditions.

I. The compound of the invention of formula I wherein R is —$NR^aR^b$ can be prepared by reacting a compound of formula I when R is —OH with a compound of formula HN$R^aR^b$ in the presence of a peptide coupling system (e.g. EDC, DCC, HBTU, TBTU or PyBop or oxalylchloride in DMF), an appropriate base (e.g. pyridine, DMAP, TEA or DiPEA) and a suitable organic solvent (e.g. dichloromethane, acetonitrile or DMF) in accordance to methods known to those skilled in the art or as described in the examples.

J. The compounds of the invention of formula I where D is —$SO_2R^d$ or —SOR, wherein $R^d$ is as defined in Category A, can be prepared by oxidizing a compound of formula XV

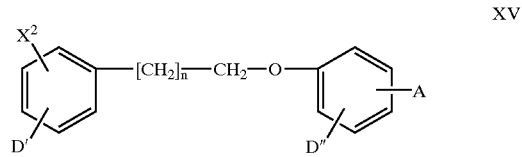

XV wherein D', D", n and A are as defined in Category A and $X^2$ is —$SOR^d$ or —$SR^d$, wherein $R^d$ is as defined in Category A with oxidizing agents such as m-chloroperoxybenzoic acid or hydrogen peroxide in an inert solvent such as dichloromethane eventually followed by removal of protective groups.

The reactions can be carried out according to standard procedures or as described in the experimental section.

The compounds of the invention may be isolated from their reaction mixtures using conventional techniques.

Persons skilled in the art will appreciate that, in order to obtain compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

In any of the preceeding methods of preparation A-J, where necessary, hydroxy, amino or other reactive groups may be protected using a protecting group, $R^p$ as described in the standard text "Protective groups in Organic Synthesis", 2nd Edition (1991) by Greene and Wuts. The protecting group $R^p$ may also be a resin, such as Wang resin or 2-chlorotrityl chloride resin. The protection and deprotection of functional groups may take place before or after any of the reaction steps described hereinbefore. Protecting groups may be removed in accordance to techniques which are well known to those skilled in the art.

The expression "inert solvent" refers to a solvent which does not react with the starting materials, reagents, intermediates or products in a manner which adversely affects the yield of the desired product.

Pharmaceutical Preparations

The compounds of the invention will normally be administered via the oral, parenteral, intravenous, intramuscular, subcutaneous or in other injectable ways, buccal, rectal, vaginal, transdermal and/or nasal route and/or via inhalation, in the form of pharmaceutical preparations comprising the active ingredient either as a free acid, or a pharmaceutical acceptable organic or inorganic base addition salt, in a pharmaceutically acceptable dosage form. Depending upon the disorder and patient to be treated and the route of administration, the compositions may be administered at varying doses.

The compounds of the invention may also be combined with other therapeutic agents which are useful in the treatment of disorders associated with the development and progress of atherosclerosis such as hypertension, hyperlipidemias, dyslipidemias, diabetes and obesity.

Suitable daily doses of the compounds of the invention in therapeutical treatment of humans are about 0.0001–100 mg/kg body weight, preferably 0.001–10 mg/kg body weight.

According to a further aspect of the invention there is thus provided a pharmaceutical formulation including any of the compounds of the invention, or pharmaceutically acceptable derivatives thereof, in admixture with pharmaceutically acceptable adjuvants, diluents and/or carriers.

Pharmacological Properties

The present compounds of formula (I) will be adapted for the prophylaxis and/or treatment of clinical conditions associated with reduced sensitivity to insulin (insulin resistance) and associated metabolic disorders. These clinical conditions will include, but will not be limited to, abdominal obesity, arterial hypertension, hyperinsulinaemia, hyperglycaemia, non insulin dependent diabetes mellitus (NIDDM) and the dyslipidaemia characteristically appearing with insulin resistance. This dyslipidaemia, also known as the atherogenic lipoprotein profile of phenotype B, is characterised by moderately elevated non-esterified fatty acids, elevated very low density lipoproteins (VLDL) triglycerides, low high density lipoproteins (HDL) cholesterol and the presence of small, dense, low density lipoproteins (LDL). Treatment with the present compounds is expected to lower the cardiovascular morbidity and mortality associated with atherosclerosis. These cardiovascular disease conditions include macro-angiophaties causing myocardial infarction, cerebrovascular disease and peripheral arterial insufficiency of the lower extremities. Because of their insulin sensitizing effect compounds of formula (1) are also expected to reduce the progress of clinical conditions associated with chronic hyperglycaemia in diabetes like the micro-angiophaties causing renal disease and retinal damage. Furthermore the compounds may be useful in treatment of various conditions outside the cardiovascular system associated with insulin resistance like the polycystic ovarian syndrome.

WORKING EXAMPLES $^1$H NMR and $^{13}$C NMR measurements were performed on a BRUKER ACP 300 or Varian UNITY plus 400, 500 or 600 spectrometers, operating at $^1$H frequencies of 300, 400, 500 and 600 MHz, respectively, and at $^{13}$C frequencies of 75, 100, 125 and 150 MHz, respectively.

Unless otherwise stated, chemical shifts are given in ppm with the solvent as internal standard.

Example 1

2-Ethoxy-3-[4-(2-{4-methanesulfonyloxyphenyl}ethoxy)phenyl] propanoic Acid Ethyl Ester (a) 2-(4-Methanesulfonyloxyphenyl)ethylmethanesulfonate p-Hydroxyphenethyl alcohol (15 g; 0.108 mole) was dissolved in dichloromethane. Triethylamine (27.3 g; 0.27 mole) was added followed by addition of a solution of methanesulphonyl chloride (27.2 g; 0.239 mole) in dichloromethane at 0° C. The reaction mixture was allowed to reach room temperature, then stirred at room temperature and followed by TLC. The reaction mixture was filtered. The filtrate was washed with water, the phases were separated and the organic phase was dried with sodium sulfate and evaporated in vacuo to give 28 g (yield 88%) of 2-(4-methanesulfonyloxyphenyl)ethylmethanesulfonate.

$^1$H-NMR (400 MHz; CDCl$_3$): δ 2.85 (s, 3H), 3.05 (t, 2H), 3.15 (s, 3H), 4.35 (s, 2H), 7.2 (dm, 2H), 7.25 (dm, 2H). $^{13}$C-NMR (100 MHz; CDCl$_3$): δ 34.8, 37.3, 69.6, 122.2, 130.5, 135.8, 148.1.

(b) 4-[2-(4-Formylphenoxy)ethyl]phenylmethanesulfonate 2-(4-Methanesulfonyloxyphenyl)ethylmethanesulfonate (30 g; 0.102 mole) was dissolved in acetonitrile and slowly added to a mixture of p-hydroxybenzaldehyde (31.1 g; 0.255 mole) and potassium carbonate (41.46 g; 0.3 mole) in acetonitrile and refluxed until 2-(4-methanesulfonyloxyphenyl)ethylmethanesulfonate was consumed. The salts were filtered off, the solvent was evaporated in vacuo, dichloromethane was added. The organic phase was washed with water and evaporated. Purification by chromatography on silica gel using dichloromethane as eluant gave 21.6 g (yield 66%) of 4-[2-(4-formylphenoxy)ethyl]phenylmethanesulfonate.

$^1$H-NMR (400 MHz; CDCl$_3$): δ 3.05–3.15 (t, 2H; s, 3H), 4.2 (t, 2H), 6.95 (dm, 2H), 7.2 (dm, 2H), 7.3 (dm, 2H), 7.8 (dm, 2H), 9.8 (s, 1H). $^{13}$C-NMR (100 MHz; CDCl$_3$): δ 37.3, 38.3, 63.4, 116.1, 122.1, 129.2, 130.6, 132.6, 138.1, 147.7, 162.6, 191.7.

(c) 2-Ethoxy-3-{4-[2-(4-methanesulfonyloxyphenyl) ethoxy]phenyl}acrylic Acid Ethyl Ester Tetramethylguanidine (1.73 g; 15.0 mmole) was slowly added to a solution of 4-[2-(4-formylphenoxy)ethyl] phenylmethanesulfonate (4.49 g; 14.0 mmole) and (1,2-diethoxy-2-oxoethyl)(triphenyl)phosphonium chloride (5.62 g; 13.1 mmole) in chloroform (50 ml) at 0° C. After stirring at room temperature overnight the solvent was evaporated in vacuo. When diethyl ether was added to the residue, triphenylphosphine oxide crystallized as white crystals which were filtered off. The filtrate was evaporated in vacuo. The residue was purified by chromatography on silica gel using ethyl acetate in heptane (gradient 1.25–100%) as eluants. The crude product crystallized upon standing. Recrystallization gave 2.18 g (yield 35%) of 2-ethoxy-3-{4-[2-(4-methanesulfonyloxy-phenyl)ethoxy]-phenyl}acrylic acid ethyl ester as white crystals.

$^1$H-NMR (500 MHz; CDCl$_3$): δ 1.34–1.38 (2t, 2x6H, J=7 Hz for both), 3.11 (t, 2H, J=6 Hz), 3.13 (s, 3H), 3.98 (q, 2H, J=7 Hz), 4.2 (t, 2H, J=6.8 Hz), 4.28 (q, 2H, J=7 Hz), 6.87 (dm, 2H, J=9 Hz, unresolved), 6.95 (s, 1H), 7.23 (dm, 2H, J=9 Hz, unresolved), 7.33 (dm, 2H, J=9 Hz, unresolved), 7,73 (dm, 2H, J=9 Hz, unresolved). $^3$C-NMR (125 MHz; CDCl$_3$): δ 14.3, 15.5, 35.0, 37.3, 61.0, 67.5, 68.1, 114.4, 122.0, 123.8, 126.6, 130.5, 131.7, 137.7, 143.1, 147.9, 159.0, 164.9.

(d) 2-Ethoxy-3-[4-(2-{4-methanesulfonyloxy-phenyl}ethoxy)phenyl]propanoic Acid Ethyl Ester 2-Ethoxy-3-{4-[2-(4-methanesulfonyloxyphenyl)ethoxy] phenyl}acrylic acid ethyl ester (1.47 g; 3.38 mmole) was hydrogenated for 3 hours at atmospheric pressure in ethyl acetate (50 ml) using Pd/C (0.74 g, 5%) as catalyst. The reaction mixture was filtered through celite, dried (magnesium sulfate) and the solvent was evaporated in vacuo to give 1.44 g (yield 98%) of 2-ethoxy-3-[4-(2-{4-methanesulfonyloxy-phenyl}ethoxy)phenyl]propanoic acid ethyl ester.

$^1$H-NMR (500 MHz; CDCl$_3$): δ 1.16 (t, 3H, J=7 Hz), 1.23 (t, 3H, J=7 Hz), 2.92–2.96 (m, 2H), 3.09 (t, 2H, J=6.6 Hz), 3.13 (s, 3H), 3.31–3.38 (m, 1H), 3.56–3.63 (m, 1H), 3.94–3.98 (m, 1H), 4.12–4.19 (m, 4H), 6.8 (dm, 2H, J=8.8

Hz, unresolved), 7.14 (dm, 2H, J=8.9 Hz, unresolved), 7.22 (dm, 2H, J=8.9 Hz, unresolved), 7.33 (dm, 2H, J=8.6 Hz, unresolved). $^{13}$C-NMR (125 MHz; CDCl$_3$): δ 14.2, 15.0, 35.1, 37.2, 38.4, 60.7, 66.1, 68.1, 80.3, 114.3, 121.9, 129.5, 130.4, 130.5, 138.0, 147.8, 157.4, 172.5.

Example 2

2-Ethoxy-3-[4-(2-{4-methanesulfonyloxyphenyl}ethoxy)phenyl] propanoic Acid

Lithium hydroxide hydrate (0.12 g; 2.82 mmole) dissolved in water (10 ml) was slowly added to a solution of 2-ethoxy-3-[4-(2-{4-methanesulfonyloxyphenyl}ethoxy) phenyl]propanoic acid ethyl ester (described in Example 1d) (1.12 g; 2.56 mmole) in tetrahydrofuran (30 ml). After stirring at room temperature for 3 hours. Water (50 ml) was added and tetrahydrofuran was removed by evaporation in vacuo. The residue was acidified with hydrochloric acid (2M), and extracted three times with ethyl acetate. The combined organic phases were dried with magnesiumsulfate. Evaporation of the solvent gave 1 g (yield 96%) of 2-ethoxy-3-[4-(2-{4-methanesulfonyloxyphenyl}ethoxy) phenyl]propanoic acid.

$^1$H-NMR (500 MHz; CDCl$_3$): δ 1.17 (t, 3H, J=7 Hz), 2.91–2.99 (m, 1H), 3.03–3.11 (m, 3H), 3.12 (s, 3H), 3.39–3.47 (m, 1H), 3.57–3.64 (m, 1H), 4.01–4.06 (m, 1H), 4.14 (t, 2H, J=6.7 Hz), 6.81 (dm, 2H, J=8.6 Hz, unresolved), 7.15 (dm, 2H, J=8.6 Hz, unresolved), 7.22 (dm, 2H, J=8.6 Hz, unresolved), 7.33 (dm, 2H, J=8.6 Hz, unresolved). $^{13}$C-NMR (125 MHz; CDCl$_3$): δ 15.0, 35.1, 37.2, 37.8, 66.8, 68.1, 79.7, 114.4, 121.9, 128.8, 130.49, 130.52, 137.9, 147.8, 157.5, 169.1.

Example 3

N-Cyano-2-ethoxy-3-[4-(2-{4-methanesulfonyloxyphenyl}ethoxy)phenyl] propanoic Amide DCC (0.444 g; 2.15 mmole) and N-hydroxy-succinimide (0.247 g; 2.15 mmole) were added to a solution of 2-ethoxy-3-[4-(2-{4-methanesulfonyloxyphenyl}ethoxy)phenyl] propanoic acid (described in Example 2) (0.8 g; 1.96 mmole) in acetonitrile (20 ml) at 0° C. After stirring at room temperature overnight a precipitate was filtered off and diisopropylethylamine (1 ml; 5.88 mmole) and cyanamide (0.165 g; 3.92 mmole) were added. After stirring overnight the reaction mixture was poured onto potassium hydrogen sulfate (1M, 20 ml) and the mixture was extracted with ethyl acetate. The organic phase was washed with water, dried (sodium sulfate) and the solvent was evaporated. Chromatography of the crude product on silica gel using ethyl acetate:heptane; acetic acid (10:10:1) as eluant gave 0.755 g (yield 89%) of N-cyano-2-ethoxy-3-[4-(2-{4-methanesulfonyloxy-phenyl}ethoxy)phenyl]propanoic amide.

$^1$H NMR (500 MHz; CD$_3$OD): δ 7.39 (d, J=8.7 Hz, 2H), 7.25 (d, J=8.7 Hz, 2H), 7.14 (d, J=8.6 Hz, 2H), 6.79 (d, J=8.6 Hz, 2H), 4.16 (t, J=6.6 Hz, 2H), 3.79 (dd, J=8.6 Hz and 4.5 Hz, 1H), 3.53 (m, 1H), 3.22 (m, 1H), 3.17 (s, 3H), 3.07 (t, J=6.6 Hz, 2H), 2.86 (dd, J=13.9 Hz and 4.5 Hz, 1H), 2.75 (dd, J=13.9 Hz and 8.6 Hz, 1H), 1.07 (t, J=7.0 Hz, 3H).

Example 4

N-Benzyloxy-2-ethoxy-3-[4-(2-{4-methanesulfonyloxyphenyl}ethoxy)phenyl] propanoic Amide DCC (1 g; 4.85 mmole) and N-hydroxy-succinimide acid (0.56 g; 4.85 mmole) were added to a solution of 2-ethoxy-3-[4-(2-{4-methanesulfonyloxyphenyl}ethoxy)phenyl] propanoic acid (described in Example 2) (1.65 g; 4.04 mmole) in acetonitrile (25 ml) at 0° C. After 1 hour a precipitate was filtered off and diisopropylethylamine (1.82 g; 14.1 mmole) and benzyl hydroxylamine (1.24 g; 8.08 mmole) dissolved in acetonitrile were added. After stirring overnight hydrochloric acid (2M) was added and the mixture was extracted with diethyl ether. The organic phase was washed with sodium carbonate solution and dried (magnesium sulfate). The solvent was removed and the crude product was purified by chromatography on silica gel using ethyl acetate:heptane (gradient 10–100% ethyl acetate) as eluant to give 1.36 g (yield 66%) of N-benzyloxy-2-ethoxy-3-[4-(2-{4-methanesulfonyloxy-phenyl}ethoxy)phenyl]propanoic amide.

$^1$H-NMR (400 MHz; CDCl$_3$): δ 1.01 (t, 3H, J=7.1 Hz), 2.82–2.90 (m, 1H), 3.03–3.11 (m, 3H), 3.12 (s, 3H), 3.36 (q, 2H, J=7.1 Hz), 3.91–3.96 (m, 1H), 4.13 (t, 2H, J=6.8 Hz), 4.76 (d, 1H, J=11.4 Hz), 4.88 (d, 1H, J=11.4 Hz) 6.79 (dm, 2H, J=8.8 Hz, unresolved), 7.12 (dm, 2H, J=8.8 Hz, unresolved), 7.21 (dm, 2H, J=8.8 Hz, unresolved), 7.27–7.36 (m, 7H), 8.69 (s, 1NH). $^{13}$C-NMR (100 MHz; CDCl$_3$): δ 15.0, 35.1, 37.3, 37.8, 66.7, 68.2, 78.3, 81.0, 114.2, 121.9, 128.5, 128.8, 129.17, 129.23, 130.5, 130.8, 135.0, 138.0, 147.8, 157.5, 168.8.

Example 5

2-Ethoxy-3-[4-(2-{4-methanesulfonyloxyphenyl}ethoxy)phenyl] propanoic Amide Ammonia (g) was bubbled through a mixture of 2-ethoxy-3-[4-(2-{4-methanesulfonyloxyphenyl}ethoxy)phenyl] propanoic acid (described in Example 2) (2.9 g; 7.1 mmole) and benzotriazol-1-yl-oxy-tris-pyrrolidino-phosphonium hexafluorophosphate (3.7 g; 7.1 mmole) in DMF (30 ml) for 3 hours at room temperature. Water and ethyl acetate were added. The phases were separated, the organic phase was washed with water, dried with magnesium sulfate and the solvent was evaporated in vacuo. The crude product was crystallized in diethyl ether to give 2.5 g (yield 86%) white powder of 2-ethoxy-3-[4-(2-{4-methanesulfonyl-oxyphenyl}ethoxy)phenyl]propanoic amide.

$^1$H-NMR (300 MHz; CDCl$_3$): δ 1.13 (t, 3H, J=6.8 Hz), 2.80–2.90 (m, 1H), 3.05–3.14 (m, 6H), 3.36–3.56 (m, 2H), 3.84–3.91 (m, 1H), 4.14 (t, 2H, J=6.5 Hz), 5.38 (s br, 1NH), 6.42 (s br, 1NH), 6.80 (dm, 2H, J=8.8 Hz, unresolved), 7.15 (dm, 2H, J=8.8 Hz, unresolved), 7.19–7.27 (m, 2H), 7.34 (dm, 2H, J=8.1 Hz, unresolved). $^{13}$C-NMR (75 MHz; CDCl$_3$): δ 15.2, 35.2, 37.3, 38.0, 66.6, 68.1, 81.4, 114.2, 122.0, 129.7, 130.58, 130.64, 138.0, 147.8, 157.3, 175.2.

Example 6

2-Cyano-3-{4-[2-(4-methanesulfonyloxyphenyl) ethoxy]phenyl}acrylic Acid Ethyl Ester A mixture of 4-[2-(4-formylphenoxy)ethyl] phenylinethanesulfonate (described in Example 1b) (2 g; 6.24 mmole), ethyl cyanoacetate (1.41 g; 12.48 mmole) and sodium acetate (1.34 g; 15.6 mmole) was heated to 120° C. The mixture which melted upon heating was then allowed to cool down. Dichloromethane was added, the solution was washed with water and brine. The organic phase was dried with sodium sulfate, filtered and the solvent evaporated in vacuo. Chromatography of the crude product on silica gel using heptane:ethyl acetate (gradient 9:1 to 1:1) as eluant followed by crystallization gave 1.98 g (yield 77%) of 2-cyano-3-{4-[2-(4-methanesulfonyloxyphenyl)ethoxy]phenyl}acrylic acid ethyl ester.

$^1$H-NMR (400 MHz; CDCl$_3$): δ 1.37 (t, 3H, J=7.1 Hz), 3.13 (t, 2H, J=6.8 Hz), 3.13 (s, 3H), 4.24 (t, 2H, J=6.8 Hz), 4.35 (q, 2H, J=7.1 Hz), 6.95 (dm, 2H, J=9 Hz, unresolved), 7.23 (dm, 2H, J=9 Hz, unresolved), 7.32 (dm, 2H, J=9 Hz, unresolved), 7.97 (dm, 2H, J=9 Hz, unresolved), 8.15 (s, 1H). $^{13}$C-NMR (100 MHz; CDCl$_3$): δ 14.2, 34.9, 37.4, 62.4, 68.6, 99.6, 115.2, 116.1, 122.1, 124.6, 130.5, 133.6, 137.3, 148.0, 154.3, 162.8, 163.1.

Example 7

2-Cyano-3-{4-[2-(4-methanesulfonyloxyphenyl)ethoxy]phenyl}propanoic Acid Ethyl Ester A mixture of 2-cyano-3-{4-[2-(4-methanesulfonyloxyphenyl)ethoxy]phenyl}acrylic acid ethyl ester (described in Example 6) (1.69 g; 4.07 mmole) and diethyl-1,4-dihydro-2,6-dimethyl-3,5-pyridine dicarboxylate (2.06 g; 8.14 mmole) was slowly heated to more than 190° C. under vacuum and thereafter allowed to cool to room temperature. The crude product was purified by chromatography on silica gel using heptane:ethyl acetate (gradient 2:1 to 1:1) as eluant to give 1.55 g (yield 91%) of 2-cyano-3-{4-[2-(4-methanesulfonyloxyphenyl)ethoxy]phenyl}propanoic acid ethyl ester.

$^1$H-NMR (400 MHz; CDCl$_3$): δ 1.17 (t, 3H, J=7 Hz), 2.96–3.16 (m, 6H), 3.66–3.72 (m, 1H), 4.05 (t, 2H, J=6.8 Hz), 4.13 (q, 2H, J=7 Hz), 6.73 (dm, 2H, J=8.5 Hz, unresolved), 7.09–7.19 (m, 4H), 7.25 (dm, 2H, J=8.5 Hz, unresolved). $^{13}$C-NMR (100 MHz; CDCl$_3$): δ 13.4, 34.3, 34.5, 36.7, 39.3, 114.3, 116.0, 121.5, 127.2, 129.6, 130.1, 137.4, 147.5, 157.7, 165.2.

Example 8

2-Cyano-3-{4-[2-(4-methanesulfonyloxyphenyl)ethoxy]phenyl}propanoic Acid

A mixture of 2-cyano-3-{4-[2-(4-methanesulfonyloxyphenyl)ethoxy]phenyl}propanoic acid ethyl ester (described in Example 7) (0.9 g; 2.16 mmole), lithium hydroxide hydrate (0.12 g; 2.86 mmole), methanol (5 ml), water (5 ml) and tetrahydrofuran (10 ml) was stirred for 30 minutes at room temperature. Water was added and the mixture was washed with diethyl ether. The water phase was acidified with hydrochloric acid and extracted with ethyl acetate. The organic phase was dried (sodium sulfate), filtered and evaporated in vacuo. The crude product was purified by crystallization in diisopropyl ether to give 0.56 g (yield 67%) of 2-cyano-3-{4-[2-(4-methanesulfonyloxyphenyl)ethoxy]phenyl}propanoic acid.

$^1$H-NMR (500 MHz; CDCl$_3$): δ 3.02–3.3 (m, 7H), 3.7–3.8 (m, 1H), 4.15 (t, 2H, J=6.7 Hz), 6.8–6.9 (m, 2H), 7.15–7.27 (m, 4H), 7.27–7.4 (m, 2H), 8.67 (s, 1H, OH). $^{13}$C-NMR (100 MHz; CDCl$_3$): δ 34.8, 35.0, 37.3, 39.9, 68.2, 114.9, 115.6, 122.0, 127.0, 130.2, 130.6, 137.8, 147.8, 158.3, 170.0.

Example 9

2-Cyano-3-{4-[2-(4-methanesulfonyloxyphenyl)ethoxy]phenyl}acrylic Acid

2-Cyano-3-{4-[2-(4-methanesulfonyloxyphenyl)ethoxy]phenyl}acrylic acid ethyl ester (described in Example 6) (0.201 g; 0.483 mmole), lithium hydroxide (0.04 g; 1.67 mmole), methanol (2.3 ml) and water (2.3 ml) was stirred at 40° C. for 23 hours. More water was added, methanol was removed by evaporation in vacuo and the mixture was acidified using potassium hydrogen sulfate. The mixture was extracted with ethyl acetate and the organic phase was dried (sodium sulfate), filtered and evaporated in vacuo. The crude products were purified on preparative HPLC using acetonitrile (gradient 30–60%): ammonium acetate (0.1 M). The fractions were acidified with potassium hydrogen sulfate and then extracted with ethyl acetate. The organic phases were combined and evaporated in vacuo to give 7 mg of 2-cyano-3-{4-[2-(4-methanesulfonyloxyphenyl)ethoxy]phenyl}acrylic acid and 21,8 mg of 2-cyano-3-{4-[2-(4-hydroxyphenyl)ethoxy]phenyl}-acrylic acid.

$^1$H-NM (400 MHz; CDCl$_3$): δ 3.11 (t, 2H, J=6.8 Hz), 3.12 (s, 3H), 4.23 (t, 2H, J=6.8 Hz), 6.94 (dm, 2H, J=9 Hz, unresolved), 7.22 (dm, 2H, J=8.5 Hz, unresolved), 7.31 (dm, 2H, J=8.5 Hz, unresolved), 7.95 (dm, 2H, J=9 Hz, unresolved), 8.13 (s, 1H). $^{13}$C-NMR (100 MHz; CDCl$_3$): δ 34.9, 37.4, 68.6, 99.6, 115.2, 116.3, 122.1, 124.5, 130.5, 133.6, 137.3, 148.0, 154.7, 162.8, 164.9.

Example 10

2-{4-[2-(4-Methanesulfonyloxyphenyl)ethoxy]benzylidene}malonic Acid Dimethyl Ester A solution of titanium tetrachloride (4.82 g; 25.4 mmole) and carbon tetrachloride (6.35 ml) was added to dry tetrahydrofuran (50.8 ml) at 0° C. under argon. To the mixture was added a solution of 4-[2-(4-formylphenoxy)ethyl]phenylmethanesulfonate (described in Example 1b) (4.07 g; 12.7 mmole) in dry tetrahydrofuran (6.35 ml) and then dimethyl malonate (1.68 ml, 12.7 mmole). Finally pyridine (4.02 g; 50.8 mmole) in tetrahydrofuran (8.9 ml) was added during 3 hours. The reaction mixture was stirred at room temperature for 15 hours. Water was added and the mixture was extracted with a mixture of diethyl ether and ethyl acetate. The organic phase was washed with water and the water phase was extracted with dichloromethane. The organic phases were combined, dried (sodium sulfate), filtered and evaporated in vacuo to give 5.34 g (yield 97%) of 2-{4-[2-(4-methanesulfonyloxyphenyl)ethoxy]benzylidene}malonic acid dimethyl ester.

$^1$H-NMR (400 MHz; CDCl$_3$): δ 3.12 (t, 2H, J=7), 3.14 (s, 3H), 3.84 (s, 3H), 3.87 (s, 3H), 4.2 (t, 2H, J=7 Hz), 6.9 (dm, 2H, J=9 Hz, unresolved), 7.24 (dm, 2H, J=9 Hz, unresolved), 7.31–7.41 (m, 4H), 7.7 (s, 1H). $^{13}$C-NMR (100 MHz; CDCl$_3$): δ 34.9, 37.3, 52.5, 52,6, 68.3, 114.9, 122.0, 122.9, 125.4, 130.5, 131.5, 137.5, 142.4, 147.9, 160.7, 164.8, 167.5.

Example 11

2-{4-[2-(4-Methanesulfonyloxyphenyl)ethoxy]benzyl}malonic Acid Dimethyl Ester

2-{4-[2-(4-Methanesulfonyloxyphenyl)ethoxy]benzylidene}malonic acid dimethyl ester (described in Example 10) (2.31 g; 5.32 mmole) was hydrogenated for 2.5 hours at atmospheric pressure in ethyl acetate (140 ml) and acetic acid (5 ml) using Pd/C (0.8 g) as catalyst and then filtered through hyflo. The solvent was evaporated in vacuo, dichloromethane and diluted sodium bicarbonate solution were added and the phases were separated. The organic phase was washed with brine, dried (sodium sulfate), filtered and evaporated in vacuo to give 2.35 g (yield 100%) of 2-{4-[2-(4-methanesulfonyloxyphenyl)ethoxy]benzyl}malonic acid dimethyl ester.

¹H-NMR (400 MHz; CDCl₃): δ 3.10 (t, 2H, J=6.6 Hz), 3.14 (s, 3H), 3.17 (d, 2H, J=7.6 Hz), 3.64 (t, 1H, J=7.6), 3.71 (s, 6H), 4.15 (t, 2H, J=6.6 Hz), 6.81 (dm, 2H, J=8.8 Hz, unresolved), 7.11 (dm, 2H, J=8.8 Hz, unresolved), 7.24 (dm, 2H, J=8.8 Hz, unresolved), 7.34 (dm, 2H, J=8.8 Hz, unresolved). ¹³C-NMR (100 MHz; CDCl₃): δ 33.9, 35.1, 36.0, 37.3, 52.5, 53.8, 68.2, 114.6, 121.9, 129.8, 130.0, 130.5, 137.9, 147.9, 157.5, 169.2.

Example 12

2-Ethoxy-3-{3-[3-(4-methanesulfonyloxyphenyl)propoxy]phenyl}propanoic Acid Ethyl Ester (a) 3-(3-Benzyloxyphenyl)-2-ethoxyacrylic Acid Ethyl Ester Tetramethylguanidine (6.5 g; 56.6 mmole) was slowly added to a solution of 3-benzyloxybenzaldehyde (11.7 g; 55 mmole) and (1,2-diethoxy-2-oxoethyl)(triphenyl) phosphonium chloride (20.1 g; 46.8 mmole) in dichloromethane (200 ml) at 0° C. After stirring at room temperature overnight the solvent was evaporated in vacuo. Diethyl ether was added and insoluble material was filtered off. The filtrate was washed with sodium bicarbonate solution, dried (magnesium sulfate), filtered and the solvent was evaporated in vacuo. The residue was purified by chromatography on silica gel using tetrahydrofuran (0.5%) in dichloromethane as eluant. The remaining aldehyde was removed by stirring with sodium bisulfite in water and diethyl ether for 2 days. The phases were separated and the organic phase was evaporated in vacuo to give 10.5 g (yield 69%) of 3-(3-benzyloxyphenyl)-2-ethoxyacrylic acid ethyl ester.

¹H-NMR (300 MHz; CDCl₃): δ 1,4 (m, 6H), 4.02 (q, 2H), 4.32 (q, 2H), 5.12 (s, 2H), 6.97 (unresolved, 2H), 7.3–7.5 (m, 7H), 7.7 (unresolved, 1H). ¹³C-NMR (75 MHz; CDCl₃): δ 14.3, 15.6, 61.2, 67.7, 69.9, 115.6, 116.1, 123.2, 123.7, 127.4, 128.0, 128.6, 129.4, 135.0, 137.0, 144.9, 158.8, 164.6.

(b) 2-Ethoxy-3-(3-hydroxyphenyl)propanoic Acid Ethyl Ester 3-(3-Benzyloxyphenyl)-2-ethoxyacrylic acid ethyl ester (10.4 g; 31.8 mmole) was hydrogenated at atmospheric pressure in ethyl acetate using Pd/C (dry, 10%) as catalyst. The reaction mixture was filtered through celite and the solvent was evaporated in vacuo. The starting material was not completely consumed, therefor the hydrogenation was repeated to give 7 g (yield 92%) of 2-ethoxy-3-(3-hydroxyphenyl)propanoic acid ethyl ester.

¹H-NMR (300 MHz; CDCl₃): δ 1.15 (t, 3H), 1.22 (t, 3H), 2.95 (m, 2H), 3.4 (m, 1H), 3,6 (m, 1H), 4.05 (m, 1H), 4.15 (q, 2H). ¹³C-NMR (75 MHz; CDCl₃): δ 14.1, 15.0, 39.2, 61.2, 66.4, 80.2, 113.9, 116.5, 121.2, 129.4, 137.2, 138.5, 156.0.

(c) 3-(4-Methanesulfonyloxyphenyl)propylmethanesulfonate 3-(4-Methanesulfonyloxyphenyl)propylmethanesulfonate was synthesized using the same method as in Example 1a from 3-(4-hydroxyphenyl)-1-propanol.

¹H-NMR (400 MHz; CDCl₃): δ 2.1 (q, 2H), 2.8 (t, 2H), 3.0 (s, 3H), 3.15 (s, 3H), 4.25 (t, 2H), 7.23–7.27 (m, 4H). ¹³C-NMR (100 MHz; CDCl₃): δ 31.7, 32.1, 38.4, 38.5, 69.8, 123.2, 131.1, 140.9, 148.7.

(d) 2-Ethoxy-3-{3-[3-(4-methanesulfonyloxyphenyl)propoxy]phenyl}propanoic Acid Ethyl Ester 3-(4-Methanesulfonyloxyphenyl)propylmethanesulfonate (1.905 g; 6.18 mmole) dissolved in acetonitrile (13 ml) was added dropwise to a mixture of 2-ethoxy-3-(3-hydroxyphenyl)propanoic acid ethyl ester (1.47 g; 6.18 mmole) and potassium carbonate (2.56 g; 18.54 mmole) in acetonitrile (15 ml). The mixture was refluxed for 5 hours, then the solvent was evaporated in vacuo and water was added. The mixture was extracted twice with dichloromethane, dried (sodium sulfate), filtered and the solvent was evaporated in vacuo. Purification by chromatography on silica gel using diethyl ether/petroleum ether (gradient 33% to 100% diethyl ether) gave 1.80 g (yield 65%) of 2-ethoxy-3-{3-[3-(4-methanesulfonyloxyphenyl)propoxy]phenyl}propanoic acid ethyl ester.

¹H-NMR (400 MHz; CDCl₃): δ 1.17 (t, 3H, J=7 Hz), 1.24 (t, 3H, J=7.3 Hz), 2.05–2.14 (m, 2H), 2.84 (t, 2H, J=7.5 Hz), 2.97–3.01, (m, 2H), 3.14 (s, 3H), 3.33–3.42 (m, 1H), 3.58–3.66 (m, 1H), 3.96 (t, 2H, J=6 Hz), 4.0–4.05 (m, 1H), 4.15–4.23 (m, 2H), 6.74–6.87 (m, 3H), 7.17–7.24 (m, 3H), 7.25–7.30 (m, 2H). ¹³C-NMR (100 MHz; CDCl₃): δ 14.2, 15.0, 30.7, 31.6, 37.2, 39.4, 60.8, 66.2, 66.5, 80.1, 112.8, 115.6, 121.8, 121.9, 129.2, 130.0, 138.8, 141.0, 147.4, 158.8, 172.4.

Example 13

2-Ethoxy-3-[3-(3-{4-methanesulfonyloxyphenyl}propoxy)phenyl]propanoic Acid

Lithium hydroxide hydrate (91.1 mg; 2.7 mmole) in water (6.6 ml) was slowly added to a solution of 2-ethoxy-3-{3-[3-(4-methanesulfonyloxyphenyl)propoxy]phenyl}propanoic acid ethyl ester (described in Example 12d) (0.889 g; 1.97 mmole) in tetrahydrofuran (9 ml). After stirring at room temperature for 5 hours tetrahydrofuran was removed by evaporation in vacuo. The residue was washed with diethyl ether and ethyl acetate. The water phase was acidified with potassium hydrogen sulfate (1M), and extracted with ethyl acetate and dichloromethane. The organic phases were combined, dried (sodium sulfate), filtered and the solvent was evaporated in vacuo to give 0.91 g of 2-ethoxy-3-[3-(3-{4-methanesulfonyloxyphenyl}propoxy)phenyl]propanoic acid.

¹H-NMR (400 MHz; CDCl₃): δ 1.20 (t, 3H, J=7.1 Hz), 2.05–2.15 (m, 2H), 2.84 (t, 2H, J=7.6 Hz), 2.95–3.03, (m, 1H), 3.11–3.17 (m, 4H), 3.46–3.65 (m, 2H), 3.95 (t, 2H, J=6.1 Hz), 4.09–4.14 (m, 1H), 6.77–6.81 (m, 2H), 6.82 (dm, 1H, J=7.81 Hz, unresolved), 7.19–7.29 (m, 5H). ¹³C-NMR (100 MHz; CDCl₃): δ 15.0, 30.7, 31.6, 37.3, 38.6, 66.5, 67.0, 79.5, 113.0, 115.6, 121.88, 121.90, 129.4, 130.0, 138.0, 141.0, 147.4, 158.9, 173.9.

Example 14

3-{4-[2-(4-Methanesulfonyloxyphenyl)ethoxy]phenyl}-2-methoxypropanoic Acid Methyl Ester (a) 3-(4-Benzyloxyphenyl)-2-methoxypropanoic Acid Methyl Ester Silver(I)oxide (2.43 g; 10.5 mmole), molecular sieves (4 Å, 2 g) and methyl iodide (2.97 g; 20.9 mmole) were added to a solution of 3-(4-benzyloxyphenyl)-2-hydroxypropanoic acid methyl ester (2.0 g; 6.98 mmole) in dry dichloromethane (20 ml). The reaction mixture was refluxed for 72 hours, filtered through celite and washed with water. The organic phase was dried with magnesium sulfate and evaporated in vacuo to give 1.93 g (yield 92%) of an oil of 3-(4-benzyloxyphenyl)-2-methoxypropanoic acid methyl ester.

¹H-NMR (500 MHz; CDCl₃): δ 2.90–3.01 (m, 2H), 3.35 (s, 3H), 3,71 (s, 3H), 3.91–3.96 (m, 1H), 5.04 (s, 2H), 6.90 (dm, 2H, J=8.6 Hz, unresolved), 7.13 (dm, 2H, J=8.6 Hz, unresolved), 7.29–7.35 (m, 1H), 7.35–7.40 (m, 2H), 7.40–7.43 (m, 2H).

(b) 3-(4-Hydroxyphenyl)-2-methoxypropanoic Acid Methyl Ester 3-(4-Benzyloxyphenyl)-2-methoxypropanoic acid methyl ester (1.91 g; 6.36 mmole) was hydrogenated in methanol (30 ml) using Pd/C (5%, wet, 0.9 g) as catalyst. The mixture was filtered through celite and the filtrate was evaporated in vacuo to give 1.16 g (yield 87%) of 3-(4-hydroxyphenyl)-2-methoxypropanoic acid methyl ester.

$^1$H-NMR (500 MHz; CDCl$_3$): δ 2.93–3.03 (m, 2H), 3.38 (s, 3H), 3,75 (s, 3H), 3.94–3.99 (m, 1H), 5.02–5.12 (s br, 1 OH), 6.77 (dm, 2H, J=8.3 Hz, unresolved), 7.11 (dm, 2H, J=8.3 Hz, unresolved).

(c) 3-{4-[2-(4-Methanesulfonyloxyphenyl)ethoxy]phenyl}-2-methoxypropanoic Acid Methyl Ester 3-(4-Hydroxyphenyl)-2-methoxypropanoic acid methyl ester was alkylated with 2-(4-methanesulfonyloxyphenyl) ethylmethanesulfonate (described in Example 1a) using the same method as in Example 1 (b) to give 3-{4-[2-(4-methanesulfonyloxyphenyl)ethoxy]-phenyl}-2-methoxypropanoic acid methyl ester.

$^1$H-NMR (500 MHz; CDCl$_3$): δ 2.9–3.0 (m, 2H), 3.09 (t, 2H, J=6.7 Hz), 3.13 (s, 3H), 3.34 (s, 3H), 3.72 (s, 3H), 3.90–3.95 (m, 1H), 4.14 (t, 2H, J=6.7 Hz), 6.80 (dm, 2H, J=8.6 Hz, unresolved), 7.11 (dm, 2H, J=8.6 Hz, unresolved), 7.22 (dm, 2H, J=8.6 Hz, unresolved), 7.33 (dm, 2H, J=8.6 Hz, unresolved).

Example 15

3-{4-[2-(4-Methanesulfonyloxyphenyl)ethoxy] phenyl}-2-methoxypropanoic Acid

3-{4-[(4-Methanesulfonyloxyphenyl)ethoxy]phenyl}-2-methoxypropanoic acid methyl ester (described in Example 14) was hydrolyzed using the same method as in Example 2 to give 3-{4-[2-(4-methane-sulfonyloxyphenyl)ethoxy] phenyl}-2-methoxypropanoic acid $^1$H-NMR (500 MHz; CDCl$_3$): δ 2.91–2.99 (m, 1H), 3.03–3.10 (m, 3H), 3.11 (s, 3H), 3.37 (s, 3H), 3.94–3.99 (m, 1H), 4.13 (t, 2H), 6.81 (dm, 2H, J=8.3 Hz, unresolved), 7.15 (dm, 2H, J=8.3 Hz, unresolved), 7.21 (dm, 2H, J=8.3 Hz, unresolved), 7.32 (dm, 2H, J=8.3 Hz, unresolved), 9.36 (bs, 1H). $^{13}$C-NMR (100 MHz; CDCl$_3$): δ 35.0, 37.1, 37.7, 58.5, 68.1, 81.2, 114.4, 121.9, 128.7, 130.3, 130.5, 137.9, 147.8, 157.5, 176.3.

Example 16

2-Hexyloxy-3-[4-(2-{4-methanesulfonyloxyphenyl}ethoxy)phenyl] propanoic Acid Methyl Ester (a) 3-(4-Benzyloxyphenyl)-2-hexyloxypropanoic Acid Methyl Ester 3-(4-Benzyloxyphenyl)-2-hydroxypropanoic acid methyl ester (0.4243 g; 1.482 mmole) was dissolved in dry dichloromethane (10 ml). Silver (I) oxide (1.717 g; 7.41 mmole) was added, followed by slow addition of hexyl iodide (0.943 g; 4.45 mmole). The reaction mixture was stirred at room temperature for 3 hours then molecular sieves (3 Å) was added and the reaction mixture was stirred for 4 more days and then filtered. The solvent was evaporated and evacuation at 60° C. for 5 hours gave 0.48 g (87% yield) of 3-(4-benzyloxyphenyl)-2-hexyloxypropanoic acid methyl ester.

$^1$H-NMR (400 MHz; CDCl$_3$): δ 0.88 (t, 3H), 1.18–1.34 (m, 6H), 1.47–1.60 (m, 2H), 2.91–3.10 (m, 2H), 3.22-3-29 (m, 1H), 3.52–3.59 (m, 1H), 3.72 (s, 3H), 3.95–4.02 (m, 1H), 5.05 (s, 2H), 6.91 (dm, 2H, J=8.8 Hz, unresolved), 7.16 (dm, 2H, J=8.8 Hz, unresolved), 7.30–7.46 (m, 5H). $^{13}$C-NMR (100 MHz; CDCl$_3$): δ 14,0, 22.6, 25.6, 29.5, 31.5, 38.5, 51.8, 70.0, 71.0, 80.6, 114.6, 127.5, 127.9, 128.5, 129.6, 130.4, 137.1, 157.6, 173.0.

(b) 2-Hexyloxy-3-(4-hydroxyphenyl)propanoic Acid Methyl Ester

2-Hexyloxy-3-(4-hydroxyphenyl)propanoic acid methyl ester was prepared from 3-(4-benzyloxyphenyl)-2-hexyloxypropanoic acid methyl ester in ethyl acetate using the same method as described in Example 14b.

$^1$H-NMR (400 MHz; CDCl$_3$): δ 0.87 (t, 3H), 1.17–1.33 (m, 6H), 1.46–1.58 (m, 2H), 2.89–3.0 (m, 2H), 3.21-3-30 (m, 1H), 3.51–3.59 (m, 1H), 3.72 (s, 3H), 3.94–4.0 (m, 1H), 6.75 (dm, 2H, J=8.8 Hz, unresolved), 7.10 (dm, 2H, J=8.8 Hz, unresolved), 7.27 (bs, 1H, OH). $^{13}$C-NMR (100 MHz; CDCl$_3$): δ 14,0, 22.6, 25.6, 29.5, 31.5, 38.5, 51.8, 71.0, 80.6, 115.1, 129.3, 130.6, 154.3, 173.1.

(c) 2-Hexyloxy-3-[4-(2-{4-methanesulfonyloxyphenyl}ethoxy)phenyl]propanoic Acid Methyl Ester 2-Hexyloxy-3-(4-hydroxyphenyl)propanoic acid methyl ester (0.33 g, 1.19 mmole) and 2-(4-methanesulfonyloxyphenyl)ethanol (0.2578 g; 1.19 mmole) was dissolved in dichloromethane (5 ml) under argon. Azodicarbonyl dipiperidine (0.451 g; 1.789 mmole) was added followed by addition of triphenylphosphine (0.375 g; 1.423 mmole). The reaction mixture was stirred at room temperature and after 2 hours more dichloromethane (2 ml) was added. The reaction mixture was stirred for another 18 hours and then filtered. The filtrate was washed with water, sodium hydrogen carbonate solution, diluted potassium hydrogen sulfate solution and brine, dried with sodium sulfate and evaporated. Chromatography of the residue on silica gel using heptane:ethyl acetat (2:1 to 1:1) as eluant gave 0.381 g (67% yield) of 2-hexyloxy-3-[4-(2-{4-methanesulfonyloxyphenyl}-ethoxy)phenyl]propanoic acid methyl ester.

$^1$H-NMR (400 MHz; CDCl$_3$): δ 0.86 (t, 3H), 1.16–1.32 (m, 6H), 1.46–1.58 (m, 2H), 2.90–3.01 (m, 2H), 3.10 (t, 2H, J=6.8 Hz), 3.14 (s, 3H), 3.21–3.28 (m, 1H), 3.51–3.58 (m, 1H), 3.72 (s, 3H), 3.95–4.0 (m, 1H), 4.15 (t, 2H, J=6.8 Hz), 6.81 (dm, 2H, J=8.8 Hz, unresolved), 7.14 (dm, 2H, J=8.8 Hz, unresolved), 7.24 (dm, 2H, J=8.3 Hz, unresolved), 7.35 (dm, 2H, J=8.3 Hz, unresolved). $^{13}$C-NMR (100 MHz; CDCl$_3$): δ 14,0, 22.5, 25.5, 29.5, 31.5, 35.1, 37.2, 38.4, 51.7, 68.1, 70.9, 80.5, 114.3, 121.9, 129.5, 130.4, 130.5, 137.9, 147.8, 157.4, 172.9.

Example 17

2-Hexyloxy-3-[4-(2-{4-methanesulfonyloxyphenyl}ethoxy)phenyl] propanoic Acid

Lithium hydroxide hydrate (0.036 g; 0.85 mmole) dissolved in water (2.6 ml) was slowly added at room temperature to a solution of 2-hexyloxy-3-[4-(2-{4-methanesulfonyloxyphenyl}ethoxy)phenyl]propanoic acid methyl ester (described in Example 16) (0.37 g; 0.77 mmole) in tetrahydrofuran (3.5 ml). The reaction mixture was stirred at room temperature for 3.5 hours and then evaporated to remove tetrahydrofuran. The residue was acidified with potassium hydrogen sulfate (1 M) until pH<2 and then extracted with ethyl acetate. The organic phase was washed with brine and dried. Evaporation to remove the solvent gave 0.349 g (97.5%) of 2-hexyloxy-3-[4-(2-{4-methanesulfonyloxyphenyl}-ethoxy)phenyl]propanoic acid.

$^1$H-NMR (400 MHz; CDCl$_3$): δ 0.88 (t, 3H, J=6.8 Hz), 1.18–1.34 (m, 6H), 1.48–1.60 (m, 2H), 2.94–2.97 (m, 1H), 3.06–3.13 (m, 3H), 3.14 (s, 3H), 3.36–3.43 (m, 1H), 3.50–3.57 (m, 1H), 4.02–4.07 (m, 1H), 4.16 (t, 2H, J=6.5

Hz), 6.82 (dm, 2H, J=8.8 Hz, unresolved), 7.15 (dm, 2H, J=8.8 Hz, unresolved), 7.24 (dm, 2H, J=8.3 Hz, unresolved), 7.35 (dm, 2H, J=8.3 Hz, unresolved). $^{13}$C-NMR (100 MHz; CDCl$_3$): δ 13.9, 22.4, 25.4, 29.3, 31.4, 35.0, 37.1, 37.8, 68.0, 71.2, 79.9, 114.2, 121.8, 129.0, 130.4, 130.42, 137.8, 147.8, 157.4, 176.5.

Example 18

2-Ethoxy-3-{4-[2-(3-methanesulfonyloxyphenyl) ethoxy]phenyl}propanoic Acid Ethyl Ester (a) 2-(3-Methanesulfonyloxyphenyl)ethylmethanesulfonate Methanesulfonyl chloride (9.09 g; 79.6 mmole) was slowly added to a solution of 3-hydroxyphenethyl alcohol (5 g; 36.2 mmole) and triethylamine (12.5 ml; 90.5 mmole) in dichloromethane at −10° C. The reaction mixture was stirred over night at room temperature and then the solid material was filtered off. The filtrate was washed with sodium bicarbonate solution and brine, dried (magnesium sulfate) and the solvent was evaporated in vacuo to give 9.3 g (yield 87%) of 2-(3-methanesulfonyloxyphenyl)-ethylmethanesulfonate.

(b) 2-Ethoxy-3-{4-[2-(3-methanesulfonyloxyphenyl) ethoxy]phenyl}propanoic Acid Ethyl Ester 2-Ethoxy-3-{4-[2-(3-methanesulfonyloxyphenyl)ethoxy] phenyl}propanoic acid ethyl ester was synthesized using the same method as in example 1(b) from 2-ethoxy-3-(4-hydroxyphenyl)propanoic acid ethyl ester (described in Example 20b) and 2-(3-methanesulfonyloxyphenyl)-ethylmethanesulfonate.

Example 19

2-Ethoxy-3-{4-[2-(3-methanesulfonyloxyphenyl) ethoxy]phenyl}propanoic Acid

2-Ethoxy-3-{4-[2-(3-methanesulfonyloxyphenyl)ethoxy] phenyl}propanoic acid was synthesized from 2-ethoxy-3-{4-[2-(3-methanesulfonyloxyphenyl)ethoxy] phenyl}propanoic acid ethyl ester (described in Example 18) using the same method as in example 2.

$^1$H NMR (400 MHz; CDCl$_3$): δ 7.34 (m, 1H), 7.24 (m, 2H), 7.15 (m, 3H), 6.81 (d, J=8.6 Hz, 2H), 4.16 (t, J=6.7 Hz, 2H), 4.03 (dd, J=7.7 and 4.3 Hz, 1H), 3.61 (m, 1H), 3.42 (m, 1H), 3.12 (s, 3H), 3.10 (t, J=6.7 Hz, 2H), 3.05 (dd, J=14.2 and 4.3 Hz, 1H), 2.94 (dd, J=14.2 and 7.7 Hz, 1H), 1.16 (t, J=7.0 Hz, 3H). $^{13}$C NMR (100 MHz; CDCl$_3$): δ 174.7, 157.5, 149.3, 141.1, 130.5, 129.9, 128.8, 128.0, 122.6, 119.9, 114.4, 79.7, 68.0, 66.8, 37.7, 37.3, 35.4, 15.0.

Example 20

2-Ethoxy-3-{4-[2-(2-methanesulfonyloxyphenyl) ethoxy]phenyl}propanoic Acid Ethyl Ester (a) 2-(2-Methanesulfonyloxyphenyl)ethylmethanesulfonate Methanesulfonyl chloride (9 g; 79 mmole) was slowly added to a solution of 2-(2-hydroxyphenyl)ethanol (5 g; 36 mmole) and triethylamine (7.99 g; 79 mmole) in dichloromethane at 10° C. The reaction mixture was allowed to reach room temperature and then poured onto a mixture of hydrochloric acid and ice. The phases were separated and the organic phase was washed with brine, dried and the solvent was evaporated. The residue crystallized upon standing to give 9.4 g (yield 89%) of 2-(2-methanesulfonyloxyphenyl)ethylmethanesulfonate.

$^1$H NMR (300 MHz; CDCl$_3$): δ 2.85 (s, 3H), 3.15 (t, 2H), 3.25 (s, 3H), 4.4 (t, 2H), 7.2–7.35 (m, 4H). $^{13}$C NMR (100 MHz; CDCl$_3$): δ 30.3, 37.2, 38.5, 69.0, 122.4, 127.6, 128.8, 129.6, 131.8, 147.5.

(b) 2-Ethoxy-3-(4-hydroxyphenyl)propanoic Acid Ethyl Ester 3-(4-Benzyloxyphenyl)-2-ethoxyacrylic acid ethyl ester (described in Example 38a) (62 g; 0.19 mole) was hydrogenated in ethyl acetate (400 ml) at atmospheric pressure using Pd/C (10%) as catalyst. The mixture was filtered through celite and evaporated in vacuo to give 45.6 g (yield 100%) of 2-ethoxy-3-(4-hydroxyphenyl)propanoic acid ethyl ester.

$^1$H-NMR (600 MHz; CDCl$_3$): δ 1.17 (t, 3H, J=7 Hz), 1.23 (t, 3H, J=7 Hz), 2.95 (d, 2H, J=6.6 Hz), 3.35–3.42 (m, 1H), 3.58–3.64 (m, 1H), 4.0 (t, 1H, J=6.6 Hz), 4.17 (q, 2H, J=7 Hz), 5.97 (s, 1 OH), 6.74 (dm, 2H, J=8.5 Hz, unresolved), 7.08 (dm, 2H, J=8.5 Hz, unresolved). $^{13}$C-NMR (125 MHz; CDCl$_3$): δ 14.0, 14.8, 38.3, 61.0, 66.1, 80.3, 115.1, 128.2, 130.3, 154.8, 173.0.

c) 2-Ethoxy-3-{4-[2-(2-methanesulfonyloxyphenyl)ethoxy] phenyl}propanoic Acid Ethyl Ester 2-Ethoxy-3-(4-hydroxyphenyl)propanoic acid ethyl ester was alkylated with 2-(2-methanesulfonyloxyphenyl) ethylmethanesulfonate using the same method as in Example 1 (b) to give 2-ethoxy-3-{4-[2-(2-methanesulfonyloxyphenyl)ethoxy]phenyl}propanoic acid ethyl ester.

$^1$H NMR(300 MHz; CDCl$_3$): δ 1.2 (2xt, 6H) 2.85 (d, 2H), 3.07 (m, 2H), 3.15 (s, 3H), 3.25–3.38 (m, 1H), 3.5–3.65 (m, 1H), 3.9–4.0 (m, 1H), 4.15 (m, 2H); 6.77 (d, 2H), 7.1–7.45 (unresolved m, 6H).

Example 21

2-Ethoxy-3-{4-[2-(2-methanesulfonyloxyphenyl) ethoxy]phenyl}propanoic Acid

2-Ethoxy-3-{4-[2-(2-methanesulfonyloxyphenyl)ethoxy] phenyl}propanoic acid ethyl ester (described in Example 20) was hydrolyzed using the same method as in Example 2 to give 2-ethoxy-3-{4-[2-(2-methanesulfonyloxyphenyl) ethoxy]phenyl}propanoic acid.

$^1$H NMR (400 MHz; CDCl$_3$): δ 7.41 (m, 1H), 7.35 (m, 1H), 7.27 (m, 2H), 7.15 (d, J=8.4 Hz, 2H), 6.82 (d, J=8.4 Hz, 2H), 4.19 (t, J=6.8 Hz, 2H), 4.03 (dd, J=7.7 and 4.3 Hz, 1H), 3.60 (m, 1H), 3.42 (m, 1H), 3.19 (s, 3H), 3.18 (t, J=6.8 Hz, 2H), 3.06 (dd, J=14.2 and 4.3 Hz, 1H), 2.94 (dd, J=14.2 and 7.7 Hz, 1H), 1.6 (t, J=7.0 Hz, 3H). $^{13}$C NMR (100 MHz; CDCl$_3$): δ 175.7, 157.5, 147.6, 131.5, 131.4, 130.5, 128.9, 128.1, 127.3, 122.1, 114.4, 79.7, 67.1, 66.8, 38.2, 37.8, 30.0, 15.0.

Example 22

2-Ethoxy-3-{3-[2-(4-methanesulfonyloxyphenyl) ethoxy]phenyl}propanoic Acid Ethyl Ester (a) 4-[2-(3-Formylphenoxy)ethyl]phenylmethanesulfonate 3-Hydroxybenzaldehyde was alkylated with 2-(4-methanesulfonyloxyphenyl)ethylmethanesulfonate (described in Example 1a) using the same method as in Example 1b to give 4-[2-(3-formylphenoxy)ethyl] phenylmethanesulfonate.

$^1$H-NMR (400 MHz; CDCl$_3$): δ 3.12 (t, 2H, J=6.7 Hz), 3.13 (s, 3H), 4.23 (t, 2H, J=6.7 Hz), 7.13–7.18 (m, 1H), 7.22–7.26 (m, 2H), 7.32–7.38 (m, 3H), 7.40–7.47 (m, 2H), 9.95 (s, 1H). $^{13}$C-NMR (100 MHz; CDCl$_3$): δ 34.9, 37.2, 68.3, 112.7, 121.7, 121.9, 123.5, 128.6, 130.4, 137.5, 147.8, 159.1, 191.9.

(b) 2-Ethoxy-3-{3-[2-(4-methanesulfonyloxyphenyl) ethoxy]phenyl}acrylic Acid Ethyl Ester 2-Ethoxy-3-{3-[2-(4-methanesulfonyloxyphenyl)ethoxy] phenyl}acrylic acid ethyl ester was synthesized from 4-[2-

(3-formylphenoxy)ethyl]phenylmethanesulfonate and (1,2-diethoxy-2-oxoethyl)(triphenyl)phosphonium chloride using the same method as in Example 1c.

$^1$H-NMR (400 MHz; CDCl$_3$): δ 1.34 (2x t, 6H, J=7 Hz), 3.04–3.09 (m, 5H), 3.99 (q, 2H, J=7 Hz), 4.15 (t, 2H, J=7 Hz), 4.27 (apparently q, 2H, J=7 Hz), 6.8–6.85 (m, 1H), 6.92 (s, 1H), 7.1–7.25 (m, 3H), 7.28–7.33 (m, 3H), 7.39–7.42 (m, 1H). $^{13}$C-NMR (100 MHz; CDCl$_3$): δ 14.0, 15.3, 34.7, 36.8, 60.8, 67.4, 67.9, 115.2, 121.7, 122.7, 123.2, 129.1, 130.2, 134.7, 137.6, 144.7, 147.7, 158.3, 164.1.

(c) 2-Ethoxy-3-{3-[2-(4-methanesulfonyloxyphenyl)ethoxy]phenyl}propanoic Acid Ethyl Ester 2-Ethoxy-3-{3-[2-(4-methanesulfonyloxyphenyl)ethoxy]phenyl}acrylic acid ethyl ester (3.69 g; 8.50 mmole) was hydrogenated for 3.5 hours at atmospheric pressure in ethyl acetate (70 ml) and acetic acid (0.5 ml) using Pd/C as catalyst and then filtered through hyflo. The solvent was evaporated in vacuo, dichloromethane and water were added and the phases were separated. The organic phase was dried (sodium sulfate), filtered and evaporated in vacuo to give 3.45 g (yield 93%) of 2-ethoxy-3-{3-[2-(4-methanesulfonyloxyphenyl)ethoxy]phenyl}propanoic acid ethyl ester.

$^1$H-NMR (500 MHz; CDCl$_3$): δ 1.16 (t, 3H, J=7 Hz), 1.22 (t, 3H, J=7.1 Hz), 2.95–2.99 (m, 2H), 3.09 (t, 2H, J=6.7 Hz), 3.13 (s, 3H), 3.31–3.39 (m, 1H), 3.56–3.64 (m, 1H), 3.98–4.02 (m, 1H), 4.13–4.20 (m, 4H), 6.73–6.85 (m, 3H,), 7.15–7.25 (m, 3H), 7.34 (dm, 2H, J=8.6 Hz, unresolved). $^{13}$C-NMR (100 MHz; CDCl$_3$): δ 14.2, 15.0, 35.1, 37.2, 39.3, 60.8, 68.0, 80.1, 112.7, 115.6, 121.9 (overlapping signals), 129.2, 130.5, 138.0, 138.8, 147.8, 158.5, 172.5.

Example 23

2-Ethoxy-3-{3-[2-(4-methanesulfonyloxyphenyl)ethoxy]phenyl}propanoic Acid

Lithium hydroxide hydrate (0.175 g; 4.18 mmole) in water (5 ml) was slowly added to a solution of 2-ethoxy-3-{3-[2-(4-methanesulfonyloxyphenyl)ethoxy]phenyl}propanoic acid ethyl ester (described in Example 22) (1.66 g; 3.80 mmole) in tetrahydrofuran (17 ml) at 0° C. After stirring at room temperature for 2 hours tetrahydrofuran was removed by evaporation in vacuo. The residue was extracted with diethyl ether. The water phase was acidified with hydrochloric acid, and extracted with ethyl acetate. The organic phase was washed with brine, dried (sodium sulfate), filtered and the solvent was evaporated in vacuo to give 1.5 g (96.5% yield) of 2-ethoxy-3-{3-[2-(4-methanesulfonyloxyphenyl)ethoxy]-phenyl}propanoic acid.

$^1$H-NMR (500 MHz; CDCl$_3$): δ 1.13 (t, 3H, J=7 Hz), 2.91–2.98 (m, 1H), 3.03–3.09 (m, 3H), 3.09 (s, 3H), 3.33–3.41 (m, 1H), 3.56–3.64 (m, 1H), 4.03–4.08 (m, 1H), 4.13 (t, 2H, J=6.9 Hz), 6.75 (dd, 1H, J=8.3, 2.07 Hz), 6.81 (s, 1H), 6.84 (d, 1H, J=7.5 Hz), 7.14–7.23 (m, 3H), 7.31 (dm, 2H, J=8.56 Hz, unresolved), 10.91 (bs, 1H, OH). $^{13}$C-NMR (125 MHz; CDCl$_3$): δ 14.8, 35.0, 37.0, 38.8, 66.4, 67.9, 76.5, 112.7, 115.6, 121.78, 121.81, 129.1, 130.4, 137.8, 138.5, 147.7, 158.4, 176.7.

Example 24

2-Ethoxy-3-{4-[3-(3-methanesulfonyloxyphenyl)propoxy]phenyl}propanoic Acid Ethyl Ester (a) 3-(3-Methanesulfonyloxyphenyl)propylmethanesulfonate Methanesulfonyl chloride (4.77 g; 41.8 mmole) in dichloromethane (20 ml) was slowly added to a solution of 3-(3-hydroxyphenyl)-1-propanol (3.03 g; 19.9 mmole) and triethylamine (6.04 g; 59.7 mmole) in dichloromethane at −20° C. The reaction mixture was allowed to reach room temperature and solid material was filtered off. The filtrate was washed with sodium bicarbonate solution (3 times) and brine, dried (magnesium sulfate) and the solvent was evaporated in vacuo. Purification by chromatography on silica gel using dichloromethane:methanol (gradient 0–8% methanol) gave 4.22 g (yield 69%) of 3-(3-methanesulfonyloxyphenyl)propylmethanesulfonate.

$^1$H-NMR (300 MHz; CDCl$_3$): δ 2.0 (m, 2H), 2.7 (t, 2H), 2.9 (s, 3H), 3.1 (s, 3H), 4.15 (t, 2H), 7.05–7.15 (m, 3H), 7.2–7.3 (m, 1H). $^{13}$C-NMR (75 MHz; CDCl$_3$): δ 30.3, 31.2, 37.3, 37.4, 68.9, 119.8, 122.1, 127.6, 130.1, 143.0, 149.4.

(b) 2-Ethoxy-3-{4-[3-(3-methanesulfonyloxyphenyl)propoxy]phenyl}propanoic Acid Ethyl Ester 2-Ethoxy-3-(4-hydroxyphenyl)propanoic acid ethyl ester (described in Example 20b) was alkylated with 3-(3-methanesulfonyloxyphenyl)propylmethanesulfonate using the same method as in example 1 (b) to give 2-ethoxy-3-{4-[3-(3-methanesulfonyloxyphenyl)propoxy]-phenyl}propanoic acid ethyl ester.

$^1$H-NMR (300 MHz; CDCl$_3$): δ 1.15 (t, 3H), 1.2 (t, 3H), 2.1 (qvint, 2H), 2.8 (t, 2H), 2.95 (d, 2H), 3.05 (s, 3H), 3.3–3.4 (m, 1H), 3.55–3.65 (m, 1H), 3.85–4.0 (m, 3H), 4.15 (q, 2H), 6.8 (d, 2H), 7.1–7.22 (m, 5H), 7.35 (t, 1H). $^{13}$C-NMR (75 MHz; CDCl$_3$): δ 14.2, 15.1, 30.6, 31.9, 37.2, 38.4, 60.8, 66.2, 66.5, 80.4, 114.2, 119.5, 122.0, 127.6, 129.3, 129.9, 130.4, 144.2, 149.4, 157.6, 172.5.

Example 25

2-Ethoxy-3-{4-[3-(3-methanesulfonyloxyphenyl)propoxy]phenyl}propanoic Acid

2-Ethoxy-3-{4-[3-(3-methanesulfonyloxyphenyl)propoxy]phenyl}propanoic acid ethyl ester (described in Example 24b) was hydrolyzed using the same method as in Example 2 to give 2-ethoxy-3-{4-[3-(3-methanesulfonyloxyphenyl)propoxy]phenyl}propanoic acid.

$^1$H-NMR (300 MHz; CDCl$_3$): δ 1.15 (t, 3H), 2.1 (qvint, 2H), 2.85 (t, 2H), 2.9–3.07 (m, 2H), 3.1 (s, 3H), 3.37–3.47 (m, 1H), 3.57–3.67 (m, 1H), 3.95 (t, 2H), 4.05 (m, 1H), 6.8 (d, 2H), 7.1–7.2 (m, 5H), 7.35 (t, 1H). $^{13}$C-NMR (75 MHz; CDCl$_3$): δ 15.0, 30.6, 31.9, 37.3, 37.9, 66.5, 66.7, 79.8, 114.3, 119.5, 122.0, 127.6, 128.8, 129.9, 130.5, 144.2, 149.4, 157.8, 176.4.

Example 26

2-Ethoxy-3-(4-{2-[4-(2-propanesulfonyloxy)phenyl]-ethoxy}phenyl)propanoic Acid Ethyl Ester (a) 3-{4-[2-(4-Benzyloxyphenyl)ethoxy]phenyl}-2-ethoxypropanoic Acid Ethyl Ester Azodicarbonyl dipiperidine (7.5 g; 30 mmole) was added to 2-ethoxy-3-(4-hydroxyphenyl)propanoic acid ethyl ester (described in Example 20b) (7 g; 30 mmole), 2-(4-benzyloxyphenyl)ethanol (6.8 g; 30 mmole) and triphenylphosphine (7.8 g; 30 mmole) dissolved i dichloromethane. After stirring at room temperature overnight the solvent was evaporated in vacuo and diethyl ether was added. The solid material was filtered off after 1 hour and the filtrate was evaporated in vacuo. Purification by chromatography on silica gel using ethyl acetate:dichloromethane as eluant gave 10 g (yield 75%) of 3-{4-[2-(4-benzyloxyphenyl)ethoxy]phenyl}-2-ethoxypropanoic acid ethyl ester.

¹H-NMR (300 MHz; CDCl₃): δ 1.15–1.30 (m, 6H), 2.95 (d, 2H), 3.05 (t, 2H), 3.3–3.42 (m, 1H), 3.58–3.7 (m, 1H), 4.0 (m, 1H), 4.05–4.25 (m, 4H), 5.05 (s, 2H), 6.85 (d, 2H), 6.95 (d, 2H), 7.1–7.25 (m, 4H), 7.3–7.5 (m, 5H). ¹³C-NMR (75 MHz; CDCl₃): δ 14.3, 15.1, 35.0, 38.5, 60.8, 66.2, 68.9, 70.0, 80.5, 114.4, 114.9, 127.5, 128.0, 128.6, 129.3, 130.0, 130.4, 130.6, 137.1, 157.5, 157.6, 172.6.

b) 2-Ethoxy-3-{4-[2-(4-hydroxyphenyl)ethoxy]phenyl}propanoic Acid Ethyl Ester.

3-{4-[2-(4-Benzyloxyphenyl)ethoxy]phenyl}-2-ethoxypropanoic acid ethyl ester (16 g; 35.6 mmole) was hydrogenated at atmospheric pressure in ethyl acetate (300 ml) using Pd/C (dry, 10%) as catalyst. The mixture was filtered through celite and the solvent was evaporated in vacuo to give 11.2 g (yield 88%) of 2-ethoxy-3-{4-[2-(4-hydroxyphenyl)ethoxy]phenyl}propanoic acid ethyl ester.

¹H-NMR (300 MHz; CDCl₃): δ 1.1–1.30 (m, 6H), 2.9–3.05 (m, 4H), 3.3–3.45 (m, 1H), 3.55–3.70 (m, 1H), 4.0 (m, 1H), 4.1 (t, 2H), 4.02 (q, 2H), 6.5 (s br, 1 OH), 6.75–6.85 (m, 4H), 7.05–7.2 (m, 4H). ¹³C-NMR (75 MHz; CDCl₃): δ 14.2, 15.0, 34.9, 38.4, 61.1, 66.3, 69.0, 80.4, 114.4, 115.5, 129.1, 129.8, 130.0, 130.4, 154.7, 157.6, 173.0.

(c) 2-Ethoxy-3-(4-{2-[4-(2-propanesulfonyloxy)phenyl]ethoxy}phenyl)propanoic Acid Ethyl Ester Triethylamine (0.64 g; 6.28 mmole) was slowly added to a solution of 2-ethoxy-3-{4-[2-(4-hydroxyphenyl)ethoxy]phenyl}propanoic acid ethyl ester (1.5 g; 4.18 mmole) in dry dichloromethane (20 ml). After cooling to 0° C. isopropylsulfonyl chloride (0.9 g; 6.28 mmole) was added slowly. The reaction mixture was stirred over night at room temperature, water was added and the mixture was extracted with dichloromethane. The organic phase was washed with hydrochloric acid (1M) and sodium bicarbonate solution, dried (magnesium sulfate) and evaporated in vacuo to give 1.75 g (yield 90%) of 2-ethoxy-3-(4-{2-[4-(2-propanesulfonyloxy)phenyl]ethoxy}phenyl)propanoic acid ethyl ester.

¹H-NMR (500 MHz; CDCl₃): δ 1.16 (t, 3H, J=7 Hz), 1.22 (t, 3H, J=7 Hz), 1.55 (d, 6H, J=6.7 Hz), 2.92–2.96 (m, 2H), 3.08 (t, 2H, J=7 Hz), 3.31–3.38 (m, 1H), 3.41–3.50 (m, 1H), 3.55–3.64 (m, 1H), 3.94–3.98 (m, 1H), 4.114–19 (m, 4H), 6.80 (dm, 2H, J=8.6 Hz, unresolved), 7.14 (dm, 2H, J=8.6 Hz, unresolved), 7.21 (dm, 2H, J=8.6 Hz, unresolved), 7.31 (dm, 2H, J=8.6 Hz, unresolved).

Example 27

2-Ethoxy-3-(4-{2-[4-(2-propanesulfonyloxy)phenyl]ethoxy}phenyl)propanoic Acid

2-Ethoxy-3-(4-{2-[4-(2-propanesulfonyloxy)phenyl]ethoxy}phenyl)propanoic acid ethyl ester (described in Example 26) was hydrolyzed using the same method as in Example 2 to give 2-ethoxy-3-(4-{2-[4-(2-propanesulfonyloxy)phenyl]ethoxy}phenyl)propanoic acid.

¹H-NMR (500 MHz; CDCl₃): δ 1.17 (t, 3H, J=7.2 Hz), 1.54 (d, 6H, J=6.8 Hz), 2.91–2.98 (m, 1H), 3.03–3.1 (m, 3H), 3.38–3.52 (m, 2H), 3.55–3.65 (m, 1H), 4.01–4.06 (m, 1H), 4.14 (t, 2H, J=6.9 Hz), 6.81 (dm, 2H, J=8.6 Hz, unresolved), 7.15 (dm, 2H, J=8.6 Hz, unresolved), 7.21 (dm, 2H, J=8.6 Hz, unresolved), 7.31 (dm, 2H, J=8.6 Hz, unresolved), 7.96 (bs, 1H). ¹³C-NMR (125 MHz; CDCl₃): 3 15.0, 16.7, 35.1, 37.8, 52.3, 66.8, 68.2, 79.7, 114.4, 121.9, 128.8, 130.4, 130.5, 137.4, 147.6, 157.5, 175.7.

Example 28

2-Ethoxy-3-(4-{2-[4-(4-nitrobenzenesulfonyloxy)phenyl]ethoxy}phenyl)propanoic Acid Ethyl Ester 2-Ethoxy-3-{4-[2-(4-hydroxyphenyl)ethoxy]phenyl}propanoic acid ethyl ester (described in Example 26b) was esterified with 4-nitrobenzenesulfonyl chloride using the same method as in Example 26 (c) to give 2-ethoxy-3-(4-{2-[4-(4-nitrobenzenesulfonyloxy)phenyl]ethoxy}phenyl)propanoic acid ethyl ester.

¹H-NMR (400 MHz; CDCl₃): δ 1.16 (t, 3H, J=7 Hz), 1.23 (t, 3H, J=7 Hz), 2.92–2.97 (m, 2H), 3.05 (t, 3H, J=6.5 Hz), 3.30–3.39 (m, 1H), 3.54–3.65 (m, 1H), 3.93–3.99 (m, 1H), 4.12 (t, 2H, J=6.8 Hz), 4.16 (q, 2H, J=7 Hz), 6.77 (dm, 2H, J=8.8 Hz, unresolved), 6.93 (dm, 2H, J=8.8 Hz, unresolved), 7.14 (dm, 2H, J=8.8 Hz, unresolved), 7.23 (dm, 2H, J=8.8 Hz, unresolved), 8.03 (dm, 2H, J=8.8 Hz, unresolved), 8.36 (dm, 2H, J=8.8 Hz, unresolved).

Example 29

2-Ethoxy-3-(4-{2-[4-(4-nitrobenzenesulfonyloxy)phenyl]ethoxy}phenyl)propanoic Acid 2-Ethoxy-3-(4-{2-[4-(4-nitrobenzenesulfonyloxy)phenyl]ethoxy}phenyl)propanoic acid ethyl ester (described in Example 28) was hydrolyzed by the same method as in Example 2 to give 2-ethoxy-3-(4-{2-[4-(4-nitrobenzenesulfonyloxy)phenyl]ethoxy}phenyl)propanoic acid ¹H-NMR (500 MHz; CDCl₃): δ 1.16 (t, 3H, J=7 Hz), 2.91–3.01 (m, 1H), 3.01–3.08 (m, 2H), 3.37–3.45 (m, 1H), 3,58–3.66 (m, 1H), 4.0–4.06 (m, 1H) 4.084.14 (m, 2H), 6.78 (dm, 2H, J=8.6 Hz, unresolved), 6.92 (dm, 2H, J=8.6 Hz, unresolved), 7.15 (dm, 2H, J=8.6 Hz, unresolved), 7.23 (dm, 2H, J=8.6 Hz, unresolved), 8.02 (dm, 2H, J=9.1 Hz, unresolved), 8.34 (dm, 2H, J=9.1 Hz, unresolved), 9.56 (bs, 1H). ¹³C-NMR (125 MHz; CDCl₃): δ 14.9, 35.0, 37.8, 66.6, 67.9, 79.6, 114.2, 115.3, 121.9, 124.2, 129.0, 129.8, 130.4, 138.3, 140.9, 147.7, 150.8, 157.4, 176.3.

Example 30

2-Ethoxy-3-{4-[2-(4-phenylmethanesulfonyloxyphenyl)ethoxy]phenyl}propanoic Acid Ethyl Ester 2-Ethoxy-3-{4-[2-(4-hydroxyphenyl)ethoxy]phenyl}propanoic acid ethyl ester (described in Example 26b) (0.54 g; 1.5 mmole) was dissolved in dichloromethane (15 ml), triethylamine (0.23 g; 0.31 ml; 2.25 mmole) was added. The solution was cooled to 0° C. and benzylsulfonyl chloride (0.43 g; 2.25 mmole) dissolved in dichloromethane (5 ml) was added. The resulting mixture was allowed to reach room temperature and was stirred over night. Water was added, the organic layer separated and the water phase extracted with dichloromethane. The organic phase was washed with hydrochloric acid (1 M), sodium hydrogen carbonate and brine. After drying with sodium sulfate and evaporation a light yellow oil was obtained. The crude product was purified with flash chromatography on silica. The compound was eluated with heptane:ethyl acetate (9:1 followed by 1:1). Pure fractions were pooled and evaporated yielding 0.55 g (71%) of 2-ethoxy-3-{4-[2-(4-phenylmethanesulfonyloxyphenyl)ethoxy]phenyl}propanoic acid ethyl ester.

¹H-NMR (300 MHz, CDCl₃): δ 1.18 (t, 3H); 1.25 (t, 3H); 2.97 (d, 2H); 3.09 (t, 2H); 3.30–3.45 (m, 1H); 3.55–3.70 (m, 1H); 3.98 (t, 1H); 4.14 (t, 2H); 4.19 (q, 2H); 4.52 (s, 2H); 6.82 (d, 2H); 7.08 (d, 2H); 7.17 (d, 2H); 7.29 (d, 2H); 7.40–7.53 (m, 5H) ¹³C-NMR (75 MHz, CDCl₃): δ 14.6, 15.4, 35.5, 38.8, 57.0, 61.9, 66.5, 68.5, 80.6, 114.5, 122.2, 127.5, 129.2, 129.5, 129.7, 130.1, 130.6, 131.1, 137.9, 148.0, 157.6, 172.7.

Example 31

2-Ethoxy-3-{4-[2-(4-phenylmethanesulfonyloxyphenyl)ethoxyphenyl}propanoic Acid 2-Ethoxy-3-{4-[2-(4-phenylmethanesulfonyloxyphenyl)ethoxy]phenyl}propanoic acid ethyl ester (described in Example 30) (0.21 g; 0.41 mmol) was dissolved in tetrahydrofuran (4 ml) and lithium hydroxide (0.021 g; 0.48 mmol) dissolved in water (1 ml) was added dropwise. The resulting solution was stirred at room temperature over night and then acidified with hydrochloric acid (2M). Extraction with ethyl acetate, drying with magnesium sulfate and evaporation gave 0.184 g (92%) of 2-ethoxy-3-{4-[2-(4-phenylmethanesulfonyloxy-phenyl)ethoxy]phenyl}propanoic acid as an oil.

$^1$H-NMR (500 MHz, CDCl$_3$): δ 1.20 (t, 3H); 2.94–3.01 (dd, 1H); 3.06–3.13 (m, 3H); 3.41–3.52 (m, 1H); 3.58–3.69 (m, 1H); 4.06 (dd, 1H); 4.15 (t, 2H); 4.53 (s, 2H); 6.84 (d, 2H); 7.09 (d, 2H); 7.18 (d, 2H); 7.31 (d, 2H); 7.44–7.48 (m, 5H) $^{13}$C-NMR (125 MHz, CDCl$_3$): δ 15.3, 35.4, 38.1, 57.0, 67.1, 68.5, 80.0, 114.7, 122.2, 127.5, 129.1, 129.2, 129.5, 130.7, 130.8, 131.1, 137.9, 148.1, 157.8, 175.6.

Example 32

2-Ethoxy-3-{4-[2-(4-methanesulfonyloxyphenyl)ethoxy]phenyl}butanoic Acid Ethyl Ester (a) 3-(4-Benzyloxyphenyl)-2-ethoxy-3-methylacrylic Acid Ethyl Ester LHMDS (11 ml, 11 mmole, 1 M in tetrahydrofuran) was added to a solution of triethyl 2-ethoxyphosphonoacetate (2.95 g; 11 mmole) in dry tetrahydrofuran (30 ml) at −50° C. under nitrogen atmosphere, the mixture was stirred for 1.5 hours and then the temperature was allowed to rise to 2° C. 1-(3-benzyloxyphenyl)ethanone (2.3 g; 10 mmole) dissolved in tetrahydrofuran was slowly added and the resulting mixture was stirred overnight at room temperature. Saturated ammonium chloride solution (40 ml) was added and after 1 hour the phases were separated. The water phase was extracted twice with ethyl acetate, the organic phases were combined and the solvent evaporated in vacuo. Purification twice by chromatography using ethyl acetate:heptane as eluant gave 0.6 g (yield 18%) of 3-(4-benzyloxyphenyl)-2-ethoxy-3-methylacrylic acid ethyl ester as a mixture of Z and E isomers, which was used in the next step without further purification.

Major isomer $^1$H-NMR (500 MHz; CDCl$_3$): δ 0.99 (t, 3H, J=7 Hz), 1.37 (t, 3H, J=7 Hz), 2.13 (s, 3H), 3.88 (q, 2H, J=7 Hz), 4.0 (q, 2H, J=7 Hz), 5.11 (s, 2H), 6.94 (dm, 2H, J=9 Hz, unresolved), 7.11 (dm, 2H, J=9 Hz, unresolved), 7.33–7.50 (m, 5H).

(b) 3-(4-Hydroxyphenyl)-2-ethoxybutanoic Acid Ethyl Ester 3-(4-Benzyloxyphenyl)-2-ethoxy-3-methylacrylic acid ethyl ester (1.58 g; 4.64 mmole) was hydrogenated at atmospheric pressure in ethyl acetate (20 ml) using Pd/C (wet) as catalyst. After filtration through celite, the solvent was evaporated in vacuo to give (1.1 g; yield 94%) of 3-(4-hydroxyphenyl)-2-ethoxybutanoic acid ethyl ester as a diastereomeric mixture.

Major isomer $^1$H-NMR (500 MHz; CDCl$_3$): δ 1.17 (t, 3H, J=7 Hz), 1.25 (t, 3H, J=7 Hz), 1.32 (d, 3H, J=7 Hz), 3.17 (qvint, 1H, J=7 Hz), 3.29–3.38 (m, 1H), 3.60–3.68 (m, 1H), 3.88–3.92 (m, 2H), 4.18 (q, 2H, J=7 Hz), 5.2 (bs, 1OH), 6.71–6.77 (m, 2H), 7.11–7.16 (m, 2H).

(c) 2-Ethoxy-3-{4-[2-(4-methanesulfonytoxyphenyl)ethoxy]phenyl}butanoic Acid Ethyl Ester 3-(4-Hydroxyphenyl)-2-ethoxybutanoic acid ethyl ester was alkylated with 2-(4-methanesulfonyloxyphenyl)ethylmethanesulfonate (described in Example 1a) using the same method as in Example 1(b) to give 2-ethoxy-3-{4-[2-(4-methanesulfonyloxyphenyl)ethoxy]-phenyl}butanoic acid ethyl ester as a diastereomeric mixture.

Major isomer $^1$H-NMR (500 MHz; CDCl$_3$): δ 1.15 (t, 3H, J=7 Hz), 1.24 (t, 3H, J=7 Hz), 1.31 (d, 3H, J=7 Hz), 2.99–3.20 (m, 6H), 3.28–3.35 (m, 1H), 3.58–3.65 (m, 1H), 3.88 (d, 1H, J=6.5 Hz), 4.14–4.20 (m, 4H), 6.83 (dm, 2H, J=8.5 Hz, unresolved), 7.18 (dm, 2H, J=8.5 Hz, unresolved), 7.25 (dm, 2H, J=8.5 Hz, unresolved), 7.36 (dm, 2H, J=8.5 Hz, unresolved).

Example 33

2-Ethoxy-3-{4-[2-(4-methanesulfonyloxyphenyl)ethoxy]phenyl}butanoic Acid

2-Ethoxy-3-{4-[2-(4-methanesulfonyloxyphenyl)ethoxy]phenyl}butanoic acid ethyl ester (described in Example 32) was hydrolyzed using the same method as in Example 2 to give 2-ethoxy-3-{4-[2-(4-methanesulfonyloxyphenyl)ethoxy]phenyl}butanoic acid as a diasteromeric mixture.

Major isomer $^1$H-NMR (400 MHz; CDCl$_3$): δ 1.20 (t, 3H, J=8 Hz), 1.37 (d, 3H, J=7.2 Hz), 3.06–3.15 (m, 5H), 3.15–3.25 (m, 1H), 3.40–3.50 (m, 1H), 3.62–3.72 (m, 1H), 3.93 (d, 1H, J=5.6 Hz), 4.15 (t, 2H, J=6.8 Hz), 6.81 (dm, 2H, J=8,8 Hz, unresolved), 7.17 (dm, 2H, J=8,8 Hz, unresolved), 7.23 (dm, 2H, J=8,8 Hz, unresolved), 7.33 (dm, 2H, J=8,8 Hz, unresolved). $^{13}$C-NMR (100 MHz; CDCl$_3$): δ 15.0, 17.9, 35.1, 37.2, 41.7, 67.6, 68.1, 83.5, 114.2, 121.9, 129.2, 130.5, 133.5, 138.0, 147.8, 157.5, 175.4.

Example 34

2-Ethoxy-3-[4-(4-{2-methanesulfonyloxyphenyl}butoxy)phenyl]propanoic Acid (a) 4-(2-Benzyloxyphenyl)-3-buten-1-ol 2-Benzyloxybenzaldehyde (8 g; 37 mmole), (3-hydroxypropyl)triphenylphosponium bromide (19.5 g; 47 mmole) and potassium carbonate (6.6 g; 48 mmole) were mixed in isopropanol. The reaction mixture was refluxed over night then filtered and the filtrate was evaporated. Chromatography using ethyl acetate:dichloromethane (up to 5%) as eluant gave 8.4 g (87.6%) of 4-(2-benzyloxyphenyl)-3-buten-1-ol. Both cis and trans 4-(2-benzyloxyphenyl)-3-buten-1-ol were formed according to NMR.

$^1$H-NMR (300 MHz; CDCl$_3$) of the major isomer: δ 1.9–2.05 (b, 1H, OH), 2.43–2.6 (m, 2H), 3.7–3.8 (m, 2H), 5.2 (s, 2H), 6.2–6.3 (m, 1H), 6.85–7.5 (m, 10H, unresolved) $^1$H-NMR (300 MHz; CDCl$_3$) of the minor isomer: d 1.9–2.05 (b, 1H, OH), 2.43–2.6 (m, 2H), 3.7–3.8 (m, 2H), 5.2 (s, 2H), 5.7–5.8 (m, 1H), 6.8 (d, 1H), 6.85–7.5 (m, 9H, unresolved).

(b) 4-(2-Hydroxyphenyl)butanol 4-(2-Benzyloxyphenyl)-3-buten-1-ol was hydrogenated in ethanol using the same method as in Example 20b.

$^1$H-NMR (300 MHz; CDCl$_3$): δ 1.5–1.73 (m, 4H), 2.65 (t, 2H), 3.65 (t, 2H), 6.75–6.9 (m, 2H), 7.02–7.15 (m, 2H), 7.4 (bs, 1H). $^{13}$C-NMR (75.5 MHz; CDCl$_3$): δ 26.4, 29.6, 31.5, 62.8, 115.6, 120.5, 127.1, 128.8, 130.3, 154.0.

(c) 4-(2-Methanesulfonyloxyphenyl)butylmethanesulfonate.

4-(2-Methanesulfonyloxyphenyl)butylmethanesulfonate was synthesized using the same method as in Example 18a from 4-(2-hydroxyphenyl)butanol.

$^1$H-NMR (300 MHz; CDCl$_3$): δ 1.7–1.83 (m, 4H), 2.7–2.88 (m, 2H), 2.95 (s, 3H), 3.17 (s, 3H), 4.25 (t, 2H), 7.2–7.3 (m, 4H). $^{13}$C-NMR (75.5 MHz; CDCl$_3$): δ 25.8, 28.6, 29.3, 37.2, 38.3, 69.8, 122.0, 127.4, 127.6, 130.8, 134.7, 147.5.

(d) 2-Ethoxy-3-{4-(4-(2-methanesulfonyloxyphenyl)butoxy]phenyl}propanoic Acid Ethyl Ester 2-Ethoxy-3-{4-(4-(2-methanesulfonyloxyphenyl)butoxy]phenyl}propanoic acid ethyl ester was synthesized using the same method as in Example 1b from 2-ethoxy-3-(4-hydroxyphenyl)propanoic acid ethyl ester (described in Example 20b) and 4-(2-methanesulfonyloxyphenyl)butylmethanesulfonate.

(e) 2-Ethoxy-3-[4-(4-{2-methanesulfonyloxyphenyl}butoxy)phenyl]propanoic Acid

2-Ethoxy-3-{4-(4-(2-methanesulfonyloxyphenyl)butoxy]phenyl}propanoic acid ethyl ester (2.7 g; 5.8 mmole) was dissolved in tetrahydrofuran: water (1:3, 100 ml). Lithium hydroxide (0.36 g; 8.7 mmole) dissolved in a small amount of water was added. The reaction mixture was stirred over night at room temperature and then evaporated. The residue was redissolved in ethyl acetate and hydrochloric acid (2M) and extracted. After separation the organic phase was extracted with sodium hydroxide (1M, 30 ml). The water phase was cooled, acidified with hydrochloric acid (conc) and extracted with ethyl acetate. The organic phase was dried with magnesium sulfate and evaporation gave 2 g (79% yield) of 2-ethoxy-3-[4-(4-{2-methanesulfonyloxyphenyl}butoxy)phenyl]propanoic acid.

$^1$H-NMR (500 MHz, CDCl$_3$): δ 1.2 (t, 3H), 1.86 (m, 4H), 2.81 (t, 2H), 2.94–3.0 (m, 1H), 3.06–3.11 (m, 1H), 3.2 (s, 3H), 3.43–3.48 (m, 1H), 3.6–3.65 (m, 1H), 4.0 (t, 3H), 4.95–4.08 (m, 1H), 6.84 (d, 2H), 7.17 (d, 2H), 7.25–7.28 (m, 2H), 7.32–7.35 (m, 2H). $^{13}$C-NMR (100 MHz, CDCl$_3$): δ 15.2, 26.7, 29.2, 30.0, 38.0, 38.4, 67.0, 67.7, 80.0, 114.6, 122.2, 127.5, 127.7, 128.8, 130.7, 131.0, 135.3, 147.7, 158.1, 175.8.

Example 35

2-Ethoxy-3-[4-(2-{4-methylsulfonyloxyphenyl}ethoxy)-2-nitrophenyl]propanoic Acid Methyl Ester (a) 3-(4-Benzyloxy-2-nitrophenyl)-2-oxopropanoic Acid Potassium ethoxide (505 g; 6 mole) was added to a solution of ethanol (710 ml) and diethyl ether (4.8 l) and the mixture was cooled to 0° C. 4-(Benzyloxy)-1-methyl-2-nitrobenzene (639.8 g; 3 mole) dissolved in diethyl oxalate (900 g; 6.16 mole) and toluene (1500 ml) was added slowly during 30 minutes. The reaction mixture was stirred for 3 hours at 0° C. and then allowed to stand cold over night. After 5 days at room temperature the reaction mixture was filtered and the filter cake was washed with diethyl ether (2 l). The cake was then treated with water (10 l), sodium hydroxide (5 M, 0.8 l) and extracted three times with diethyl ether (3×3 l). The water phase was cooled and acidified in two steps while stirring with hydrochloric acid:water (1:1, 0.9 l). First to pH 5 and the reaction mixture was then stirred for 1 hour before the acidification continued to pH 2. The reaction mixture was cooled in an ice:sodium chloride bath. Filtration after 1 hour gave 849.5 g (89.8%) of 3-(4-benzyloxy-2-nitrophenyl)-2-oxopropanoic acid.

$^1$H-NMR (500 MHz, DMSO-d$_6$): δ 4.33 (s, 2H), 5.21 (s, 2H), 7.32–7.36 (m, 2H), 7.39–7.50 (m, 5H), 7.65 (d, J=2.6 Hz, 1H).

(b) 3-(4-Benzyloxy-2-nitrophenyl)-2-oxopropanoic Acid Methyl Ester 3-(4-Benzyloxy-2-nitrophenyl)-2-oxopropanoic acid (40 g; 0.127 mole) was dissolved in methanol (300 ml). Hydrochloric acid (conc, 10 ml) was added under stirring. The reaction mixture was heated to reflux for 3.5 hours and then evaporated to dryness. Dichloromethane and water were added to the residue and the phases were separated. The organic phase was washed with diluted sodium hydrogencarbonate solution and water, and dried with magnesium sulfate. Filtration through a short silica gel column and evaporation gave 29.6 g (71% yield) of 3-(4benzyloxy-2-nitrophenyl)-2-oxopropanoic acid methyl ester as a yellow solid.

$^1$H-NMR (300 MHz, CDCl$_3$): δ 3.93 (s, 3H), 4.46 (s, 2H), 5.14 (s, 2H), 7.22 (br, 2H), 7.36–7.45 (m, 5H) 7.79 (s, 1H).

(c) 3-(4-Benzyloxy-2-nitrophenyl)-2-hydroxypropanoic Acid Methyl Ester 3-(4-Benzyloxy-2-nitrophenyl)-2-oxopropanoic acid methyl ester (4.1 g; 12.4 mmole) was dissolved in methanol (60 ml). Sodium borohydride (0.5 g; 13.12 mmole) was added in portions under stirring. TLC (silica gel, ethyl acetate:heptane, 1:1) after one hour showed remaining starting material and the formation of a by product. The reaction mixture was then cooled in an ice-bath and more sodium borohydride (0.2 g; 5.26 mmole) was added. After addition, the mixture was stirred at 0° C. until the starting material was consumed. The reaction mixture was evaporated to dryness. Ethyl acetate and water were added to the residue and the phases were separated. The organic phase was washed with brine and dried with magnesium sulfate and evaporated. Chromatography of the crude product on silica gel using a gradient of ethyl acetate in heptane as eluant gave 2.5 g (61% yield) of 3-(4-benzyloxy-2-nitrophenyl)-2-hydroxypropanoic acid methyl ester as an oil product.

$^1$H-NMR (300 MHz, CDCl$_3$): δ 2.86 (d, J=6 Hz, 1H, OH), 3.12 (dd, J=14, 8 Hz, 1H), 3.47 (dd, J=14, 4 Hz, 1H), 3.79 (s, 3H), 4.45–4.51 (m, 1H), 5.10 (s, 2H), 7.15 (dd, J=8.8, 2.7 Hz, 1H), 7.33 (d, J=8.8 Hz, 1H), 7.35–7.43 (m, 5H) and 7.54 (d, J=2.7 Hz, 1H).

(d) 2-Ethoxy-3-(4-benzyloxy-2-nitrophenyl)propanoic Acid Methyl Ester 3-(4-Benzyloxy-2-nitrophenyl)-2-hydroxypropanoic acid methyl ester (1.86 g; 5.6 mmole) was dissolved in dichloromethane (20 ml). Molecular sieves (4 Å, 1.9 g) were added. Silver (I) oxide (1.96 g; 8.4 mmole) was then added while stirring, followed by addition of iodoethane (1.63 ml; 20.4 mmole). After 6 days stirring at room temperature the reaction was not completed according to TLC so more silver (I) oxide and iodoethane were added. The reaction mixture was stirred for 3 more days, then filtered through celite and the filtrate was evaporated to dryness. Chromatography of the crude product on silica gel using a gradient of ethyl acetate in heptane as eluant gave 1.6 g oil (80% yield) of 2-ethoxy-3-(4-benzyloxy-2-nitrophenyl)propanoic acid methyl ester.

$^1$H-NMR (400 MHz, CDCl$_3$): δ 1.13 (t, J=7 Hz, 3H); 3.23 (dd, J=14, 8 Hz, 1H), 3.29–3.37 (m, 2H), 3.58–3.66 (m, 1H), 3.72 (s, 3H), 4.15 (dd, J=8, 4.5 Hz, 1H), 5.12 (s, 2H), 7.15 (dd, J=8.5, 2.5 Hz, 1H), 7.31 (d, J=8.5 Hz, 1H), 7.36–7.45 (m, 5H), 7.55 (d, J=2.5 Hz, 1H).

(e) 2-Ethoxy-3-(4-hydroxy-2-nitrophenyl)propanoic Acid Methyl Ester

2-Ethoxy-3-(4-benzyloxy-2-nitrophenyl)propanoic acid methyl ester (1.5 g; 4.06 mmole) was dissolved in dichloromethane (8 ml) and dimethylsulfide (8 ml) was added. Boron trifluoride diethyl etherate (5.0 ml; 40.6 mmole) was added under stirring. The reaction mixture was stirred at room temperature for 4 hours and then poured into water and more dichloromethane was added. The phases were separated and the organic phase was washed with water and brine and dried with magnesium sulfate. Evaporation to remove the solvent gave 1.04 g (95% yield) of 2-ethoxy-3-(4-hydroxy-2-nitrophenyl)propanoic acid methyl ester.

$^1$H-NMR (400 MHz, CDCl$_3$): δ 1.15 (t, J=7 Hz, 3H); 3.26 (dd, J=14, 7.5 Hz, 1H), 3.34–3.42 (m, 2H), 3.58–3.66 (m, 1H), 3.77 (s, 3H), 4.19 (dd, J=7.5, 5.5 Hz, 1H), 6.38 (s, 1H), 6.96 (dd, J=8.5, 2.5 Hz, 1H), 7.22 (d, J=8.5 Hz, 1H), 7.37 (d, J=2.5 Hz, 1H).

(f) 2-Ethoxy-3-[4-(2-{4-methylsulfonyloxyphenyl}ethoxy)-2-nitrophenyl]propanoic Acid Methyl Ester 2-(4-Methanesulfonyloxyphenyl)ethylmethanesulfonate (1.14 g; 3.87 mmole), 2-ethoxy-3-(4-hydroxy-2-nitrophenyl)propanoic acid methyl ester (1.04 g; 3.86 mmole) and potassium carbonate (1.07 g; 7.75 mmole) were mixed in acetonitrile (approx. 100 ml). The reaction mixture was heated to reflux for 6 hours and according to TLC the reaction was not complete. Another portion of 2-(4-methanesulfonyloxyphenyl)ethylmethanesulfonate (0.2 g; 0.68 mmole) was added. The reaction mixture was heated to reflux over night, and then evaporated to dryness. Ethyl acetate and water were added into the residue. The phases were separated and the organic phase was washed with brine, dried with magnesium sulfate and evaporated. Chromatography of the crude product on silica gel with a gradient of ethyl acetate/heptane as eluant gave 1.47 g (81% yield) of 2-ethoxy-3-[4-(2-{4-methylsulfonyloxyphenyl}ethoxy)-2-nitrophenyl]propanoic acid methyl ester.

$^1$H-NMR (400 MHz, CDCl$_3$): δ 1.12 (t, J=7 Hz, 3H), 3.14 (t, J=7 Hz, 2H), 3.16 (s, 3H), 3.21 (dd, J=14, 8 Hz, 1H), 3.30–3.67 (m, 2H), 3.57–3.65 (m, 1H); 3.73 (s, 3H), 4.13 (dd, J=8, 5 Hz, 1H), 4.22 (t, J=7 Hz, 2H), 7.06 (dd, J=8.5, 2.5 Hz, 1H); 7.26 (d, J=8.5 Hz, 2H), 7.29 (d, J=8.5 Hz, 1H), 7.35 (d, J=8.5 Hz, 2H), 7.44 (d, J=2.5 Hz, 1H).

Example 36

2-Ethoxy-3-[4-(2-{4-methylsulfonyloxyphenyl}ethoxy)-2-nitrophenyl] propanoic Acid 2-Ethoxy-3-[4-(2-{4-methylsulfonyloxyphenyl}ethoxy)-2-nitrophenyl]propanoic acid methyl ester (described in Example 35) (0.8 g; 1.71 mmole) was dissolved in tetrahydrofuran (8 ml). A solution of lithium hydroxide monohydrate (0.086 g; 2.05 mmole) in water (8 ml) was added under stirring. The reaction mixture was stirred at room temperature for 5 hours and then evaporated to remove tetrahydrofuran. The residue was extracted with diethyl ether, acidified to pH~3 with hydrochloric acid (10%) and extracted with ethyl acetate. The organic phase was washed with water and brine, dried with magnesium sulfate. The solvent was removed and 0.72 g (93% yield) of 2-ethoxy-3-[4-(2-{4-methylsulfonyloxyphenyl}ethoxy)-2-nitropheny]propanoic acid was obtained.

$^1$H-NMR (400 MHz, CDCl$_3$): δ 1.13 (t, J=7 Hz, 3H), 3.13 (t, J=6.5 Hz, 2H), 3.15 (s, 3H), 3.23 (dd, J=14, 8 Hz, 1H), 3.36–3.43 (m, 1H), 3.48 (dd, J=14, 5 Hz, 1H), 3.59–3.66 (m, 1H), 4.15 (dd, J=8, 5 Hz, 1H), 4.22 (t, J=6.5 Hz, 2H), 7.06 (dd, J=8.5 2.5 Hz, 1H), 7.25 (d, J=8.5 Hz, 2H), 7.30 (d, J=8.5 Hz, 1H), 7.35 (d, J=8.5 Hz, 2H) and 7.43 (d, J=2.5 Hz, 1H). $^{13}$C-NMR (100 MHz, CDCl$_3$): δ 14.89, 34.88, 34.91, 37.33, 67.10, 68.79, 78.31, 110.13, 119.64, 122.09(2C), 123.30, 130.52(2C), 134.33, 137.29, 147.94, 150.22, 157.93 and 175.41.

Example 37

2-Ethoxy-3-[4-(2-{3-methoxy-4-methanesulfonyloxyphenyl}ethoxy)phenyl] propanoic Acid (a) 2-Ethoxy-3-[4-(2-{3-methoxy-4-methanesulfonyloxyphenyl}ethoxy)phenyl]propanoic Acid Ethyl Ester 2-[3-Methoxy-4-{methylsulfonyloxy}phenyl] ethylmethanesulfonate (described in WO 98/57941) (1.6 g; 4.9 mmole) was dissolved in acetonitrile. Potassium carbonate (1 g; 7.2 mmole) was added followed by addition of 2-ethoxy-3-(4-hydroxyphenyl)propanoic acid ethyl ester (described in Example 20b) (1 g; 4.2 mmole). The reaction mixture was refluxed for 2 hours and then stirred at room temperature for 16 hours. Acetonitrile was evaporated and the residue redissolved in diethyl ether and washed with water. The organic phase was dried with sodium sulfate and evaporated. NMR showed formation of the corresponding styren product and that the reaction was not completed so the crude product was redissolved in acetonitrile and more 2-[3-methoxy-4-{methylsulfonyloxy}phenyl] ethylmethanesulfonate (0.5 g; 1.5 mmole) was added. The mixture was refluxed for 2 more hours and then evaporated. The residue was redissolved in diethyl ether and washed with water. The organic phase was dried with magnesium sulfate and evaporated. Chromatography of the crude product gave 1 g of a mixture which according to NMR contained 60% (0.68 g, 34.7% yield) of 2-ethoxy-3-[4-(2-{3-methoxy-4-methanesulfonyloxyphenyl}ethoxy)-phenyl] propanoic acid ethyl ester and 40% (0.32 g) of 2-[3-methoxy-4-{methylsulfonyloxy}phenyl] ethylmethanesulfonate. This mixture was used without further purification in the next step.

$^1$H-NMR (300 MHz; CDCl$_3$): δ 1.13 (t, 3H), 1.2 (t, 3H), 2.92 (d, 2H), 2.96–3.1 (m, 2H), 3.13 (s, 3H), 3.27 (m, 1H), 3.52–3.67 (m, 1H), 3.87 (s, 3H), 3.97 (t, 1H), 4.1–4.2 (m, 4H), 6.78–6.98 (m, 4H, unresolved), 7.1–7.23 (m, 3H, unresolved).

(b) 2-Ethoxy-3-[4-(2-{3-methoxy-4-methanesulfonyloxyphenyl}ethoxy)phenyl]propanoic Acid 2-Ethoxy-3-[4-(2-{3-methoxy-4-methanesulfonyloxyphenyl}ethoxy)phenyl]propanoic acid ethyl ester was hydrolyzed using the same method as in Example 13 to give 2-ethoxy-3-[4-(2-{3-methoxy-4-methanesulfonyloxyphenyl}ethoxy)phenyl]propanoic acid.

$^1$H-NMR (600 MHz; CDCl$_3$): δ 1.16 (t, 3H), 2.92–2.97 (m, 1H), 3.30–3.09 (m, 3H), 3.16 (s, 3H), 3.39–3.45 (m, 1H), 3.57–3.63 (m, 1H), 3.87 (s, 3H), 4.01–4.05 (m, 1H), 4.15 (t, 2H), 6.81 (d, 2H, J=7.8 Hz), 6.87 (d, 1H, J=7.8 Hz), 6.93 (s, 1H), 7.15 (d, 2H, J=7.8 Hz), 7.22 (d, 1H, J=7.8 Hz). $^{13}$C-NMR (150 MHz; CDCl3): δ 15.2, 35.9, 38.0, 38.4, 56.2, 67.0, 68.4, 79.9, 114.0, 114.6, 121.7, 124.6, 129.1, 130.8, 137.2, 139.3, 151.4, 157.8, 176.0.

Example 38

3-{4-[2-(4-tert-Butoxycarbonylaminophenyl)ethoxy] phenyl}-2-ethoxypropanoic Acid Ethyl Ester (a) 3-(4-Benzyloxyphenyl)-2-ethoxyacrylic Acid Ethyl Ester Tetramethylguanidine (42.3 g; 0.37 mole) was slowly added to a solution of 4-benzyloxybenzaldehyde (75.6 g; 0.36 mole) and (1,2-diethoxy-2-oxoethyl) (triphenyl) phosphonium chloride (130.7 g; 0.304 mole) dissolved in chloroform (800 ml) at 0° C. After stirring at room temperature over night, the solvent was evaporated in vacuo. The residue was dissolved in diethyl ether, insoluble material was filtered off and the filtrate was washed with sodium bicarbonate and dried (magnesium sulfate). The procedure was repeated once and thereafter the crude product was stirred over night with a sodium bisulfite saturated water solution. The solid material was filtered off, the product was extracted with diethyl ether, dried (magnesium sulfate) and the solvent was evaporated in vacuo to give 85 g (yield 73%) of 3-(4-benzyloxyphenyl)-2-ethoxyacrylic acid ethyl ester.

$^1$H-NMR (300 MHz; CDCl$_3$): δ 1.35 (m, 6H), 4.0 (q, 2H), 4.3 (q, 2H), 5.05 (s, 2H), 6.95 (s+m unresolved, 1+3H), 7.3–7.45 (m, 5H), 7.75 (d, 2H). $^{13}$C-NMR (125 MHz; CDCl$_3$): δ 14.4, 15.6, 61.0, 67.5, 70.0, 114.8, 124.0, 126.7, 127.5, 128.1, 128.6, 131.7, 136.7, 143.1, 159.2, 165.0.

(b) 4-(2-Hydroxyethyl)phenylcarbamic Acid tert-Butyl Ester

Di-tert-butyl dicarbonate (7.95 g; 36 mmole) was added to a mixture of p-aminophenethyl alcohol (5 g; 36 mmole) in tetrahydrofuran at 0° C. After stirring at room temperature over night, the solvent was evaporated in vacuo to give 8 g (yield 94%) of 4-(2-hydroxyethyl)phenylcarbamic acid tert-butyl ester.

$^1$H-NMR (400 MHz; DMSO-d$_6$): δ 1,5 (s, 9H), 2,65 (dd, 2H), 3,55 (dd, 2H), 4,6 (s, br, 1 OH), 7,1 (unresolved, 2H), 7,35 (unresolved, 2H), 9,1 (s, 1NH). $^{13}$C-NMR (100 MHz; DMSO-d$_6$): δ 28.3, 38.6, 62.5, 78.9, 118.3, 129.1, 133.2, 136.6, 153.0.

(c) 3-{4-[2-(4-tert-Butoxycarbonylaminophenyl)ethoxy]phenyl}-2-ethoxypropanoic Acid Ethyl Ester 4-(2-Hydroxyethyl)phenylcarbamic acid tert-butyl ester (1.03 g; 4.34 mmole) and 2-ethoxy-3-(4-hydroxyphenyl)propanoic acid ethyl ester (described in Example 20b) (1.03 g; 4.34 mmole) were dissolved in dichloromethane under argon at room temperature. Azodicarbonyl dipiperidine (1.65 g; 6.5 mmole) and thereafter triphenylphosphine (1.37 g; 5.2 mmole) were added. After stirring at room temperature for 6 hours the solvent was evaporated in vacuo. Purification by chromatography on silica gel using heptane-:ethyl acetate (2:1) as eluant gave 1.78 g (yield 89%) of 3-{4-[2-(4-tert-butoxycarbonylaminophenyl)ethoxy]phenyl}-2-ethoxypropanoic acid ethyl ester.

$^1$H-NMR (400 MHz; CDCl$_3$): δ 1.17 (t, 3H, J=7 Hz), 1.23 (t, 3H, J=7 Hz), 1.53 (s, 9H), 2.94–2.97 (m, 2H), 3.03 (t, 2H, J=7.1 Hz), 3.31–3.40 (m, 1H), 3.56–3.65 (m, 1H), 3.95–4.0 (m, 1H), 4.11 (t, 2H, J=7.1 Hz), 4.17 (q, 2H, J=7 Hz), 6.60 (s, 1NH), 6.81 (dm, 2H, J=8.3 Hz, unresolved), 7.15 (dm, 2H, J=8.3 Hz, unresolved), 7.20 (dm, 2H, J=8.3 Hz, unresolved), 7.31 (dm, 2H, J=8.3 Hz, unresolved). $^{13}$C-NMR (100 MHz; CDCl$_3$): δ 14.1, 15.0, 28.3, 35.0, 38.4, 60.7, 66.1, 68.6, 80.26, 80.32, 114.3, 118.7, 128.2, 129.4, 130.3, 132.8, 136.7, 152.8, 157.5, 172.4.

Example 39

3-{4-[2-(4-tert-Butoxycarbonylaminophenyl)ethoxy]phenyl}-2-ethoxypropanoic Acid

Lithium hydroxide hydrate (77 mg; 1.85 mmole) in water (5.5 ml) was slowly added to a solution of 3-{4-[2-(4-tert-butoxycarbonylaminophenyl)ethoxy]phenyl}-2-ethoxypropanoic acid ethyl ester (described in Example 38) (0.77 g; 1.68 mmole) in tetrahydrofuran (7.6 ml). After stirring at room temperature for 4 hours the reaction mixture was kept in a freezer for 4 days. Tetrahydrofuran was removed by evaporation in vacuo. More water was added and the mixture was acidified with hydrochloric acid to pH1. The product was extracted with ethyl acetate, washed twice with water, dried (sodium sulfate), filtered and the solvent was evaporated in vacuo to give 0.712 g (98.7% yield) of 3-{4-[2-(4-tert-butoxycarbonylaminophenyl)ethoxy]phenyl}-2-ethoxypropanoic acid.

$^1$H-NMR (400 MHz; CDCl$_3$): δ 1.18 (t, 3H, J=7 Hz), 1.54 (s, 9H), 2.93–3.10 (m, 4H), 3.36–3.45 (m, 1H), 3.60–3.69 (m, 1H), 4.02–4.07 (m, I H), 4.12 (t, 2H, J=7 Hz), 6.83 (dm, 2H, J=8.8 Hz, unresolved), 7.15–7.23 (m, 4H), 7.27–7.34 (m, 2H), 10.28 (bs, 1NH). $^{13}$C-NMR (100 MHz; CDCl$_3$): δ 15.0, 28.3, 35.2, 38.0, 66.7, 68.8, 79.9, 80.7, 114.6, 119.1, 129.0, 129.4, 130.4, 133.1, 136.8, 153.2, 157.8, 175.3.

Example 40

3-[4-{2-(4-[tert-Butoxycarbonyl(methyl)amino]phenyl)ethoxy}phenyl]-(S)-2-ethoxypropanoic Acid (a) 2-[4-(tert-Butoxycarbonylamino)phenyl]ethyl-4-methylbenzenesulfonate 4-(2-Hydroxyethyl)phenylcarbamic tert-butyl ester (described in Example 38b) (170 g; 0.716 mole) was suspended in dichloromethane (1.7 l) and placed in an ice bath. Pyridine (113 g; 1.43 mole) was added giving a clear yellow solution. p-Toluenesulfonyl chloride (205 g; 1.07 mole) was dissolved in dichloromethane (850 ml) and added slowly with stirring to the reaction mixture during 45 minutes. The reaction mixture was allowed to reach room temperature over night. The solution was then washed with water (4×1 L) and dried with magnesium sulfate. The solvent was evaporated under reduced pressure until the weight was 440 g. The remaining brownish oil was slowly poured into heptane (1.6 L) with vigorous stirring. After approx. 20 seconds the oil started to crystallize. The heavy precipitate was filtered off, washed with heptane (200 ml) and dried in vacuo at 40° C. over night. This procedure gave 274 g (97.8% yield) of crude 2-[4-(tert-butoxycarbonylamino)phenyl]ethyl-4-methylbenzenesulfonate.

A sample of the crude product (8 g) was recrystallized from ethanol (30 ml) and water (3 ml) giving 7.1 g (88.8% yield) of pure 2-[4-(tert-butoxycarbonylamino)phenyl]ethyl-4-methylbenzenesulfonate.

$^1$H-NMR (500 MHz; CDCl$_3$): δ 1.55 (s, 9H), 2.47 (s, 3H), 2.93 (t, 2H, J=7.0 Hz), 4.20 (t, 2H, J=7.0 Hz), 6.45 (s, 1NH), 7.05 (d, 2H), 7.24–7.34 (m, 4H), 7.72 (d, 2H). $^{13}$C-NMR (100 MHz; CDCl$_3$): δ 21.6, 28.3, 34.7, 70.7, 80.5, 118.7, 127.8, 129.4, 129.7, 130.7, 133.0, 137.2, 144.6, 152.7.

(b) 2-[4-{tert-Butoxycarbonyl(methyl)amino}phenyl]ethyl-4-methylbenzenesulfonate 2-[4-(tert-Butoxycarbony)amino)phenyl]ethyl-4-methylbenzenesulfonate (0.5 g; 1.28 mmole) was dissolved in tetrahydrofuran (10 ml). Iodomethane (0.906 g; 6.38 mmole) was added followed by sodium hydride (0.061 g; 2.54 mmole). The reaction mixture was stirred at room temperature for 3 hours and then evaporated. The residue was extracted with diethyl ether and water. The organic phase was dried and evaporated and 0.52 g (96.5% yield) of 2-[4-{tert-butoxycarbonyl(methyl)amino}phenyl]ethyl-4-methylbenzenesulfonate was obtained.

$^1$H-NMR (300 MHz; CDCl$_3$): δ 1.45 (s, 9H), 2.44 (s, 3H), 2.93 (t, 2H), 3.23 (s, 3H), 4.19 (t, 2H), 7.05–7.15 (m, 4H), 7.30 (d, 2H), 7.71 (d, 2H).

(c) 3-(4-Benzyloxyphenyl)-2-ethoxypropanoic Acid Ethyl Ester 3-(4-Benzyloxyphenyl)-2-ethoxyacrylic acid ethyl ester (described in Example 38a) (0.5 g; 1.5 mmole) was hydrogenated at atmospheric pressure using rhodium on charcoal (5%; 50 mg) as catalyst in methanol (20 ml). The crude product was purified by chromatography using heptane-:ethyl acetate (5:1) as eluant to give 50 mg (yield 10%) of 3-(4-benzyloxyphenyl)-2-ethoxypropanoic acid ethyl ester.

¹H NMR (300 MHz; CDCl₃): δ 7.47–7.30 (m, 5H), 7.17 (d, J=8.8, 2H), 6.91 (d, J=8.8 Hz, 2H), 5.06 (s, 2H), 4.17 (q, J=7.2 Hz, 2H), 3.98 (t, J=6.6 Hz, 1H), 3.61 (dq, J=8.9 and 6.8 Hz, 1H), 3.36 (dq, J=8.9 and 6.8 Hz, 1H), 2.97 (d, J=6.6 Hz, 2H), 1.22 (t, J=7.2 Hz, 3H), 1.18 (t, J=6.8 Hz, 3H). ¹³C NMR (75 MHz; CDCl₃): δ 172.6, 157.6, 137.1, 130.4, 129.5, 128.6, 127.9, 127.5, 114.6, 80.4, 70.0, 66.2, 60.8, 38.5, 15.1, 14.2.

(d) 3-(4-Benzyloxyphenyl)-2-ethoxypropanoic Acid

Lithium hydroxide hydrate (7.4 g; 177 mmole) dissolved in water (150 ml) was added to a solution of 3-(4-benzyloxyphenyl)-2-ethoxypropanoic acid ethyl ester (23.25 g; 70.8 mmole) in dioxane (150 ml). After stirring at room temperature over night dioxane was evaporated in vacuo, water was added and the mixture was extracted with ethyl acetate. The water phase was acidified with hydrochloric acid (1 N) and extracted with ethyl acetate. The organic phase was washed with water and brine, dried and the solvent was evaporated in vacuo to give 21.1 g (yield 99.2%) of 3-(4-benzyloxyphenyl)-2-ethoxypropanoic acid.

¹H NMR (300 MHz; CDCl₃): δ 1.15 (t, 3H), 2.9–3.1 (m, 2H), 3.35–3.45 (m, 1H), 3.6–3.7 (m, 1H), 3.95–3.41 (m, 1H), 5.05 (s, 2H), 6.95 (d, 2H), 7.2 (d, 2H), 7.25–7.5 (m, 5H). ¹³C NMR (75 MHz; CDCl₃): δ 15.0, 38.1, 66.6, 70.0., 79.9, 114.7, 127.5, 128.0, 128.6, 129.3, 130.5, 137.1, 157.7, 176.3.

(e) 3-(4-Benzyloxyphenyl)-(S)-2-ethoxy-N-(2-hydroxy-(R)-1-phenylethyl)propanoic Amide and 3-(4-Benzyloxyphenyl)-(R)-2-ethoxy-N-(2-hydroxy-(R)-1-phenylethyl)propanoic Amide EDC (2.03 g; 10.61 mmole), diisopropylethylamin (1.84 ml; 10.61 mmole) and HOBtxKH₂O (1.43 g; 10.61 mmole) were added to a solution of 3-(4-benzyloxyphenyl)-2-ethoxypropanoic acid (2.92 g; 9.74 mmole) in dry dichloromethane (30 ml) cooled on an ice bath. After 30 minutes the ice bath was removed and (R)-phenylglycine and (1.46 g; 10.61 mmole) was added. After stirring at room temperature over night ethyl acetate (100 ml) was added and the mixture was washed with potassium hydrogensulfate (1 M), saturated sodium bicarbonatesolution, sodium carbonate solution and water. The organic phase was dried (sodium sulfate), filtered and solvent was evaporated in vacuo. The crude product was purified by chromatography on silica gel using ethyl acetate:heptane to give 1.5 g (yield 37%) of 3-(4-benzyloxyphenyl)-(S)-2-ethoxy-N-(2-hydroxy-(R)-1-phenylethyl)propanoic amide and 1.25 g (yield 31%) of 3-(4-benzyloxyphenyl)-(R)-2-ethoxy-N-(2-hydroxy-(R)-1-phenylethyl)propanoic amide.

3-(4-Benzyloxyphenyl)-(S)-2-ethoxy-N-(2-hydroxy-(R)-1-phenylethyl)propanoic amide ¹H NMR (400 MHz; CDCl₃): δ 7.43–7.27 (m, 8H), 7.22 (d, J=8.3 Hz, 4H), 7.13 (d, NH, J=7.8 Hz, 1H), 6.96 (d, J=8.3 Hz, 1H), 5.08 (s, 2H), 5.01 (m, 1H), 3.99 (dd, J=6.8 and 3.9 Hz, 1H), 3.69 (m, 2H), 3.50 (q, J=6.8 Hz, 2H), 3.15 (dd, J=14.2 and 3.9 Hz, 1H), 2.97 (dd, J=14.2 and 6.8 Hz, 1H), 2.94 (m, OH, 1H), 1.16 (t, J=6.8 Hz, 3H). ¹³C NMR (100 MHz; CDCl₃): δ 172.3, 157.5, 138.9, 137.0, 130.7, 129.4, 128.6, 128.4, 127.7, 127.6, 127.3, 126.5, 114.4, 81.0, 69.8, 66.3, 66.0, 55.3, 37.8, 15.1.

3-(4-Benzyloxyphenyl)-(R)-2-ethoxy-N-(2-hydroxy-(R)-1-phenylethyl)propanoic amide ¹H NMR (400 MHz; CDCl₃): δ 7.49–7.20 (m, 9H), 7.13 (d, J=8.8 Hz, 4H), 7.08 (d, J=8.3 Hz, 4H), 6.86 (d, J=8.8 Hz, 1H), 5.04 (s, 2H), 5.01 (m, 1H), 4.01 (dd, J=6.8 and 3.9 Hz, 1H), 3.83 (m, 2H), 3.57 (m, 2H), 3.16 (m, OH, 1H), 3.09 (dd, J=14.2 and 3.9 Hz, 1H), 2.91 (dd, J=14.2 and 6.8 Hz, 1H), 1.21 (t, J=6.8 Hz, 3H). ¹³C NMR (100 MHz; CDCl₃): δ 172.3, 157.4, 138.6, 137.0, 130.6, 129.3, 128.5, 128.4, 127.8, 127.4, 127.3, 126.4, 114.4, 81.1, 69.8, 66.4, 66.1, 54.9, 37.5, 15.1.

(f) 3-(4-Benzyloxyphenyl)-2-(S)-ethoxypropanoic Acid 3-(4-Benzyloxyphenyl)-(S)-2-ethoxy-N-2-hydroxy-(R)-1-phenylethyl)propanoic amide (8.9 g; 21.22 mmole) was hydrolyzed with concentrated sulfiuric acid (27 ml) in water (104 ml) and dioxane (104 ml) at 90° C. for 5 hours. The reaction mixture was poured into water (220 ml) and extracted with ethyl acetate. The organic phase was washed with brine, dried (sodium sulfate) and the solvent was evaporated in vacuo to give 6.85 g of a mixture of 3-(4-benzyloxyphenyl)-2-(S)-ethoxypropanoic acid and (S)-2-ethoxy-3-(4-hydroxyphenyl)propanoic acid which was used without further purification.

¹H NMR (400 MHz; CDCl₃): δ 7.47–7.30 (m, 5H), 7.19 (d, J=8.8, 2H), 6.93 (d, J=8.8 Hz, 2H), 5.10 (s, 2H), 4.06 (dd, J=7.8 and 4.4 Hz, 1H), 3.64 (dq, J=9.8 and 6.8 Hz, 1H), 3.44 (dq, J=9.8 and 6.8 Hz, 1H), 3.09 (dd, J=14.2 and 4.4 Hz, 1H), 2.98 (dd, J=14.2 and 7.8 Hz, 1H), 1.19 (t, J=6.8 Hz, 3H).

(g) 3-(4-Benzyloxyphenyl)-2-(S)-ethoxypropanoic Acid Ethyl Ester.

Hydrogen chloride (g) was bubbled through a solution of 3-(4-benzyloxyphenyl)-2-(S)-ethoxypropanoic acid (6.85 g; 22.8 mmole) in ethanol (400 ml). Thionyl chloride (2 ml; 27.4 mmole) was added slowly and the reaction mixture was refluxed for 2 hours. The solvent was evaporated to give 8 g of a mixture of 3-(4-benzyloxyphenyl)-2-(S)-ethoxypropanoic acid ethyl ester and (S)-2-ethoxy-3-(4-hydroxyphenyl)propanoic acid ethyl ester which was used without further purification.

¹H NMR (300 MHz; CDCl₃): δ 7.47–7.30 (m, 5H), 7.17 (d, J=8.8, 2H), 6.91 (d, J=8.8 Hz, 2H), 5.06 (s, 2H), 4.17 (q, J=7.2 Hz, 2H), 3.98 (t, J=6.6 Hz, 1H), 3.61 (dq, J=8.9 and 6.8 Hz, 1H), 3.36 (dq, J=8.9 and 6.8 Hz, 1H), 2.97 (d, J=6.6 Hz, 2H), 1.22 (t, J=7.2 Hz, 3H), 1.18 (t, J=6.8 Hz, 3H). ¹³C NMR (75 MHz; CDCl₃): δ 172.6, 157.6, 137.1, 130.4, 129.5, 128.6, 127.9, 127.5, 114.6, 80.4, 70.0, 66.2, 60.8, 38.5, 15.1, 14.2.

(h) (S)-2-Ethoxy-3-(4-hydroxyphenyl)propanoic Acid Ethyl Ester 3-(4-Benzyloxyphenyl)-2-(S)-ethoxypropanoic acid (7.13 g; 21.7 mmole) was hydrogenated at atmospheric pressure for 2 hours in ethyl acetate (70 ml) using Pd/C as catalyst. Purification by chromatography on silica gel using toluene:ethyl acetate as eluant gave 3.83 g (yield in 3 step 76%) of (S)-2-ethoxy-3-(4-hydroxyphenyl)propanoic acid ethyl ester.

¹H-NMR (400 MHz; CDCl₃): δ 1.18 (t, 3H, J=6.8 Hz), 1.24 (t, 3H, J=7 Hz), 2.96 (d, 2H, J=6.5 Hz), 3.34–3.43 (m, 1H), 3.57–3.66 (m, 1H), 4.00 (t, 1H, 6.5 Hz), 4.18 (q, 2H, J=7 Hz), 5.30 (s, 1 OH), 6.74 (dm, 2H, J=8.5 Hz, unresolved), 7.10 (dm, 2H, J=8.5 Hz, unresolved). ¹³C-NMR (100 MHz; CDCl₃): δ 14.2, 15.0, 38.4, 60.9, 66.2, 80.4, 115.1, 129.0, 130.5, 154.5, 172.7.

(i) 3-[4-{2-(4-[tert-Butoxycarbonyl(methyl)amino]phenyl)ethoxy}phenyl]-(S)-2-ethoxypropanoic Acid Sodium hydroxide (0.044 g; 1.1 mmole) was pulverized and dissolved in DMSO (10 ml). (S)-2-ethoxy-3-(4-hydroxyphenyl)propanoic acid ethyl ester (0.2 g; 0.84 mmole) was added and the mixture was stirred for 10 minutes before addition of 2-[4-{tert-butoxycarbonyl (methyl)amino}phenyl]ethyl-4-methylbenzenesulfonate (0.34 g; 0.84 mmole). The reaction mixture was stirred at room temperature for 4 hours and then according to LC-MS all the starting materials were consumed and the corresponding ester was formed. Water (10 ml), tetrahydrofuran (5 ml) and sodium hydroxide (0.9 g; 22.5 mmole) were added and the mixture was stirred over night and then concentrated by evaporation. The residue was treated with ethyl acetate and water. The phases were separated and the water phase extracted twice with ethyl acetate. The organic phases were combined, dried with sodium sulfate and evaporated. The crude product was chromatographed with dichloromethane:methanol (95:5) as eluant. The product, an oil, was dissolved in water and a small amount of ethanol and acetonitrile. The solution was cooled by liquid nitrogen. Freeze drying for three days gave a pure solid compound, 0.19 g (51% yield) of 3-[4-{2-(4-[tert-butoxycarbonyl(methyl)amino]phenyl)ethoxy}phenyl]-(S)-2-ethoxypropanoic acid as a white solid substance $^1$H-NMR (500 MHz; CD$_3$OD): δ 1.10 (t, 3H), 1.45 (s, 9H), 2.86 (m, 1H), 3.01–3.04 (m, 3H), 3.21 (s, 3H), 3.32 (m, 1H), 3.63 (m, 1H), 3.93 (m, 1H), 4.12 (m, 2H), 6.80 (d, 2H), 7.16–7.20 (m, 4H), 7.28 (d, 2H). $^{13}$C-NMR (125.7 MHz; CDCl$_3$): δ 15.3, 28.6, 36.4, 38.0, 40.4, 66.8, 69.5, 81.5, 115.2, 126.8, 130.3, 131.3, 137.6, 143.2, 156.5, 158.7.

Example 41

(S)-2-ethoxy-3-(4-[2-{4-(methoxycarbonylamino)phenyl}ethoxy]-phenyl)propanoic Acid Ethyl Ester (a) 3-{4-[2-(4-tert-Butoxycarbonylaminophenyl)ethoxy]phenyl}-(S)-2-ethoxypropanoic Acid Ethyl Ester 2-[4-(tert-Butoxycarbonylamino)phenyl]ethylmethanesulfonate (described in Example40a) (52.9 g; 0.168 mmole), (S)-2-ethoxy-3-(4-hydroxyphenyl)propanoic acid ethyl ester (described in Example 40h) (40 g; 0.168 mmole) and potassium carbonate (69.5 g; 0.503 mmole) were mixed in acetonitrile (1200 ml) and refluxed over night. Another portion of 2-[4-(tert-butoxycarbonylamino)phenyl]ethylmethanesulfonate (2.5 g; 7.9 mmole) was added. The reaction mixture was refluxed for 8 more hours then filtered. Evaporation of the filtrate gave 76.6 g 3-{4-[2-(4-tert-butoxycarbonylaminophenyl)ethoxy]phenyl}-(S)-2-ethoxypropanoic acid ethyl ester.

This batch of 3-{4-[2-(4-tert-butoxycarbonylaminophenyl)ethoxy]phenyl}-(S)-2-ethoxypropanoic acid ethyl ester (76.6 g) was combined with another batch of 3-{4-[2-(4-tert-butoxycarbonylaminophenyl)ethoxy]phenyl}-(S)-2-ethoxypropanoic acid ethyl ester (74.1 g) and purified twice by flash chromatography on silica gel. First with toluene followed by methanol as eluants and the second time toluene with ethyl acetate (2–5%). This procedure gave 69.9 g of pure 3-{4-[-(tert-3-{4-[2-(4-tert-butoxycarbonylaminophenyl)ethoxy]phenyl}-(S)-2-ethoxypropanoic acid ethyl ester.

$^1$H-NMR (400 MHz; CDCl$_3$) d 1.16 (t, 3H), 1.22 (t, 3H), 1.51 (s, 9H), 2.94 (d, 2H), 3.02 (t, 2H), 3.31–3.38 (m, 1H), 3.55–3.63 (m, 1H), 3.95 (t, 1H), 4.10 (t, 2H), 4.16 (q, 2H), 6.45 (bs, 1H), 6.8 (d, 2H), 7.13 (d, 2H), 7.13 (d, 2H), 7.19 (d, 2H), 7.29 (d, 2H). 3-{4-[2-(4-Aminophenyl)ethoxy]

(b) 3-}4-[2-(4-Aminophenyl)ethoxy]phenyl}-(S)-2-ethoxypropanoic Acid Ethyl Ester Hydrochloride Trifluoroacetic acid (12 ml; 0.0706 mole) was added to a solution of 3-{4-[2-(4-tert-butoxycarbonylaminophenyl)ethoxy]phenyl}-(S)-2-ethoxypropanoic acid ethyl ester (30 g; 0.065 mole) in dichloromethane (150 ml). The reaction mixture was stirred over night at room temperature and then washed three times with water. The organic phase was dried with magnesium sulfate and evaporated. $^1$H-NMR of the product showed a mixture of product and starting material. The crude product (27.3 g) was redissolved in ethyl acetate, ethyl acetate saturated with hydrochloric acid (500 ml) was added and the mixture was stirred over night at room temperature. Evaporation gave 24.7 g (96.5% yield) of 3-{4-[2-(4-aminophenyl)ethoxy]phenyl}-(S)-2-ethoxypropanoic acid hydro chloride.

$^1$H-NMR (400 MHz, CDCl$_3$): d 1.14 (t, J=7 Hz, 3H), 1.20 (t, J=7 Hz, 3H), 2.91–2.93 (m, 2H), 3.02 (t, J=7 Hz, 2H), 3.29–3.36 (m, 1H), 3.54–3.61 (m, 1H), 3.94 (dd, J=7.3, 5.8 Hz, 1H), 4.08 (t, J=7 Hz, 2H), 4.14 (q, J=7 Hz, 2H), 6.76 (d, J=8.8 Hz, 2H), 7.12 (d, J=8.8 Hz, 2H), 7.27 (d, J=8.3 Hz, 2H), 7.45 (d, J=8.3 Hz, 2H). $^{13}$C-NMR (100 MHz, CDCl$_3$): d 14.18, 15.02, 35.22, 38.40, 60.77, 66.16, 68.00, 80.31, 114.29(2C), 123.39(2C), 128.16, 129.50, 130.39(2C), 130.42(2C), 139.69, 157.29, 172.53.

(c) (S)-2-Ethoxy-3-(4-[2-{4-(methoxycarbonylamino)phenyl}ethoxy]phenyl)propanoic Acid Ethyl Ester 3-{4-[2-(4-Aminophenyl)ethoxy]phenyl}-(S)-2-ethoxypropanoic acid ethyl ester hydro chloride (0.55 g; 1.4 mmole) was dissolved in tetrahydrofuran (5 ml) and methyl chloroformate (0.534 g; 5.68 mmole) was added slowly. The reaction mixture was continuously checked with HPLC and after 6 days was all the starting material consumed. Water was added to the mixture, tetrahydrofuran was evaporated and the residue extracted three times with ethyl acetate. The organic phase was dried with magnesium sulfate and evaporated and 0.525 g (90.2%) of (S)-2-ethoxy-3-(4-[2-{4-(methoxycarbonylamino)phenyl}ethoxy]phenyl)propanoic acid ethyl ester was obtained.

$^1$H-NMR (600 MHz; CDCl$_3$): δ 1.15 (t, 3H), 1.22 (t, 3H), 2.90–2.97 (m, 2H), 3.03 (t, 2H), 3.31–3.37 (m, 1H), 3.55–3.62 (m, 1H), 3.77 (s, 3H), 3.95 (q, 1H), 4.11 (t, 3H), 4.16 (q, 2H), 6.60 (bs, NH), 6.80 (d, 2H), 7.13 (d, 2H), 7.21 (d, 2H), 7.32 (bd, 2H) $^{13}$C-NMR (150 MHz; CDCl$_3$): δ 14.4, 15.5, 35.3, 38.7, 45.2, 52.5, 61.0, 66.4, 68.9, 80.6, 114.5, 129.5, 129.8, 130.6, 157.8, 172.8, 179.7.

Example 42

(S)-2-Ethoxy-3-(4-[2-{4-(methoxycarbonylamino)phenyl]-ethoxy]phenyl)propanoic Acid (S)-2-Ethoxy-3-(4-[2-{4-(methoxycarbonylamino)phenyl]ethoxy]phenyl)propanoic acid ethyl ester (described in Example 41) (0.52 g; 1.25 mmole) was dissolved in tetrahydrofuran (10 ml) and lithium hydroxide (0.034 g; 1.42 mmole) dissolved in water (2 ml) was added slowly. The reaction mixture was stirred over night, hydrochloric acid (1 M, 1 ml) was added and tetrahydrofuran evaporated. The residue was extracted three times with ethyl acetate. The organic phase was dried with magnesium sulfate and evaporated and 0.47 g (99% yield) (S)-2-ethoxy-3-[4-{2-[4-(methoxycarbonylamino)phenyl)ethoxy]phenyl}propanoic acid was obtained.

$^1$H-NMR (600 MHz; CDCl$_3$): δ 1.16 (t, 3H), 2.91–3.05 (m, 2H), 3.03 (t, 2H), 3.38–3.45 (m, 1H), 3.56–3.63 (m, 1H), 3.77 (s, 3H), 4.03 (q, 1H), 4.11 (t, 3H), 6.80 (d, 2H), 7.14 (d, 2H), 7.21 (d, 2H), 7.30 (bs, 2H). $^{13}$C-NMR (150 MHz; CDCl$_3$): δ 15.3, 35.4, 38.1, 52.6, 67.0, 68.9, 80.0, 114.7, 129.0, 129.8, 130.7, 157.9, 175.6.

Example 43

3-[4-{2-(4-[tert-Butoxycarbonylamino]phenyl)ethoxy}phenyl]-2-ethylsulfanylpropanoic Acid Methyl Ester (a) 3-(4-Benzyloxyphenyl)-2-ethylsulfanyl Propanoic Acid Methyl Ester Potassium hydroxide (0.092 g; 1.64 mmole) was dissolved in methanol. Ethanethiol (0.133 g; 2.14 mmole) and 3-(4-benzyloxyphenyl)-2-chloropropanoic acid methyl ester (0.5 g; 1.64 mmole) were added. The reaction mixture was stirred at room temperature over night. Diethyl ether (15 ml) was added. The mixture was filtered and evaporated. The residue was purified by adding active charcoal in methanol. The mixture was stirred for 15 minutes and the active charcoal was filtered off. Evaporation of the solvent gave 0.47 g (86.7% yield) of 3-(4-benzyloxyphenyl)-2-ethylsulfanyl propanoic acid methyl ester.

$^1$H-NMR (400 MHz; CDCl$_3$): δ 1.23 (t, 3H), 2.63 (m, 2H), 2.90 (m, 1H), 3.14 (m, 1H), 3.50 (m, 1H), 3.67 (s, 3H), 5.04 (s, 2H), 6.89 (d, 2H), 7.11 (d, 2H), 7.30–7.45 (m, 5H).

(b) 2-Ethylsulfanyl-3-(4-hydroxyphenyl)propanoic Acid Methyl Ester 3-(4-Benzyloxyphenyl)-2-ethylsulfanyl propanoic acid methyl ester (0,37 g; 1.12 mmole) was dissolved in dichloromethane (3.5 ml). Dimethylsulfide (3 ml), was added followed by addition of boron trifluoride etherate (1.6 g; 11 mmole), The reaction mixture was stirred for 3 hours at room temperature and then quenched with water (3 ml). More dichloromethane was added and the phases were separated. The organic phase was washed twice with brine and dried with sodium sulfate. Evaporation of the solvent gave 0.2 g (74.3% yield) of ethylsulfanyl-3-(4-hydroxyphenyl)propanoic acid methyl ester.

$^1$H-NMR (300 MHz; CDCl$_3$): δ 1.23 (t, 3H), 2.62 (q, 2H), 2.90 (m, 1H), 3.11 (m, 1H), 3.51 (m, 1H), 3.68 (s, 3H), 6.73 (d, 2H), 7.05 (d, 2H).

(c) 3-[4-{2-(4-[tert-Butoxycarbonylamino]phenyl)ethoxy}phenyl]-2-ethylsulfanylpropanoic Acid Methyl Ester Sodium hydroxide (0.045 g; 1.25 mmole) was pulverized and added to DMSO (10 ml). 2-Ethylsulfanyl-3-(4-hydroxyphenyl)propanoic acid methyl ester (0.21 g; 0.87 mmole) was added followed by addition of 2-[4-(tert-butoxycarbonylamino)phenyl]ethyl-4-methylbenzenesulfonate (described in Example 40a) (0.342; 0.87 mmole). The reaction mixture was stirred at room temperature for 3 hours then all the starting material were consumed according to LC-MS. Water (10 ml) and tetrahydrofuran (5 ml) were added and the stirring was continued over night. Then the reaction mixture was treated with diethyl ether and water and in order to avoid foam formation diluted hydrochloric acid was added. The phases were separated and the organic phase was washed three times with water. The water phases were combined and washed once again with diethyl ether. All the organic phases were combined, dried with sodium sulfate and evaporated. Chromatography in ether:petroleum ether (1:9 and 1:3) gave 0.18 g (41.4% yield) of 3-[4-{2-(4-[tert-butoxycarbonylamino]phenyl)ethoxy}phenyl]-2-ethylsulfanylpropanoic acid methyl ester.

$^1$H-NMR (400 MHz; CDCl$_3$): δ 1.22 (t, 3H), 1.51 (s, 9H), 2.61 (m, 2H), 2.89 (m, 1H), 3.01 (t, 2H), 3.12 (m, 1H), 3.48 (m, 1H), 3.66 (s, 3H), 4.09 (t, 2H), 6.79 (d, 2H), 7.08 (d, 2H), 7.18 (d, 2H), 7.29 (d, 2H). $^{13}$C-NMR (100 MHz; CDCl$_3$): δ 14.6, 25.9, 28.6, 35.3, 37.3, 48.4, 52.3, 68.9, 80.7, 114.7, 119.0, 129.7, 130.1, 130.4, 133.1, 137.0, 153.0, 157.9, 173.0.

Example 44

3-[4-{2-(4-[tert-Butoxycarbonylamino]phenyl)ethoxy}phenyl]-2-ethylsulfanylpropanoic Acid Sodium hydroxide (0.14 g; 3.5 mmole) was pulverized and added to DMSO (15 ml). 2-ethylsulfanyl-3-(4-hydroxyphenyl)propanoic acid methyl ester (described in Example 43b) (0.21 g, 0.87 mmole) was added and the resulting mixture was stirred at room temperature for 10 minutes before addition of 2-(4-(tert-butoxycarbonylamino)phenyl]ethyl-4-methylbenzenesulfonate (described in Example 40a) (0.342 g; 0.87 mmole). The reaction mixture was stirred at room temperature for 4 hours. Sodium hydroxide (1.08 g; 2.7 mmole) was dissolved in water (15 ml) and added to the reaction mixture followed by addition of tetrahydrofuran (5 ml). The reaction mixture was stirred at room temperature over night. Most of the solvents were evaporated. The residue was treated with diethyl ether and water and the phases were separated. The organic phase was dried with sodium sulfate and evaporated. Chromatography of the residue on silica gel using a gradient system of petroleum ether: diethyl ether (90:10, 75:25, 25;75 and 0:100) gave 0.41 g (34% yield) of 3-[4-{2-(4-[tert-butoxycarbonylamino]phenyl)ethoxy}phenyl]-2-ethylsulfanylpropanoic acid.

$^1$H-NMR (400 MHz; CDCl$_3$): δ 1.02 (t, 3H), 1.50 (s, 9H), 2.44 (m, 2H), 2.77 (m, 1H), 2.92 (m, 2H), 3.15 (m, 1H), 3.44 (m, 1H), 3.96 (m, 2H), 6.68 (d, 2H), 7.03 (d, 2H), 7.10 (d, 2H), 7.23 (d, 2H).

Example 45

3-{4-[2-(4-tert-Butoxycarbonylaminophenyl)ethoxy]phenyl}-2-ethoxypropanoic Acid Benzyl Ester 3-{4-[2-(4-tert-Butoxycarbonylaminophenyl)ethoxy]phenyl}-2-ethoxypropanoic acid (described in Example 39) (1 g; 2.33 mmole) was dissolved in a solution of dichloromethane and triethylamine (0.235 g; 2.56 mmole) and the mixture was cooled to 0° C. Benzyl chloroformate (0.4 g; 2.33 mmole) was added followed by addition of DMAP (0.28 g; 2.33 mmole) after 10 minutes.

The reaction mixture was stirred over night at room temperature and then extracted with saturated sodium hydrogen carbonate, potassium hydrogen sulfate (0.5 M) and brine. The organic phase was dried with sodium sulfate and evaporated. Chromatography on silica gel using dichloromethane with methanol (1%) as eluant gave 0.36 g (29.7%) of 3-{4-[2-(4-tert-butoxycarbonylaminophenyl)ethoxy]phenyl}-2-ethoxypropanoic acid benzyl ester.

$^1$H-NMR (400 MHz; CDCl$_3$): δ 1.18 (t, 3H), 1.53 (s, 9H), 2.98 (d, 2H), 3.07 (t, 2H), 3.32–3.4 (m, 1H), 3.56–3.65 (m, 1H), 4.03 (t, 1H), 4.16 (t, 2H), 5.15 (s, 2H), 6.53 (bs, 1H), 6.8 (d, 2H), 7.12 (d, 2H), 7.23 (d, 2H), 7.25–7.38 (m, 7H). $^{13}$C-NMR (100 MHz; CD$_3$OD): δ 14.2, 27.6, 34.9, 38.2, 65.9, 66.4, 68.7, 76.6, 80.3, 114.3, 118.8, 128.15, 128.2, 128.3, 128.8, 129.2, 130.3, 133.0, 135.8, 137.7, 154.2, 158.0, 172.8.

Example 46 tert-Butyl 4-(2-[4-{2-Ethoxy-3-oxopropyl}phenoxy]ethyl)phenylcarbamate

3-{4-[2-(4-tert-Butoxycarbonylaminophenyl)ethoxy]phenyl}-2-ethoxypropanoic acid ethyl ester (described in Example 38) (3.78 g; 8.2 mmole) was dissolved in dry dichloromethane and the solution was cooled to −78° C. DIBAL (20%, 15.9 ml; 19 mmole) was added slowly. The reaction mixture was stirred at −78° C. and followed by TLC. After 4 hours another portion of DIBAL (15.9 ml; 19 mmole) was added.

The reaction was quenched with aqueous ammonium chloride and the addition resulted in a heavy precipitate. The mixture was filtered through hyflo and the filtrate evaporated. The residue was redissolved in ethyl acetate and chromatography on silica gel with ethyl acetate: heptane (gradient 12.5–100% of ethyl acetate) gave 0.9 g (26.3% yield) of tert-butyl-4-(2-[4-{2-ethoxy-3-oxopropyl}phenoxy]ethyl)phenylcarbamate.

$^1$H-NMR (400 MHz; CDCl$_3$): δ 1.19 (t, 3H), 1.53 (s, 9H), 2.80–2.86 (m, 1H), 2.90–2.96 (m, 1H), 3.04 (t, 2H), 3.40–3.50 (m, 1H), 3.55–3.66 (m, 1H), 3.79–3.84 (m, 1H), 4.13 (t, 2H), 6.51 (bs, 1H), 6.83 (d, 2H), 7.14 (d, 2H), 7.21 (d, 2H), 7.31 (d, 2H), 9.68 (s, 1H); $^{13}$C-NMR (100 MHz; CDCl$_3$): δ 15.5, 28.6, 35.4, 36.1, 66.8, 69.0, 80.7, 85.4, 114.7, 119.0, 128.9, 129.7, 130.6, 133.1, 137.0, 153.1, 157.9, 204.0.

Example 47 tert-Butyl 4-[2-(4-{3-[Benzyl(ethyl)amino]-2-ethoxy-3-oxopropyl}phenoxy)ethyl] phenylcarbamate 3-{[2-(4-tert-Butoxycarbonylaminophenyl)ethoxy] phenyl}-2-ethoxypropanoic acid (described in Example 39) (6.09 g; 14.2 mmole) was dissolved in acetonitrile (150 ml) and the solution was cooled to 0° C. DCC (3.51 g; 17 mmole), HO-Su (1.96 g; 17 mmole) and DIPEA (2.2 g; 17 mmole) were added and stirred for 15 minutes before addition of N-ethylbenzylamine (2.72 g; 17 mmole). The reaction mixture was stirred over night and then filtered and evaporated. Hydrochloric acid (2 M, 200 ml) was added to the residual oil and the obtained mixture was then extracted three times with ethyl acetate. The organic phase was washed with sodium hydrogencarbonate solution, dried with magnesium sulfate and evaporated.

Chromatography of the residue on silica gel with heptane:ethylacetate (1.25–100%) using the gradient elution technique gave 5.32 g (68.5% yield) of tert-butyl 4-[2-(4-{3-[benzyl(ethyl)amino]-2-ethoxy-3-oxopropyl}phenoxy) ethyl]phenylcarbamate. $^1$H-NMR (400 MHz; CDCl$_3$): δ 1.17 (t, 3H), 1.53 (s, 9H), 2.94–3.13 (m, 4H), 3.39–3.47 (m, 1H), 3.58–3.66 (m, 1H), 4.06–4.09 (m, 1H), 4.13 (t, 2H), 6.58 (b, 1H), 6.77–6.85 (m, 3H), 7.17–7.23 (m, 3H), 7.26–7.32 (m, 2H); $^{13}$C-NMR (100 MHz; CDCl$_3$): δ 15.0, 28.4, 35.2, 38.9, 66.9, 68.8, 79.7, 80.6, 113.2, 116.0, 119.1, 121.9, 129.2, 129.4, 133.2, 136.8, 138.3, 153.1, 158.9, 174.4.

Example 48

3-{3-[2-(tert-Butoxycarbonylaminophenyl)ethoxy] phenyl}-2-ethoxypropanoic Acid Ethyl Ester (a) 2-[4-(tert-Butoxycarbonylamino)phenyl] ethylmethanesulfonate 4-(2-Hydroxyethyl)phenylcarbamic acid tert-butylester (described in Example 38b) (2.46 g; 10.38 mmole) was dissolved in dichloromethane (21 ml). Triethylamine (2.17 ml; 15.6 mmole) was added and the mixture was stirred for 20 min and then cooled on an ice-bath. Methanesulphonyl chloride (1.25 g; 10.9 mmole) was added slowly. The reaction mixture was stirred for 3.5 hours and the formed precipitate was filtered off. The filtrate was evaporated and the residue redissolved in ethyl acetate. A new precipitate was formed and filtered off and the filtrate evaporated. Chromatography on silica gel using heptane:ethyl acetate (2:1, 1:1) gave 3 g (100% yield) of 2-[4-(tert-butoxycarbonylamino)phenyl]ethylmethanesulfonate.

$^1$H-NMR (400 MHz; CDCl$_3$): δ 1.52 (s, 9H), 2.87 (s, 3H), 3.01 (t, 2H), 4.39 (t, 2H), 7.16 (d, 2H, J=8.45 Hz), 6.45 (bs, 1H), 7.33 (d, 2H, J=8.45 Hz); $^{13}$C-NMR (100 MHz; CDCl3): δ 28.2, 34.8, 37.1, 70.2, 80.3, 118.6, 129.2, 130.5, 137.3, 152.6.

(b) 3-{3-[2-(4-tert-Butoxycarbonylaminophenyl)ethoxy] phenyl}-2-ethoxypropanoic Acid Ethyl Ester 2-Ethoxy-3-(3-hydroxyphenyl)propanoic acid ethyl ester (0.76 g, 3.2 mmole) was dissolved in acetonitrile (30 ml). Potassium carbonate (0.53 g; 3.8 mmole) was added followed by addition of 2-[4-(4-tert-butoxycarbonylamino) phenyl]ethylmethanesulfonate (1 g; 3.2 mmole). The reaction mixture was refluxed for 4.5 hours and then more acetonitrile (20 ml) was added. The mixture was refluxed over night and then evaporated. The residue was redissolved in water and extracted with ethyl acetate. The organic phase was washed with water and brine, dried with magnesium sulfate and evaporated. Chromatography on silica using ethyl acetate:hexane (1:4) as eluant gave 0.8 g (54.6% yield) of 3-{3-[2-(4-tert-butoxycarbonylaminophenyl)ethoxy] phenyl}-2-ethoxypropanoic acid ethyl ester.

The product was freeze dried before used in the next step.

$^1$H-NMR (400 MHz; CDCl$_3$): δ 1.17 (t, 3H), 1.32 (t, 3H), 1.52 (s, 9H), 2.98 (d, 2H), 3.04 (t, 2H), 3.32–3.4 (m, 1H), 3.57–3.65 (m, 1H), 4.01 (t, 1H), 4.13 (t, 2H), 4.18 (q, 2H), 6.51 (bs, 1H), 6.76 (d, 1H, J=7.98 Hz), 6.79–6.85 (m, 2H), 7.17 (d, 1H, J=7.97 Hz), 7.2 (d, 2H, J=8.28 Hz), 7.31 (d, 2H, J=8.28 Hz). $^{13}$C-NMR (100 MHz; CDCl$_3$): δ 14.4, 15.3, 28.6, 35.5, 39.6, 61.0, 66.4, 68.9, 80.4, 80.6, 113.0, 115.9, 119.0, 122.0, 129.4, 129.7, 133.2, 137.1, 139.0, 153.1, 158.9, 172.7.

Example 49

3-{3-[2-(4-tert-Butoxycarbonylaminophenyl)ethoxy] phenyl}-2-ethoxypropanoic Acid 3-{3-[2-(4-tert-Butoxycarbonylaminophenyl)ethoxy] phenyl}-2-ethoxypropanoic acid ethyl ester (described in Example 48) (0.8 g; 1.74 mmole) was dissolved in tetrahydrofuran (15 ml). Lithium hydroxide hydrate (0.073 g; 1.74 mmole) dissolved in water (5 ml) was added slowly. The reaction mixture was stirred at room temperature for 4.5 hours. More lithium hydroxide hydrate (0.036 g; 0.87 mmole) was added and the stirring continued for 2 more hours. Tetrahydrofuran was carefully evaporated and a large amount of water was added. pH was adjusted to about 12 with sodium hydroxide (2M) and the solution was extracted with ethyl acetate. The water phase was cooled to <10° C., acidified with potassium hydrogensulfate (1 M) and extracted with ethyl acetate. The organic phase was washed with water and dried with sodium sulfate. Evaporation gave 0.53 g (70.9% yield) of 3-{3-[2-(4-tert-butoxycarbonylaminophenyl)ethoxy]phenyl}-2-ethoxypropanoic acid.

$^1$H-NMR (400 MHz; CDCl$_3$): δ 1.17 (t, 3H), 1.53 (s, 9H), 2.94–3.13 (m, 4H), 3.39–3.47 (m, 1H), 3.58–3.66 (m, 1H), 4.06–4.09 (m, 1H), 4.13 (t, 2H), 6.58 (b, 1H), 6.77–6.85 (m, 3H), 7.17–7.23 (m, 3H), 7.26–7.32 (m, 2H); $^{13}$C-NMR (100 MHz; CDCl$_3$): δ 15.0, 28.4, 35.2, 38.9, 66.9, 68.8, 79.7, 80.6, 113.2, 116.0, 119.1, 121.9, 129.2, 129.4, 133.2, 136.8, 138.3, 153.1, 158.9, 174.4.

Example 50

3-[4-{2-(4-[tert-Butoxycarbonylamino]phenyl) ethoxy}phenyl]-2-ethoxy-2-methylpropanoic Acid (a) 3-(4-Benzyloxyphenyl)-2-ethoxy-3-hydroxy-2-methyl Propanoic Acid Ethyl Ester Di-isopropylamine (1.1 ml; 7.78 mmole) and dry tetrahydrofuran (35 ml) were mixed and cooled to −78° C. under nitrogen athmosphere. n-Butyllithium (1.6 M in hexane, 4.7 ml; 7.52 mmole) was added slowly and the reaction mixture was stirred for 15 minutes. 2-Ethoxypropionic acid ethyl ester was dissolved in a small amount of dry tetrahydrofuran and added slowly to the LDA mixture. The solution was stirred for 30 minutes at low temperature and then 4-benzyloxybenzaldehyde was added followed after 2 minutes by addition of saturated ammonium chloride solution (20 ml). The mixture was warmed to room temperature and the layers were separated. The aqueous phase was extracted twice with ether and the organic phases were combined and washed with hydrochloric acid (0.3 M, 100 ml) and brine dried with magnesium sulfate and evaporated. Purification of the residue by chromatography on silica gel using ethyl acetate: toluene (1:9) with triethylamine (0.1%) as eluant gave 1.63 g (68%) of 3-(4-benzyloxyphenyl)2-ethoxy-3-hydroxy-2-methyl propanoic acid ethyl ester.

$^1$H-NMR (400 MHz; CDCl$_3$): δ 1.18 (t, 3H, J=7.0 Hz), 1.26 (t, 3H, 7.1 Hz), 1.41 (s, 3H), 3.26 (br, 1H), 3.44–3.60 (m, 2H), 4.06–4.15 (m, 2H), 4.77 (s, 1H), 5.07 (s, 2H), 6.93 (d, 2H, J=8.8 Hz), 7.30 (d, 2H, J=8.8 Hz), 7.32–7.47 (m, 5H); $^{13}$C-NMR (100 MHz; CDCl$_3$): δ 14.1, 15.6, 17.1, 60.3, 60.8, 69.9, 78.0, 82.9, 114.0, 127.4, 127.8, 128.5, 128.7, 131.5, 137.0, 158.5, 172.4.

(b) 3-(4-Benzyloxyphenyl)-2-ethoxy-2-methyl Propanoic Acid Ethyl Ester 3-(4-Benzyloxyphenyl)-2-ethoxy-3-hydroxy-2-methyl propanoic acid ethyl ester (0.358 g; 1 mmole) and triethylsilane (0.32 ml; 2 mmole) were dissolved in dry dichloromethane (4 ml) and cooled to 0° C. whereafter borontrifluoride etherate (0.284 g; 2 mmole) was added. The reaction mixture was then stirred at 0° C. for 2.5 hours and then quenched by addition of saturated sodium hydrogencarbonate (10 ml) and dichloromethane (10 ml). The aqueous layer was extracted three times with diethyl ether. The organic phases were combined and dried over sodium sulfate. Evaporation of the solvent gave 0.349 g (100% yield) of 3-(4-benzyloxyphenyl)-2-ethoxy-2-methyl propanoic acid ethyl ester.

$^1$H-NMR (400 MHz; CDCl$_3$): δ 1.19–1.26 (m, 6H), 1.31 (s, 3H), 2.97 (s, 2H), 3.38–3.53 (m, 2H), 4.15 (dq, 2H, J=7.1), 5.03 (s, 2H), 6.87 (d, 2H, J=8.7 Hz), 7.12 (d, 2H, J=8.7 Hz), 7.28–7.45 (m, 5H); $^{13}$C-NMR (100 MHz; CDCl$_3$): δ 14.2, 15.7, 20.3, 44.2, 60.0, 60.8, 70.0, 80.8, 114.3, 127.5, 127.9, 128.5, 128.7, 131.4, 137.2, 157.6, 174.2.

(c) 2-Ethoxy-3-(4-hydroxyphenyl)-2-methyl Propanoic Acid Ethyl Ester 3-(4-Benzyloxyphenyl)-2-ethoxy-2-methyl propanoic acid ethyl ester (0.34 g; 0.99 mmole) was hydrogenated for 18 hours at atmospheric pressure in ethyl acetate using Pd/C (0.05 g) as catalyst and then filtered through hyflo. The solvent was evaporated and 0.249 g (98% yield) of 2-ethoxy-3-(4-hydroxyphenyl)-2-methyl propanoic acid ethyl ester was obtained.

$^1$H-NMR (400 MHz; CDCl$_3$): δ 1.21 (t, 3H, J=7.0 Hz), 1.23 (t, 3H, J=7.1 Hz), 1.32 (s, 3H), 2.95 (s, 2H), 3.38–3.54 (m, 2H), 4.14 (dq, 2H, J=7.1), 6.70 (d, 2H, J=8.8 Hz), 7.04 (d, 2H, J=8.8 Hz); $^{13}$C-NMR (100 MHz; CDCl$_3$): δ 14.2, 15.6, 20.3, 44.2, 60.0, 60.9, 80.8, 114.8, 128.2, 131.5, 154.5, 174.4.

(d) 3-[4-{2-(4-[tert-Butoxycarbonylamino]phenyl) ethoxy}phenyl]-2-ethoxy-2-methylpropanoic Acid Sodium hydroxide (0.105 g; 2.63 mmole) was pulverized and dissolved in DMSO (8 ml). To 4 ml of this solution 2-[4-(tert-butoxycarbonylamino)phenyl]ethyl-4-methylbenzenesulfonate (described in Example 40a) (0.515 g; 1.316 mmole) and 2-ethoxy-3-(4-hydroxyphenyl)2-methyl propanoic acid ethyl ester (0.331 g; 1.316 mmole) were added and the mixture was stirred at room temperature over night. The remaining volume (4 ml) of the sodium hydroxide solution and water (1 ml) were added. A precipitate was formed which was dissolved by addition of tetrahydrofuran (1 ml). The mixture was allowed to stand over night and was then evaporated. The residue was redissolved in dichloromethane and water and the phases were separated. The water phase was extracted once more with dichloromethane, acidified with hydrochloric acid (1 M), extracted several times with ethyl acetate and diethyl ether. The organic phases were combined, dried with magnesium sulfate and evaporated. Purification of the crude product by flash chromatography and preparative HPLC gave 0.103 g (17.1% yield) of 3-[4-{2-(4[-tert-butoxycarbonylamino] phenyl)ethoxy}phenyl]-2-ethoxy-2-methyl-propanoic acid.

$^1$H-NMR (600 MHz; CDCl$_3$): δ 1.24 (t, 3H, J=7.0 Hz), 1.46 (s, 3H), 1.52 (s, 9H), 2.36 (s, 2H), 3.02 (t, 2H, J=6.9 Hz), 4.10 (t, 2H, J=6.9 Hz), 6.55 (br, 1H), 6.79 (d, 2H, J=8.6 Hz), 7.08 (d, 2H J=8.6 Hz), 7.14–7.28 (m, 5H), 7.29 (br, 1H); $^{13}$C-NMR (75 MHz; CDCl$_3$): δ 15.5, 20.9, 28.3, 35.1, 42.3, 59.5, 68.6, 80.6, 81.0, 114.2, 118.8, 127.5, 129.4, 131.1, 132.9, 136.7, 153.0, 157.8, 176.1.

Example 51

2-Ethoxy-3-{4-[2-(4-methylcarbamoyloxyphenyl) ethoxy]phenyl}propanoic Acid Ethyl Ester Methyl isocyanate (70 mg; 1.22 mmole) was slowly added to a mixture of triethyl amine (180 mg; 1.17 mmole) and 2-ethoxy-3-{4-[2-(4-hydroxyphenyl)ethoxy] phenyl}propanoic acid ethyl ester (described in Example 26b) (418 mg; 1.17 mmole) in dichloromethane (5 ml). After stirring at room temperature for 2.5 hours the excess of methyl isocyanate was evaporated in vacuo and water and dichloromethane were added. The phases were separated. Water and potassium hydrogensulfate (1 M) were added to the organic phase. The phases were separated, the organic phase was evaporated in vacuo and the residue was purified by chromatography on silica using toluene:diethylether (gradient 4:1 to 3:1) as eluant to give 229 mg (yield 47%) of 2-ethoxy-3-{4-[2-(4-methylcarbamoyloxyphenyl)ethoxy] phenyl}propanoic acid ethyl ester.

$^1$H-NMR (400 MHz; CDCl$_3$): δ 1.2 (t, 3H, J=7.0 Hz), 1.26 (t, 3H), 2.87 (d, 3H, J=4.9 Hz), 2.97–3.01 (m, 2H), 3.09 (t, 2H, J=7.0 Hz), 3.35–3.43 (m, 1H), 3.59–3.68 (m, 1H), 3.99–4.03 (m, 1H), 4.16 (t, 2H, J=7.0 Hz), 4.20 (q, 2H), 5.25 (m, 1NH), 6.84 (dm, 2H, J=8.6 Hz, unresolved), 7.09 (dm, 2H, J=8.3 Hz, unresolved), 7.18 (dm, 2H, J=8.6 Hz, unresolved), 7.28 (dm, 2H, J=8.3 Hz, unresolved). $^{13}$C-NMR (100 MHz; CDCl$_3$): δ 14.1, 14.9, 27.5, 35.0, 38.3, 60.6, 66.0, 68.4, 80.2, 114.2, 121.4, 129.2, 129.6, 130.2, 135.1, 149.6, 155.3, 157.4, 172.4.

Example 52

3-[4-{2-(4-[Benzyloxycarbonylamino]phenyl) ethoxy}phenyl]-(S)-2-ethoxypropanoic Acid Ethyl Ester 3-{4-[2-(4-Aminophenyl)ethoxy]phenyl}-(S)-2-ethoxypropanoic acid ethyl ester hydro chloride (described in Example 41b) (0.6 g; 1.67 mmole, triethylamine (0.17 g; 1.67 mmole) and benzylchloroformate (0.28 g; 1.67 mmole) were mixed in tetrahydrofuran. The reaction mixture was stirred at room temperature over night and then evaporated. The residue was treated with sodium hydrogencarbonate solution and diethyl ether. The organic phase was dried with magnesium sulfate and evaporated. According to NMR spectra there was starting material left. The residue was therefore dissolved in tetrahydrofuran and triethylamine and benzylchloroformate were added. The reaction mixture was stirred at room temperature then evaporated. Work-up up as described above gave a crude product which was purification with preparativ HPLC (Kromasil C8, 7 μm, 50×250 mm) using acetonitrile (70–100%) in ammonium acetate buffer (pH 7) as mobil phase gave 0.180 g (22% yield) of 3-[4-{2-(4-[Benzyloxycarbonylamino]phenyl) ethoxy}phenyl]-(S)-2-ethoxypropanoic acid ethyl ester.

$^1$H-NMR (600 MHz, CDCl$_3$): d 1.16 (t, 3H), 1.22 (t, 3H), 2.94 (d, 2H), 3.03 (t, 2H), 3.32–3.37 (m, 1H), 3.57–3.62 (m, 1H), 3.96 (t, 1H), 4.11 (t, 2H), 4.16 (q, 2H), 5.19 (s, 2H), 6.75 (bs, 1H), 6.8 (d, 2H), 7.13 (d, 2H), 7.21 (d, 2H), 7.3–7.41 (m, 7H). $^{13}$C-NMR (150 MHz; CDCl$_3$): d 15.3, 15.3, 35.4, 38.7, 61.0, 66,4, 67.2, 68.9, 80.7, 114.6, 119.1, 128.5, 128.6, 128.8, 129.0, 129.8, 130.7, 136.3, 153.9, 157.8, 172.8.

Example 53

3-[4-{2-(4-[Benzyloxycarbonylamino]phenyl) ethoxy}phenyl]-(S)-2-ethoxypropanoic Acid 3-[4-{2-(4-[Benzyloxycarbonylamino]phenyl) ethoxy}phenyl]-(S)-2-ethoxypropanoic acid ethyl ester (described in Example 52) (0.16 g; 0.32 mmole) was dissolved in tetrahydrofuran and lithium hydroxide (9 mg; 0.38 mmole) dissolved in water (1 ml) was added. The resulting mixture was stirred over night. Hydrochloric acid (1M; 1 ml) was added. Tetrahydrofuran was evaporated and the remaining water residue was extracted three times with ethyl acetate. The organic phase was dried with magnesium sulfate and evaporated to give 0.14 g (92.8% yield) of 3-[4-{2-(4-[benzyloxycarbonylamino]-phenyl) ethoxy}phenyl]-(S)-2-ethoxypropanoic acid.

$^1$H-NMR (600 MHz; CDCl$_3$): d 1.16 (s, 3H), 2.91–3.08 (m, 4H), 3.38–3.45 (m, 1H), 3.56–3.64 (m, 1H), 4.00–4.05 (m, 1H), 4.07–4.14 (m, 4H), 5.20 (s, 2H), 6.81 (d, 2H), 7.14 (d, 2H), 7.28–7.42 (m, 7H). $^{13}$C-NMR (150 MHz; CDCl$_3$): d 15.3, 35.4, 38.1, 67.0, 67.3, 68.9, 80.1, 114.7, 119.2, 128.5, 128.6, 128.8, 129.0, 129.8, 130.7, 136.3, 153.9, 157.9, 175.5.

Example 54

3-{4-[2-(4-tert-Butoxycarbonylaminophenyl) ethoxy]-3-methoxyphenyl}-2-ethoxypropanoic Acid (a) 3-(4-Benzyloxy-3-methoxyphenyl)-2-ethoxyacrylic Acid Ethyl Ester 4-Benzyloxy-3-methoxybenzaldehyde (7 g; 28.8 mmole) and (1,2-diethoxy-2-oxoethyl) (triphenyl)phosphonium chloride (13.6 g; 31 mmole) was dissolved in isopropanol and the reaction mixture was cooled to −10° C. Potassium carbonate (6 g; 43 mmole) was added. The resulting mixture was stirred over night and the temperature was allowed to reach room temperature. The reaction mixture was filtered and the filtrate was evaporated. Diethyl ether was added to the residue and the resulting mixture was stirred for a while and then insoluble material was filtered off. The filtrate was washed with potassium hydrogensulfate solution and water, dried with magnesium sulfate and evaporated. Isopropylether was added to the residue. Triphenylphosphine oxide precipitated and was filtered off and the filtrate was evaporated. Chromatography of the residue on silica gel using toluene with ethyl acetate (0, 1%, 3%) as eluant gave 5.2 g of 3-(4-benzyloxy-3-methoxyphenyl)-2-ethoxyacrylic acid ethyl ester. Since the product was not pure enough it was stirred with petroleum ether, insoluble material was filtered off and the filtrate was evaporated to give 4 g (38% yield) of pure 3-(4-benzyloxy-3-methoxyphenyl)-2-ethoxyacrylic acid ethyl ester.

$^1$H-NMR (300 MHz; CDCl$_3$): δ 1.33–1.5 (m, 6H), 3.92 (s, 3H), 4.03 (q, 2H), 4.3 (q, 2H), 5.16 (s, 2H), 6.88 (d, 1H), 6.96 (s, 1H), 7.2 (d, 1H), 7.27–7.5 (m, 6H).

(b) 3-(4-Benzyloxy-3-methoxyphenyl)-2-ethoxypropanoic Acid Ethyl Ester 3-(4-Benzyloxy-3-methoxyphenyl)-2-ethoxyacrylic acid ethyl ester (5.5 g, 15.4 mmole) was dissolved in ethyl acetate and hydrogenated using Pd/C (dry, 5%). The reaction mixture was filtered through celite. Evaporation of the filtrate gave 4 g (97% yield) of 3-(4-benzyloxy-3-methoxyphenyl)-2-ethoxypropanoic acid ethyl ester.

$^1$H-NMR (600 MHz; CDCl$_3$): δ 1.16 (t, 3H), 1.23 (t, 3H), 2.9 (m, 2H), 3.28–3.36 (m, 1H), 3.55–3.63 (m, 1H), 3.83 (s, 3H), 3.95 (m, 1H), 4.16 (m, 2H), 5.63 (bs, 1H), 6.72 (m, 1H), 6.76–6.85 (m, 2H). $^{13}$C-NMR (150 MHz; CDCl$_3$): δ 14.4, 15.3, 39.2, 56.0, 61.0, 66.4, 80.7, 112.4, 114.3, 122.2, 129.3, 144.6, 146.4, 172.8.

(c) 3-{4-[2-(4-tert-Butoxycarbonylaminophenyl)ethoxy]-3-methoxyphenyl}-2-ethoxypropanoic Acid Ethyl Ester 3-(4-Benzyloxy-3-methoxyphenyl)-2-ethoxypropanoic acid ethyl ester (0.5 g; 1.86 mmole) was dissolved in acetonitrile and potassium carbonate (0.53 g; 3.91 mmole) was added. 2-[4-(tert-Butoxycarbonylamino)phenyl]ethyl-4-methylbenzenesulfonate (described in Example 40a) (0.755 g, 1.92 mmole) was added. The resulting mixture was stirred and refluxed over night then filtered and the filtrate was evaporated. The residue was treated with sodium hydroxide (0.5 M) and diethyl ether. The phases were separated and the organic phase was dried with magnesium sulfate. Evaporation gave 0.7 g (77.2% yield) of 3-{4-[2-(4-tert-butoxycarbonylaminophenyl)ethoxy]-3-methoxyphenyl}-2-ethoxypropanoic acid ethyl ester.

$^1$H-NMR (300 MHz; CDCl$_3$): δ 1.18 (t, 3H), 1.27 (t, 3H), 1.52 (s, 9H), 2.95 (d, 2H), 3.1 (t, 2H), 3.3–3.43 (m, 1H), 3.58–3.7 (m, 1H), 3.87 (s, 3H), 3.98 (t, 1H), 4.13–4.25 (m, 4H), 6.48 (bs, 1H), 6.78–6.87 (m, 3H), 7.12 (d, 2H), 7.27–7.35 (m, 2H).

(d) 3-{4-[2-(4-tert-Butoxycarbonylaminophenyl)ethoxy]-3-methoxyphenyl}-2-ethoxypropanoic Acid 3-{4-[2-(4-tert-Butoxycarbonylaminophenyl)ethoxy]-3-methoxyphenyl}-2-ethoxypropanoic acid ethyl ester (0.7 g; 1.34 mmole) was dissolved in tetrahydrofuran and water (1:1), lithium hydroxide hydrate (0.09 g; 2.13 mmole) was added and the reaction mixture was stirred over night. Water was added and tetrahydrofuran evaporated. The remaining water residue was extracted once with diethyl ether, acidified with potassium hydrogensulfate and extracted with ethyl acetate. The organic phase was dried with magnesium sulfate. Evaporation gave 0.5 g (76% yield) of 3-{4-[2-(4-tert-butoxycarbonylaminophenyl)ethoxy]-3-methoxyphenyl}-2-ethoxypropanoic acid.

$^1$H-NMR (400 MHz; CD$_3$OD): δ 1.12 (t, 3H), 1.49 (s, 9H), 2.82–2.89 (m, 1H), 2.92–3.0 (m, 3H), 3.31–3.38 (m, 1H), 3.54–3.63 (m, 1H), 3.78 (s, 3H), 3.97–4.02 (m, 1H), 4.07–4.13 (m, 2H), 6.74 (m, 2H), 6.8 (m, 1H), 7.17 (d, 2H), 7.29 (d, 2H), 8.75 (bs, 1H). $^{13}$C-NMR (100 MHz; CD$_3$OD): δ 14.2, 27.6, 34.9, 38.5, 55.4, 65.9, 70.2, 79.5, 80.1, 113.9, 114.0, 118.8, 121.8, 129.1, 130.8, 132.9, 137.6, 147.3, 149.5, 154.3, 174.9.

Example 55

3-{3-[2-(4-tert-Butoxycarbonylaminophenyl)ethoxy] 4-methoxyphenyl}-2-ethoxypropanoic Acid 3-{3-[2-(4-tert-Butoxycarbonylaminophenyl)ethoxy]-4-methoxyphenyl}-2-ethoxypropanoic acid was synthesized from 3-benzyloxy-4-methoxybenzaldehyde according to the procedure described in Example 54.

¹H-NMR (400 MHz; CD₃OD): δ 1.1 (t, 3H), 1.5 (s, 9H), 2.8–2.88 (m, 1H), 2.91–3.02 (m, 3H), 3.32–3.37 (m, 1H), 3.53–3.61 (m, 1H), 3.76 (s, 3H), 3.95 (m, 1H), 4.1–4.15 (m, 2H), 6.77 (m, 1H), 6.81–6.85 (m, 2H), 7.19 (d, 2H), 7.3 (d, 2H), 8.75 (bs, 1H). ¹³C-NMR (100 MHz; CD₃OD): δ 14.2, 27.6, 34.9, 38.4, 55.5, 65.9, 70.1, 79.5, 80.0, 112.4, 115.4, 118.8, 122.0, 129.2, 130.4, 132.9, 137.6, 148.2, 148.6, 154.2, 174.8.

Example 56

(S)-2-Ethoxy-3[4-(2-[4-([{4-(tert-butyl)cyclohexyl}oxy]carbonylamino)phenyl]ethoxy)phenyl]propanoic Acid (a) 3-{4-[2-(4-Aminophenyl)ethoxy]phenyl}-(S)-2-ethoxypropanoic Acid Hydro Chloride Water (200 ml) was added to a solution of 3-{4-[2-(4-aminophenyl)ethoxy]phenyl}-(S)-2-ethoxypropanoic acid ethyl ester hydro chloride (described in Example 41b) (15 g; 42 mmole) in tetrahydrofuran (100 ml). Lithium hydroxide (3.4 g; 84 mmole) dissolved in a small amount of water was added while stirring and then the reaction mixture was stirred at room temperature over night. Tetrahydrofuran was evaporated and the remaining residue was extracted twice with ethyl acetate. The water phase was acidified with hydrochloric acid (2 M) and extracted with ethyl acetate. The organic phase was dried with magnesium sulfate. Evaporation gave 6.4 g of 3-{4-[2-(4-aminophenyl)ethoxy]phenyl}-(S)-2-ethoxypropanoic acid hydro chloride. The acidic water phase, from above, was neutralized with sodium hydroxide to pH5 and extracted with dichloromethane. The organic phase was dried with magnesium sulfate and evaporated. This procedure gave 1.4 g more of the desired product. The total yield of 3-{4-[2-(4-aminophenyl)ethoxy]phenyl}-(S)-2-ethoxypropanoic acid hydro chloride was 7.8 g (50.8%).

¹H-NMR (500 MHz, CD₃OD): δ 1.12 (t, J=7 Hz, 3H), 2.85 (dd, J=14, 8 Hz, 1H), 2.94 (t, J=7 Hz, 2H), 2.97 (dd, J=14, 4.5 Hz, 1H), 3.31–3.37 (m, 1H), 3.56–3.62 (m, 1H), 3.98 (dd, J=8, 4.5 Hz, 1H), 4.08 (t, J=7 Hz, 2H), 6.77 (d, J=8.6 Hz, 2H), 6.80 (d, J=8.8 Hz, 2H), 7.09 (d, J=8.6 Hz, 2H) and 7.14 (d, J=8.8 Hz, 2H). ¹³C-NMR (125 MHz, CD₃OD): δ 15.31, 36.05, 39.37, 67.09, 70.20, 81.49, 115.34 (2C), 117.74(2C), 130.76(2C), 130.81, 130.94, 131.41(2C), 144.82, 159.10, 176.35.

(b) (S)-2-Ethoxy-3[4-(2-[4-([{4-(tert-butyl)cyclohexyl}oxy]carbonylamino)phenyl]ethoxy)phenyl]propanoic Acid 3-{4-[2-(4-Aminophenyl)ethoxy]phenyl}-(S)-2-ethoxypropanoic acid hydro chloride (0.2 g, 0.547 mmole) and sodium hydrogen carbonate (0.05 g, 0.595 mmole) were mixed in tetrahydrofurane (5 ml), stirred at room temperature for 20 minutes and then 4-tert-butylcyclohexyl chloroformate (0.131 g, 0.599 mmole) was added. The reaction mixture was stirred at room temperature overnight and then a little more 4-tert-butylcyclohexyl chloroformate was added since the reaction was not complete according to HPLC. The reaction mixture was stirred for 2 more hours and then evaporated to dryness. Ethyl acetate and water were added to the residue and the phases were separated. The organic phase was dried with magnesium sulfate and the solvent was evaporated. Chromatography on silica gel (Isolute, SI ) using dichloromethane:heptane (1:1), followed by dichloromethane, and then methanol: dichloromethane (1:99) as eluants gave 0.28 g (93% yield) (S)-2-ethoxy-3[4-(2-[4-([{4-(tert-butyl)cyclohexyl}oxy]carbonylamino)phenyl]ethoxy)phenyl]propanoic acid.

¹H-NMR (400 MHz, CD₃OD): δ 0.86 (s, 9H), 0.99–1.18 (m, 3H), 1.0 (t, J=7 Hz, 3H), 1.35 (dd, br, J=24, 12 Hz, 2H), 1.83 (d, br, J=12 Hz, 2H), 2.08 (d, br, J=12 Hz, 2H), 2.83 (dd, J=14.5, 8 Hz, 1H), 2.92–2.98 (m, 3H), 3.29–3.36 (m, 1H), 3.53–3.61 (m, 1H), 3.97 (dd, J=8, 4.5 Hz, 1H, 4.08 (t, J=7 Hz, 2H), 4.48–4.56(m, 1H), 6.79 (d, J=8.5 Hz), 7.12 (d, J=8.5 Hz, 2H), 7.17 (d, J=8.5 Hz, 2H) and 7.32 (d, J=8.5 Hz). ¹³C-NMR (100 MHz, CD₃OD): δ 15.30, 26.63(2C), 28.04(3C), 33.07, 33.60(2C), 36.10, 39.32, 67.13, 69.90, 75.41, 81.30, 115.37(4C), 120.02, 130.34(2C), 130.73, 131.42(2C), 134.40, 138.57, 155.80, 159.06, 176.05.

Example 57

(S)-2-Ethoxy-3-(4-{2-[4-(phenoxycarbonylamino)phenyl]ethoxy}-phenyl)propanoic Acid Ethyl Ester 3-{4-[2-(4-Aminophenyl)ethoxy]phenyl}-(S)-2-ethoxypropanoic acid ethyl ester hydro chloride (described in Example 41b) (0.55 g; 1.4 mmole) was dissolved in tetrahydrofuran (5 ml). Phenyl chloroformat (0.675 g; 3 mmole) was added slowly. The reaction mixture was stirred at room temperature and continuosly checked with HPLC and after 3 days was all the starting material consumed. Water was added, tetrahydrofuran evaporated and the residue extracted three times with ethyl acetate. The organic phase was dried with magnesium sulfate and evaporated. Purification of the crude product with preparative HPLC (Kromasil C8, 7 μm, 50×250 mm) using acetronitrile (70%) in ammonium acetate buffer (pH 7) as mobil phase gave 0.46 g (96.3% yield) (S)-2-ethoxy-3-(4-{2-[4-(phenoxycarbonylamino)phenyl]ethoxy]phenyl)propanoic acid ethyl ester.

¹H-NMR (300 MHz; CDCl₃): δ 1.18 (t, 3H), 1.24 (s, 9H), 2.96 (d, 2H), 3.07 (t, 2H), 3.31–3.41 (m, 1H), 3.55–3.68 (m, 1H), 3.98 (t, 2H), 4.10–4.23 (m, 4H), 6.83 (d, 2H), 6.96 (bs, NH), 7.12–7.31 (m, 9H), 7.37–7.45 (m, 4H), ¹³C-NMR (75 MHz; CDCl₃): δ 15.5, 28.6, 35.4, 36.1, 66.8, 69.0, 80.7, 85.4, 114.7, 119.0, 128.9, 129.7, 130.6, 133.1, 137.0, 153.1, 157.9, 204.0.

Example 58

3-[4-(2-{4-tert-Butoxycarbonylaminophenyl}ethoxy)phenyl]-2-(2-methoxyethoxy)propanoic Acid Methyl Ester (a) Benzyl 2-(2-Methoxyethoxy)acetate 2-(2-Methoxyethoxy)acetic acid (10 g; 75 mmole) and tetrabutylammonium bromide (25.3 g; 75 mmole) were dissolved in sodium hydroxide solution (2 M; 75 ml; 75 mmole). Benzyl bromide (15.3 g; 89 mmole) dissolved in dichloromethane (150 ml) was added. The reaction mixture was refluxed 4 hours. After separation the organic phase was dried with magnesium sulfate and evaporated. Chromatography using dichloromethane as eluant gave 17.5 g (94%) of benzyl 2-(2-methoxyethoxy)acetate.

¹H-NMR (500 MHz; CD₃OD): d 3.41 (s, 3H), 3.62 (t, 2H), 3.77 (t, 2H), 4.24 (s, 2H), 5.23 (s, 2H), 7.31–7.45 (m, 5H).

(b) (Z)-3-[4-(Benzyloxy)phenyl]-2-(2-methoxyethoxy)-2-propenoic Acid Benzyl Ester 4-(Benzyloxy)benzaldehyde (3.00 g; 14.0 mmole) and benzyl 2-(2-methoxyethoxy)acetate (4.23 g; 17.0 mmole) were dissolved in dry tetrahydrofuran (100 ml) and cooled to −20° C. Potassium tert-butoxide (1.91 g; 17.0 mmole) dissolved in dry tetrahydrofuran (10 ml) was slowly added and the reaction was stirred over night at −20° C. The reaction was quenched with acetic acid (0.85 g; 14.0 mmole). The crued product was isolated, redissolved in toluene and refluxed over night with p-toluenesulfonic acid (0.24 g; 1.4 mmole) in a Dean-Stark apparatus to separate the water. The solution was cooled, washed with sodium hydrogene carbonate, dried with magnesium sulfate and evaporated. Purification of the crude product with preparativ HPLC (Kromasil C8, 10 μm, 50×500 mm) using acetronitrile (50–70%) in ammonium acetate buffer (pH 7) as mobil phase gave 1.83 g (29% yield) of (Z)-3-[4-(benzyloxy) phenyl]-2-(2-methoxyethoxy)-2-propenoic acid benzyl ester.

$^1$H-NMR (500 MHz; CD$_3$OD): δ 3.36 (s, 3H), 3.65–3.72 (m, 2H), 4.09–4.17 (m, 2H), 5.11 (s, 2H), 5.30 (s, 2H), 6.98 (d, 2H), 7.05 (s, 1H), 7.32–7.50 (m, 10H), 7.81 (d, 2H).

(c) 3-(4-Hydroxyphenyl)-2-(2-methoxyethoxy)propanoic Acid (Z)-3-[4-(Benzyloxy)phenyl]-2-(2-methoxyethoxy)-2-propenoic acid benzyl ester (1.75 g; 4.2 mmole) was hydrogenated in methanol (50 ml) at atmospheric pressure using Pd/C (5%) as catalyst. The mixture was filtered through celite and evaporated in vacuo to give 3-(4-hydroxyphenyl)-2-(2-methoxyethoxy)propanoic acid 0.83 g (88% yield).

$^1$H-NMR (500 MHz; CD$_3$OD): δ 2.90–2.97 (m, 1H), 3.10–3.16 (m, 1H), 3.42 (s, 3H), 3.49–3.52 (m, 1H), 3.55–3.63 (m, 2H), 3.65–3.72 (m, 1H), 4.12 (q, 1H), 6.74 (d, 2H), 7.10 (d, 2H).

(d) 3-(4-Hydroxyphenyl)-2-(2-methoxyethoxy)propanoic Acid Methyl Ester 3-(4-Hydroxyphenyl)-2-(2-methoxyethoxy)propanoic acid (0.80 g, 3.1 mmole) was dissolved in hydrochloric acid saturated methanol and refluxed for two hours. The mixture was evaporated in vacuo to give 3-(4-hydroxyphenyl)-2-methoxyethoxy)propanoic acid methyl ester 0.84 g (99% yield).

$^1$H-NMR (500 MHz; CD$_3$OD): δ 2.97–3.02 (m, 2H), 3.34 (s, 3H), 3.50–3.57 (m, 4H), 3.73 (s, 3H), 4.08–4.17 (m, 1H), 6.75 (d, 2H), 7.11 (d, 2H).

(e) 3-[4-(2-{4-tert-Butoxycarbonylaminophenyl}ethoxy) phenyl]-2-(2-methoxyethoxy)propanoic Acid Methyl Ester 2-[4-{tert-Butoxycarbonyl(methyl)amino}phenyl]ethyl-4-methylbenzenesulfonate (described in Example 40a) (0.50 g; 1.26 mmole), 3-(4-hydroxyphenyl)-2-(2-methoxyethoxy) propanoic acid methyl ester(0.32 g; 1.26 mmole) and potassium carbonate (0.35 g; 2.64 mmole) were mixed in acetonitrile (20 ml) and refluxed over night. Water was added, acetonitrile evaporated and the residue extracted three times with ethyl acetate. The organic phase was dried with magnesium sulfate and evaporated. Purification of the crude product with preparativ HPLC (Kromasil C8, 7 μm, 50×250 mm) using acetronitrile (50–70%) in ammonium acetate buffer (pH 7) as mobil phase gave 0.34 g (58% yield) of 3-[4-(2-(4-tert-butoxycarbonylaminophenyl}ethoxy) phenyl]-2-(2-methoxyethoxy)propanoic acid methyl ester $^1$H-NMR (500 MHz; CDCl$_3$): d 1.54 (s, 9H), 2.97–3.02 (m, 2H), 3.05 (t, 2H), 3.33 (s, 3H), 3.48–3.55 (m, 4H), 3.72 (s, 3H), 4.09–4.17 (m, 3H), 6.64 (bs, NH), 6.82 (d, 2H), 7.15 (d, 2H), 7.21 (d, 2H), 7.32 (d, 2H). $^{13}$C-NMR (125 MHz; CDCl$_3$): d 14.5, 15.5, 28.6, 35.4, 38.7, 52.1, 59.2, 69.0, 70.3, 72.2, 81.3, 114.6, 119.1, 129.4, 129.7, 130.6, 133.1, 137.1, 153.2, 157.9, 173.0.

Example 59

3-[4-(2-{4-tert-Butoxycarbonylaminophenyl}ethoxy)phenyl]-2-(2-methoxyethoxy)propanoic Acid 3-[4-(2-{4-tert-Butoxycarbonylaminophenyl}ethoxy) phenyl]-2-(2-methoxyethoxy)propanoic acid methyl ester (described in Example 58) (0.26 g; 0.55 mmole) was dissolved in tetrahydrofuran:water (1:3, 4 ml). Lithium hydroxide (16.0 mg; 0.66 mmole) dissolved in a small amount of water was added. The reaction mixture was stirred two hours at room temperature and then evaporated. The residue was redissolved in diethyl ether and hydrochloric acid (2M) and extracted. The organic phase was dried with magnesium sulfate and evaporated to give 0.235 g (92% yield) of 3-[4-(2-{4-tert-butoxycarbonylaminophenyl}ethoxy) phenyl]-2-(2-methoxyethoxy)propanoic acid.

H-NMR (500 MHz; CDCl$_3$): d 1.46 (s, 9H), 2.83–3.02 (m, 3H), 3.27 (s, 3H), 3.38–3.65 (m, 3H), 3.99 (q, 1H), 4.03–4.10 (m, 2H), 6.75 (d, 2H), 7.08–7.16 (m, 4H), 7.26 (bd, 2H). $^{13}$C-NMR (125 MHz; CDCl3): d 28.5, 35.2, 38.4, 58.9, 69.0, 70.2, 71.9, 81.1, 114.6, 119.1, 129.6, 130.6, 133.0, 137.1, 153.2, 157.7, 174.6.

Example 60

3-[4-(2-{4-tert-Butoxycarbonylaminophenyl}ethoxy)phenyl]-2-(2,2,2-trifluoroethoxy)propanoic Acid Methyl Ester 3-[4-(2-{4-tert-Butoxycarbonylaminophenyl}ethoxy) phenyl]-2-(2,2,2-trifluoroethoxy)propanoic acid methyl ester was synthesized using the same method as in Example 62 (a) from 3-(4-hydroxyphenyl)-2-(2,2,2-trifluoroethoxy) propanoic acid methyl ester and 4-(2-hydroxyethyl) phenylcarbamic acid tert-butyl ester(described in Example 38b.

$^1$H-NMR (300 MHz; CD$_3$OD): d 1.54 (s, 9H), 2.95–3.12 (m, 4H), 3.63–3.74 (m, 1H), 3.75 (s, 3H), 3.95–4.04 (m, 1H), 4.12 (t, 3H), 4.16–4.22 (m, 1H), 6.59 (bs, NH), 6.83 (d, 2H), 7.14 (d, 2H), 7.21 (d, 2H), 7.32 (t, 2H). $^{13}$C-NMR (75 MHz; CD$_3$OD): d 28.7, 35.42, 38.5, 52.4, 67.9, 68.4, 69.0, 81.7, 114.7, 119.0, 121.9, 125.6, 128.4, 129.7, 130.6, 133.1, 137.0, 153.1, 158.0, 171.5.

Example 61

3-[4-(2-{4-tert-Butoxycarbonylaminophenyl}ethoxy)phenyl]-2-(2,2,2-trifluoroethoxy)propanoic Acid 3-[4-(2-{4-tert-Butoxycarbonylaminophenyl}ethoxy) phenyl]-2-(2,2,2-tnifluoroethoxy)propanoic acid methyl ester (described in Example 60)(0.27 g; 0.52 mmole) was dissolved in tetrahydrofuran and water (2:1), lithium hydroxide (0.015 g; 0.62 mmole) was added and the reaction mixture was stirred over night. Water was added and tetrahydrofuran was evaporated. The remaining water residue was extracted once with diethyl ether, acidified with diluted hydrochloric acid and extracted with ethyl acetate. The organic phase was dried with magnesium sulfate. Evaporation gave 0.22 g (85% yield) of 3-[4-(2-{4-tert-butoxycarbonylaminophenyl}ethoxy)phenyl]-2-(2,2,2-trifluoroethoxy)propanoic acid.

$^1$H-NMR (500 MHz; CD$_3$OD): d 1.47 (s, 3H), 3.01–3.08 (m, 3H), 3.12–3.17 (m, 1H), 3.68–3.78 (m, 1H), 3.98–4.07 (m, 1H), 4.23 (q, 1H), 6.84 (d, 2H), 7.18 (d, 2H), 7.22 (d, 2H), 7.31 (m, 2H). $^{13}$C-NMR (125 MHz; CD$_3$OD): d 28.7, 35.42, 38.5, 67.9, 68.4, 69.0, 81.7, 114.7, 119.0, 121.9, 125.6, 128.4, 129.7, 130.6, 133.1, 137.0, 153.1, 158.0, 171.5.

Example 62

2-Ethoxy-3-{4-[2-(4-methanesulfonylaminophenyl) ethoxy]phenyl}propanoic Acid Ethyl Ester (a) 3-{4-[2-(4-Aminophenyl)ethoxy]phenyl}-2-ethoxypropanoic Acid Ethyl Ester 4-Aminophenethyl alcohol (1.39 g; 10.2 mmole) and 2-ethoxy-3-(4-hydroxyphenyl)propanoic acid ethyl ester (described in Example 20b) (2.42 g; 10.2 mmole) were dissolved in dichloromethane (35 ml) under argon at room temperature. Azodicarbonyl dipiperidine (3.85 g; 15.2 mmole) and thereafter triphenylphosphine (3.20 g; 12.2 mmole) were added. After stirring at room temperature for 1 minute dichloromethane (30 ml) was added and after 21 hours the solvent was evaporated in vacuo. Purification by chromatography on silica gel using heptane:ethyl acetate (3:2) as eluant gave 3.12 g (yield 86%) of 3-{4-[2-(4-aminophenyl)ethoxy]phenyl}-2-ethoxypropanoic acid ethyl ester.

$^1$H-NMR (400 MHz; CDCl$_3$): δ 1.18 (t, 3H, J=7 Hz), 1.24 (t, 3H, J=7 Hz), 2.95–3.02 (m, 4H), 3.31–3.42 (m, 1H), 3.58–3.67 (m, 3H), 3.96–4.02 (m, 1H), 4.10 (t, 2H, J=7 Hz), 4.13 (q, 2H, J=7 Hz), 6.66 (dm, 2H, J=8.3 Hz, unresolved), 6.83 (dm, 2H, J=8.3 Hz, unresolved), 7.08 (dm, 2H, J=8.3 Hz, unresolved), 7.16 (dm, 2H, J=8.3 Hz, unresolved). $^{13}$C-NMR (100 MHz; CDCl$_3$): δ 14.1, 15.0, 34.9, 38.4, 60.7, 66.1, 69.0, 80.3, 114.3, 115.2, 127.9, 129.1, 129.7, 130.3, 144.8, 157.6, 172.5.

(b) 2-Ethoxy-3-{4-[2-(4-methanesulfonylaminophenyl)ethoxy]phenyl}propanoic Acid Ethyl Ester Triethylamine (0.544 g; 2.99 mmole) and thereafter methanesulfonyl chloride (0.392 g; 2.99 mmole) were added to a solution of 3-{4-[2-(4-aminophenyl)ethoxy]phenyl}-2-ethoxypropanoic acid ethyl ester (0.89 g; 2.49 mmole) in dichloromethane (8.9 ml) at 0° C. After stirring at room temperature for 20 hours the reaction mixture was poured onto a mixture of hydrochloric acid and ice. Dichloromethane was added, the phases were separated and the organic phase was washed with water, dried (sodium sulfate), filtered and the solvent was evaporated in vacuo. Purification by chromatography on silica gel using heptane:ethyl acetate (3:2) as eluant gave 0.78 g (yield 72%) of 2-ethoxy-3-{4-[2-(4-methanesulfonylaminophenyl)ethoxy]phenyl}propanoic acid ethyl ester.

$^1$H-NMR (500 MHz; CDCl$_3$): δ 1.18 (t, 3H, J=7 Hz), 1.25 (t, 3H, J=7 Hz), 2.96–2.99 (m, 2H), 3.01 (s, 3H), 3.07 (t, 2H, J=7 Hz), 3.34–3.43 (m, 1H), 3.59–3.66 (m, 1H), 3.98–4.03 (m, 1H), 4.13–4.22 (m, 4H), 6.83 (dm, 2H, J=8.8 Hz, unresolved), 7.16 (dm, 2H, J=8.8 Hz, unresolved), 7.22 (dm, 2H, J=8.5 Hz, unresolved), 7.28 (dm, 2H, J=8.5 Hz, unresolved). $^{13}$C-NMR (125 MHz; CDCl$_3$): δ 14.1, 15.0, 35.0, 38.3, 39.0, 60.7, 66.1, 68.3, 80.2, 114.2, 121.2, 129.3, 130.1, 130.3, 135.1, 135.7, 157.4, 172.5.

Example 63

2-Ethoxy-3-{4-[2-(4-methanesulfonylaminophenyl)ethoxy]phenyl}propanoic Acid

2-Ethoxy-3-{4-[2-(4-methanesulfonylaminophenyl)ethoxy]phenyl}propanoic acid ethyl ester (described in Example 62) (0.554 g; 1.27 mmole) was dissolved in tetrahydrofuran (5.7 ml). Lithium hydroxide hydrate (0.137 g; 3,26 mmole) was dissolved in water and added in portions during 30 minutes at room temperature. The reaction mixture was kept in the refrigerator over night. Tetrahydrofuran was evaporated in vacuo. The water residue was washed with ethyl acetate, acidified with hydrochloric acid (1M) to pH 1–2 and the mixture was extracted with ethyl acetate. The organic phase was washed with brine, dried (sodium sulfate), filtered and the solvent was evaporated in vacuo to give 0.54 g (yield 100%) of 2-ethoxy-3-{4-[2-(4-methanesulfonylaminophenyl)ethoxy]phenyl}propanoic acid.

$^1$H-NMR (400 MHz; CDCl$_3$): δ 1.17 (t, 3H, J=7 Hz), 2.93–3.0 (m, 4H), 3.0–3.09 (m, 3H), 3.37–3.47 (m, 1H), 3.59–3.68 (m, 1H), 4.03–4.08 (m, 1H), 4.12 (t, 2H, J=7 Hz), 6.82 (dm, 2H, J=8.8 Hz, unresolved), 7.14–7.29 (m, 6H), 7.40 (s, 1NH), 9.02 (bs, 1H). $^{13}$C-NMR (100 MHz; CDCl$_3$): δ 14.9, 35.0, 37.8, 39.0, 66.5, 68.3, 79.6, 114.3, 121.2, 128.8, 130.0, 130.3, 135.1, 135.6, 157.4, 176.3.

Example 64

(S)-2-Ethoxy-3-[4-{2-(4-[methylsulfonyl(methyl)amino]phenyl)ethoxy}-phenyl]propanoic Acid Ethyl Ester (a) (S)-2-Ethoxy-3-[4-{2-(4-[methylsulfonylamino]phenyl)ethoxy}phenyl]propanoic Acid Ethyl Ester 3-{4-[2-(4-Aminophenyl)ethoxy]phenyl}-(S)-2-ethoxypropanoic acid ethyl ester hydro chloride (described in Example 41b) (0.45 g; 1.26 mmole), dichloromethane (10 ml), methanesulfonyl chloride (0.216 g; 1.88 mmole) and triethylamine (0.318 g; 3.14 mmole) were mixed at 0° C. and stirred for 3 hours at that temperature and then at room temperature over night. The reaction mixture was poured into ethyl acetate (50 ml). Triethylamine hydrochloride salt was filtered off and the filtrate evaporated. The residue was redissolved and extracted with ethyl acetate and water. The organic phase was washed once more with water, dried with sodium sulfate and evaporated. Chromatography with diethyl ether:petroleum ether (1:3, 1:1, 3:1) as eluant gave 0.18 g (32.8% yield) of (S)-2-ethoxy-3-[4-{2-(4-[methylsulfonylamino]phenyl)ethoxy}phenyl]propanoic acid ethyl ester.

$^1$H-NMR (500 MHz; CDCl$_3$): δ 1.21 (t, 3H), 1.28 (t, 3H), 2.99 (m, 2H), 3.04 (s, 3H), 3.11 (m, 2H), 3.39 (m, 1H), 3.64 (m, 1H), 4.01 (m, 1H), 4.15–4.25 (m, 4H), 6.84 (d, 2H), 7.17–7.23 (m, 4H), 7.30–7.35 (m, 2H).

(b) (S)-2-Ethoxy-3-[4-{2-(4-[methylsulfonyl(methyl)amino]phenyl)ethoxy}phenyl]-propanoic Acid Ethyl Ester (S)-2-Ethoxy-3-[4-{2-(4-[methylsulfonylamino]phenyl)ethoxy}phenyl]propanoic acid ethyl ester (0.17 g; 0.39 mmole) was dissolved in tetrahydrofuran (10 ml). Iodomethane (0.277 g; 1.95 mmole) and sodium hydride (0.019 g; 0.79 mmole) were added and the reaction mixture was stirred at room temperature for 3 hours and then evaporated. The residue was redissolved and extracted with diethyl ether and water. The organic phase was washed once more with water, dried with sodium sulfate and evaporated. Chromatography with ethyl acetate:petroleum ether (1:1) gave 0.098 g (55.8% yield) of (S)-2-ethoxy-3-[4-{2-(4-[methylsulfonyl(methyl)amino]phenyl)ethoxy}phenyl]propanoic acid ethyl ester.

$^1$H-NMR (300 MHz; CDCl$_3$): δ 1.16 (t, 3H), 1.23 (t, 3H), 2.84 (s, 3H), 2.94 (m, 2H), 3.08 (m, 2H), 3.31 (s, 3H), 3.36 (m, 1H), 3.60 (m, 1H), 3.96 (m, 1H), 4.10–4.20 (m, 4H), 6.80 (d, 2H), 7.14 (d, 2H), 7.31 (m, 4H). $^{13}$C-NMR (75.4 MHz; CDCl$_3$): δ 14.1, 15.1, 35.0–35.5 (2C), 38.0–38.7 (2C), 60.7, 66.1, 68.2, 80.3, 114.2, 126.2, 129.3, 129.8, 130.3, 137.8, 139.6, 157.3, 172.3.

Example 65

3-(4-{2-[4-(2,4,5-Trichlorobenzenesulfonylamino)phenyl]ethoxy}phenyl)-(S)-2-ethoxypropanoic Acid 3-{4-[2-(4-Aminophenyl)ethoxy]phenyl}-(S)-2-ethoxypropanoic acid hydro chloride (described in Example 56a) (0.2 g; 0.547 mmole) and sodium hydrogen carbonate (0.05 g; 0.6 mmole) were mixed in acetonitrile (10 ml) and stirred at room temperature for 15 minutes. The mixture was then cooled in an ice-bath and 2,4,5-trichlorobenzenesulfonyl chloride (0.184 g; 0.657 mmole)

was added. After addition, the ice-bath was removed and the reaction mixture was heated to reflux for 4 hours and then evaporated to dryness. Ethyl acetate and water were added to the residue and the phases were separated. The organic phase was dried with magnesium sulfate and the solvent was evaporated. Chromatography on silica gel (Isolute, SI) using dichloromethane and then methanol (2%) in dichloromethane as eluant gave 0.28 g (89% yield) of 3-(4-{2-[4-(2,4,5-trichlorobenzenesulfonylamino)phenyl]ethoxy}phenyl]-(S)-2-ethoxypropanoic acid.

$^1$H-NMR (500 MHz, CDCl$_3$): δ 1.21 (t, J=7 Hz, 3H), 2.98 (dd, J=14.5, 7.5 Hz, 1H), 3.03 (t, J=6.5 Hz, 2H), 3.09 (dd, J=14.5, 4.5 Hz, 1H), 3.44–3.50 (m, 1H), 3.61–3.67 (m, 1H), 4.08 (dd, J=7.5, 4.5 Hz, 1H), 4.12 (t, J=7 Hz, 2H), 6.81 (d, J=8 Hz, 2H), 7.10 (d, J=8 Hz, 2H), 7.17 (d, J=8 Hz, 2H), 7.21 (d, J=8 Hz, 2H), 7.29 (s, 1H), 7.63 (s, 1H) and 8.10 (s, 1H). $^{13}$C-NMR (125 MHz, CDCl$_3$): δ 15.0, 35.0, 37.7, 66.8, 68.1, 79.7, 114.4(2C), 122.1(2C), 128.8, 129.9, 130.1(2C), 130.5 (2C), 132.1, 132.8, 133.0, 133.3, 135.9, 136.7, 138.2, 157.5, 175.

Example 66

3-[4-{2-(4-Benzylsulfonylaminophenyl)ethoxy}phenyl]-2-(S)-ethoxypropanoic Acid Ethyl Ester 3-{4-[2-(4-Aminophenyl)ethoxy]phenyl}-(S)-2-ethoxypropanoic acid ethyl ester hydro chloride (described in Example 41b) (0.5 g; 1.27 mmole) was dissolved in dichloromethane (10 ml) and triethylamine (0.39 ml; 2.8 mmole) was added. The mixture was cooled to 0° C., Phenylmethanesulphonyl chloride (0.32 g; 1.68 mmole) was added. The reaction mixture was then stirred overnight and the temperature was allowed to reach room temperature. Water was added and the phases were separated. The organic phase was washed with water, dried with magnesium sulfate and evaporated. Chromatography of the residue on silica gel using ethyl acetate/heptane as eluant gave 0.245 g (38% yield) of 3-[4-{2-(4-benzylsulfonylaminophenyl)ethoxy}phenyl]-2-(S)-ethoxypropanoic acid ethyl ester.

$^1$H-NMR (600 MHz, CDCl$_3$): δ 1.15 (t, J=7 Hz, 3H), 1.15 (t, J=7 Hz, 3H), 2.91–2.97 (m, 2H), 3.06 (t, J=7 Hz, 2H), 3.32–3.37 (m, 1H), 3.57–3.62 (m, 1H), 3.96 (dd, J=8, 6 Hz, 1H), 4.13–4.17 (m, 4H), 4.29 (s, 2H), 6.82 (d, 8.4 Hz, 2H), 7.10 (d, J=8.4 Hz, 2H), 7.15 (d, J=9 Hz, 2H), 7.24–7.26 (m, 4H) and 7.30–7.32 (m, 3H). $^{13}$C-NMR (150 MHz, CDCl$_3$): δ 14.15, 14.99, 35.03, 35.37, 57.31, 60.74, 66.10, 68.36, 80.27, 114.25(2C), 120.31(2C), 128.51, 128.74(2C), 128.80, 129.35, 130.04(2C), 130.35(2C), 130.78(2C), 135.12, 135.22, 157.43, 172.50.

Example 67

3-[4-{2-(4-Benzylsulfonylaminophenyl)ethoxy}phenyl]-2-(S)-ethoxypropanoic Acid

3-[4-{2-(4-Benzylsulfonylaminophenyl)ethoxy}phenyl]-2-(S)-ethoxypropanoic acid ethyl ester (described in Example 66) (0.15 g; 0.29 mmole) was dissolved in tetrahydrofuran(2 ml). Lithium hydroxide (0.0084 g; 0.35 mmole) in water (2 ml) was added. The reaction mixture was stirred at room temperature. After 6 hours, the reaction was checked by TLC (silica gel, ethyl acetate:heptane=50:50) and it was not complete. More. lithium hydroxide (approx. 0.01 g), was added the reaction mixture was stirred overnight and tetrahydrofuran was evaporated. The remaining solution was extracted with diethyl ether. The water phase was acidified with hydrochloric acid (1%) to pH~2 and extracted twice with ethyl acetate. The organic phases were combined, dried with magnesium sulfate and the solvent was evaporated. Chromatography of the residue on silica gel (Isolute, SI) using dichloromethane and then dichloromethane:methanol (98:2) as eluant gave 0.125 g (88% yield) of 3-[4-{2-(4-benzylsulfonylaminophenyl)ethoxy}phenyl]-2-(S)-ethoxypropanoic acid.

$^1$H-NMR (500 MHz, CDCl$_3$): δ 1.20 (t, J=7 Hz, 3H), 2.97 (dd, J=14, 8 Hz, 1H), 3.07 (dd, J=14, 4.5 Hz, 1H), 3.09 (t, J=7 Hz, 2H), 3.41–3.47 (m, 1H), 3.60–3.66 (m, 1H), 4.05 (dd, J=8, 4.5 Hz, 1H), 4.18 (t, J=7 Hz, 2H), 4.33 (s, 2H), 6.86 (d, J=8.5 Hz, 2H), 6.96 (s, 1H), 7.14 (d, J=8.5 Hz, 2H), 7.27–7.30 (m, 4H) and 7.35–7.37 (m, 3H). $^{13}$C-NMR (125 MHz, CDCl$_3$): δ 14.97, 35.04, 37.83, 57.32, 66.65, 68.36, 79.66, 114.36(2C), 120.31(2C), 128.45, 128.76(2C), 128.83 (2C), 130.07(2C), 130.44(2C), 130.81(2C), 135.10, 135.21, 157.57, 175.78.

Example 68

2-Ethoxy-3-{4-[2-(4-isobutyrylaminophenyl)ethoxy]phenyl}propanoic Acid Ethyl Ester (a) N-[4-(2-Hydroxyethyl)phenyl]isobutyramide 2-Methylpropanoic acid anhydride (24.15 g; 153 mmole) was slowly added to a warm solution of 4-aminophenethyl alcohol (21 g; 153 mmole) in acetone (200 ml). The reaction mixture was refluxed for 1 hour and then more 2-methylpropanoic acid anhydride (1 g) was added. The reflux was continued for 1.5 hours and then the solvent was evaporated in vacuo. Recrystallization of the solid residue in dichloromethane:heptane gave 30.7 g (yield 97%) N-[4-(2-hydroxyethyl)phenyl]isobutyramide as white crystals.

$^1$H-NMR (400 MHz; Acetone-d$_6$): δ 1.20 (d, 6H, J=6.7 Hz), 2.54–2.64 (m, 1H), 2.80 (t, 2H, J=7 Hz), 3.40 (t, 1OH, J=5.6 Hz), 3.75–3.80 (m, 2H), 7.13 (dm, 2H, J=8.5 Hz, unresolved), 7.53 (dm, 2H, J=8.5 Hz, unresolved), 8.77 (s br, 1NH).

(b) 2-Ethoxy-3-{4-[2-(4-isobutyrylaminophenyl)ethoxy]phenyl}propanoic Acid Ethyl Ester 2-Ethoxy-3-(4-hydroxyphenyl)propanoic acid ethyl ester (described in Example 20b) (0.71 g; 2.97 mmole) dissolved in dichloromethane (5 ml) was added to a mixture of N-[4-(2-hydroxyethyl)phenyl]isobutyramide (0.5 g; 2.47 mmole), azodicarbonyl dipiperidine (0.75 g; 2.97 mmole) and triphenylphosphine (0.78 g; 2.97 mmole) in dichloromethane (15 ml). After stirring at room temperature over night the reaction mixture was filtered and the solvent was evaporated in vacuo. The residue was purified by chromatography on silica gel using heptane:ethyl acetate (gradient 3:1 to 1:1) as eluant to give 0.69 g (yield 65%) of 2-ethoxy-3-{4-[2-(4-isobutyrylaminophenyl)ethoxy]phenyl}propanoic acid ethyl ester.

$^1$H NMR (500 MHz; CDCl$_3$): δ 7.47 (d, J=8.2 Hz, 2H), 7.22 (d, J=8.2 Hz, 2H), 7.13 (d, J=8.6 Hz, 2H), 6.80 (d, J=8.6 Hz, 2H), 4.16 (q, J=7.1 Hz, 2H), 4.11 (t, J=7.1 Hz, 2H), 3.96 (dd, J=7.4 and 6.0 Hz, 1H), 3.59 (m, 1H), 3.34 (m, 1H), 3.04 (t, J=7.1 Hz, 2H), 2.94 (m, 2H), 2.50 (sept, J=6.9 Hz, 1H), 1.25 (d, J=6.9 Hz, 6H), 1.22 (t, J=7.1 Hz, 3H), 1.16 (t, J=7.0 Hz, 3H).

Example 69

2-Ethoxy-3-[4-(2-{4-isobutyrylaminophenyl}ethoxy)phenyl]propanoic Acid

2-Ethoxy-3-{4-[2-(4-isobutyrylaminophenyl)ethoxy]phenyl}propanoic acid ethyl ester (described in Example 68)

was hydrolyzed using the same method as in Example 2 to give 2-ethoxy-3-[4-(2-{4-isobutyrylaminophenyl}ethoxy) phenyl]propanoic acid.

¹H NMR (300 MHz; CDCl₃): δ 7.46 (d, 8.3 Hz, 2H), 7.37 (s, NH, 1H), 7.20 (d, J=8.3 Hz, 2H), 7.13 (d, J=8.5 Hz, 2H), 6.79 (d, J=8.5 Hz, 2H), 4.11 (m, 2H), 4.02 (dd, J=7.6 and 4.6 Hz, 1H), 3.60 (dq, J=9.3 and 7.0 Hz, 1H), 3.40 (dq, J=9.3 and 7.0 Hz, 1H), 3.02 (m, 3H), 2.93 (dd, J=14.1 and 7.7 Hz, 1H), 2.50 (m, 1H), 1.23 (d, J=6.9 Hz, 6H), 1.14 (t, J=7.0 Hz, 3H). ¹³C NMR (75 MHz; CDCl₃): δ 175.5, 175.3, 157.7, 136.4, 134.2, 130.5, 129.5, 128.8, 120.1, 114.4, 79.8, 68.6, 66.7, 37.9, 36.6, 35.2, 19.6, 15.0.

Example 70

(S)-2-Ethoxy-3-{4-[2-(4-isobutyrylaminophenyl) ethoxy]phenyl}propanoic Acid Ethyl Ester (a) (S)-2-Ethoxy-3-{4-[2-(4-isobutyrylaminophenyl) ethoxy]phenyl}propanoic Acid Ethyl Ester.

Azodicarbonyl dipiperidine (0.99 g; 3.93 mmole) and triphenylphosphine (1.03 g; 3.93 mmole) were added to a solution of N-[4-(2-hydroxyethyl)phenyl]isobutyramide (described in Example 68a) (0.79 g; 3.93 mmole) and (S)-2-ethoxy-3-(4-hydroxyphenyl)propanoic acid ethyl ester (described in Example 40h) (0.78 g; 3.27 mmole) in dry dichloromethane (25 ml). After stirring at room temperature over night more N-[4-(2-hydroxyethyl)phenyl] isobutyramide, azodicarbonyl dipiperidine (0.16 g; 0.65 mmole) and triphenylphosphine (0.17 g; 0.65 mmole) were added. After stirring for 24 hours the reaction mixture was filtered and the solvent was evaporated in vacuo. Purification by chromatography on silica gel using heptane:ethyl acetate (2:1) as eluant gave 1.22 g (yield 87%) of (S)-2-ethoxy-3-{4-[2-(4-isobutyrylaminophenyl)ethoxy] phenyl}propanoic acid ethyl ester.

¹H-NMR (400 MHz; CDCl₃): δ 1.17 (t, 3H, J=7 Hz), 1.20–1.26 (m, 9H), 2.55 (qvint, 1H, J=6.7 Hz), 2.95–2.98 (m, 2H), 3.03 (t, 2H, J=7 Hz), 3.33–3.41 (m, 1H), 3.57–3.65 (m, 1H), 3.98–4.02 (m, 1H), 4.12 (t, 2H, J=7 Hz), 4.17 (q, 2H, J=7 Hz), 6.82 (dm, 2H, J=8.6 Hz, unresolved), 7.15 (dm, 2H, J=8.6 Hz, unresolved), 7.20 (dm, 2H, J=8.6 Hz, unresolved), 7.53 (dm, 2H, J=8.6 Hz, unresolved). ¹³C-NMR (100 MHz; CDCl₃): δ 14.0, 14.9, 19.4, 35.0, 36.1, 38.2, 60.6, 65.9, 68.4, 80.1, 114.1, 120.0, 129.0, 129.1, 130.1, 133.7, 136.6, 157.3, 172.4, 175.6.

Example 71

(S)-2-Ethoxy-3-[4-(2-{4-isobutyrylaminophenyl}ethoxy)phenyl]propanoic Acid (S)-2-Ethoxy-3-{4-[2-(4-isobutyrylaminophenyl)ethoxy] phenyl}propanoic acid ethyl ester (described in Example 70) was hydrolyzed using the same method as in Example 2 to give (S)-2-ethoxy-3-{4-[2-(4-methanesulfonylphenyl) ethoxy]phenyl}propanoic acid.

¹H-NMR (500 MHz; CDCl₃): δ 1.17 (t, 3H, J=7 Hz), 1.70 (d, 6H, J=7.3 Hz), 2.45–2.57 (m, 1H), 2.91–2.98 (m, 1H), 3.01–3.10 (m, 1H), 3.39–3.48 (m, 1H), 3.56–3.65 (m, 1H), 4.01–4.06 (m, 1H), 4.12 (t, 2H, J=7 Hz), 6.80 (dm, 2H, J=8.8 Hz, unresolved), 7.14 (dm, 2H, J=8.8 Hz, unresolved), 7.22 (dm, 2H, J=8.3 Hz, unresolved), 7.31 (bs, 1NH), 7.47 (dm, 2H, J=8.3 Hz, unresolved). ¹³C-NMR (125 MHz; CDCl₃): δ 15.0, 19.6, 35.2, 36.6, 37.8, 66.7, 68.6, 79.8, 114.4, 120.0, 128.7, 129.4, 130.4, 134.1, 136.4, 157.7, 174.6, 175.3.

Example 72

2-Ethoxy-3-(4-{2-[4-(isobutyryl-N-methylamino) phenyl]ethoxy}phenyl)propanoic Acid Ethyl Ester 2-Ethoxy-3-{4-[2-(4-methylaminophenyl)ethoxy] phenyl}propanoic acid ethyl ester (described in Example 99) (0.477 mg; 1.28 mmole) was dissolved in a solution of isobutyric anhydride (2 ml) and pyridine (4 ml) and the reaction mixture was stirred for 2 hours at room temperature. Toluene was added and evaporated in vacuo. Purification of the crude product by chromatography on silica gel using heptane:ethyl acetate (1:1) as eluant gave 0.44 g (yield 78%) of 2-ethoxy-3-(4-{2-[4-isobutyryl-N-methylamino)phenyl] ethoxy}phenyl)propanoic acid ethyl ester.

¹H NMR (400 MHz; CDCl₃): δ 7.33 (d, J=8.2 Hz, 2H), 7.15 (d, J=8.6 Hz, 2H), 7.12 (d, J=8.2 Hz, 2H), 6.82 (d, J=8.6 Hz, 2H), 4.17 (m, 4H), 3.97 (dd, J=7.1 and 6.1 Hz, 1H), 3.60 (m, 1H), 3.35 (m, 1H), 3.23 (s, 3H), 3.11 (t, J=7.1 Hz, 2H), 2.95 (m, 2H), 2.52 (sept, J=6.7 Hz, 1H), 1.23 (t, J=7.1 Hz, 3H), 1.16 (t, J=6.9 Hz, 3H), 1.03 (d, J=6.7 Hz, 6H).

Example 73

2-Ethoxy-3-(4-{2-[4-(isobutyryl-N-methylamino) phenyl]ethoxy}phenyl)propanoic Acid Lithium hydroxide hydrate (62 mg; 1.48 mmole) dissolved in water (2 ml) was added to a solution of 2-ethoxy-3-(4-{2-[4-(isobutyryl-N-methylamino)phenyl] ethoxy}phenyl)propanoic acid ethyl ester (described in Example 72) (435 mg; 0.98 mmole) in tetrahydrofuran (6 ml). The reaction mixture was stirred at room temperature for 3 hours. The reaction mixture was acidified with hydrochloric acid (2 M) to pH 4. Tetrahydrofuran was evaporated in vacuo, water (5 ml) was added and the mixture was extracted with ethyl acetate (10 ml). The organic phase was dried (sodium sulfate) and solvent was evaporated in vacuo to give 398 mg (yield 98%) of 2-ethoxy-3-(4-{2-[4-(isobutyryl-N-methylamino)phenyl]ethoxy}phenyl) propanoic acid.

¹H-NMR (300 MHz; CDCl₃): δ 1.02 (d, 6H, J=6.6 Hz), 1.16 (t, 3H, J=7 Hz), 2,49 (qvint, 1H, J=6.6 Hz), 2.84–3.15 (m, 4H), 3.22 (s, 3H), 3.29–3.46 (m, 1H), 3.52–3.69 (m, 1H), 3.94–4.06 (m, 1H), 4.17 (t, 2H, J=6.6 Hz), 6.82 (dm, 2H, J=8.4 Hz, unresolved), 7.05–7.22 (m, 4H), 7.33 (dm, 2H, J=8 Hz, unresolved). ¹³C-NMR (75 MHz; CDCl₃): δ 15.1, 19.6, 31.0, 35.3, 37.6, 38.0, 66.6, 68.2, 79.8, 114.4, 127.2, 129.3, 130.4, 130.5, 138.3, 142.4, 157.5, 175.3, 178.0.

Example 74

(S)-2-Ethoxy-3-[4-(2-{4-(2,2-diphenylacethylamino) phenyl}ethoxy)phenyl]propanoic Acid 3-{4-[2-(4-Aminophenyl)ethoxy]phenyl}-(S)-2-ethoxypropanoic acid hydro chloride (described in Example 56a) (0.2 g; 0.547 mmole) and sodium hydrogen carbonate (0.05 g; 0.6 mmole) were mixed in tetrahydrofuran (5 ml) and stirred at room temperature for 20 minutes. 2,2-diphenylacethyl chloride (0.151 g; 0.656 mmole) was added. The reaction mixture was stirred at room temperature for 2 hours and then evaporated to dryness. Ethyl acetate and water were added to the residue and the phases were separated. The organic phase was dried with magnesium sulfate and the solvent was evaporated. Chromatography on silica gel (Isolute, SI) using dichloromethane as eluant gave crude product and further purification by column chromatography on silica gel using dichloromethane with methanol (0.5–10%) as eluant gave 0.18 g (63% yield) of (S)-2-ethoxy-3-[4-(2-{4-(2,2-diphenylacethylamino) phenyl}ethoxy)phenyl]propanoic acid.

¹H-NMR (500 MHz, DMSO-d₆): δ 0.99 (t, J=7 Hz, 3H), 2.72 (dd, J=14.3, 8 Hz, 1H), 2.86 (dd, J=14.3, 4.5 Hz, 1H), 2.93 (t, J=6.8 Hz, 2H), 3.19–3.25 (m, 1H), 3.48–3.54 (m, 1H), 3.83 (dd, J=8, 4.5 Hz, 1H), 4.08 (t, J=6.8 Hz, 2H), 5.17 (s, 1H), 6.78 (d, J=8.6 Hz, 2H), 7.10 (d, J=8.6 Hz, 2H), 7.21–7.25 (m, 4H), 7.30–7.36 (m, 8H), 7.54 (d, J=8.3 Hz, 2H) and 10.42 (s, 1H). $^{13}$C-NMR (125 MHz, DMSO-$d_6$): δ 15.23, 34.59, 37.95, 57.42, 64.65, 68.22, 80.32, 114.14(2C), 119.43(2C), 126.96(2C), 128.51(4C), 128.71(4C), 129.34 (2C), 130.32(2C), 130.48, 133.62, 137.54, 140.20(2C), 156.97, 169.89, 174.2 (found by GHMBC).

Example 75

3-{4-[2-{4-(4-[tert-Butyl]benzoyl) aminophenyl}ethoxy]phenyl}-2-(S)-ethoxypropanoic Acid 3-{4-[2-(4-Aminophenyl)ethoxy]phenyl}-(S)-2-ethoxypropanoic acid hydro chloride (described in Example 56a) (0.2 g; 0.547 mmole) was dissolved in tetrahydrofurane (5 ml). Sodium hydrogencarbonate (0.053 g; 0.631 mmole) was added and the mixture was stirred for a little while. 4-tert-Butylbenzoyl chloride (0.118 g; 0.6 mmole) was added. The reaction mixture was stirred overnight and then evaporated to dryness. Dichloromethane and water were added to the residue and the phases were separated. The organic phase was dried with magnesium sulfate and the solvent was evaporated. Chromatography of the residue on silica gel (Isolute, SI) using dichloromethane:heptane (1:1), dichloromethane and finally methanol:dichloromethane (1:99) as eluants gave 0.238 g (89% yield) of 3-{4-[2-{4-(4-[tert-butyl]benzoyl)aminophenyl}ethoxy]phenyl}-2-(S)-ethoxypropanoic acid.

$^1$H-NMR (400 MHz, $CD_3OD$): δ 1.11 (t, J=7 Hz, 3H), 1.35 (s, 9H), 2.85 (dd, J=14, 8 Hz, 1H), 2.96 (dd, J=14, 5 Hz, 1H), 3.04 (t, J=7 Hz, 2H), 3.30–3.37 (m, 1H), 3.54–3.61 (m, 1H), 3.98 (dd, J=8, 5 Hz, 1H), 4.15 (t, J=7 Hz, 2H), 6.81 (d, J=8.3 Hz, 2H), 7.14 (d, J=8.3 Hz, 2H), 7.29 (d, J=8.3 Hz, 2H), 7.54 (d, J=8.8 Hz, 2H), 7.60 (d, J=8.3 Hz, 2H) and 7.86 (d, J=8.8 Hz, 2H). $^{13}$C-NMR (150 MHz, $CD_3OD$): δ 15.31, 31.56(3C), 35.80, 36.23, 39.32, 67.12, 69.79, 81.29, 115.37 (2C), 122.44(2C), 126.51(2C), 128.48(2C), 130.34(2C), 130.76, 131.43(2C), 133.31, 136.24, 138.15, 156.51, 159.06, 168.72, 176.04.

Example 76

3-{4-[2-{4-(4-[tert-Butyl]benzoyl) aminophenyl}ethoxy]-phenyl}-2-(S)-ethoxypropanoic Acid 3-{4-[2-(4-Aminophenyl)ethoxy]phenyl}-(S)-2-ethoxypropanoic acid hydro chloride (described in Example 56a) (0.2 g; 0.547 mmole) was dissolved in tetrahydrofurane (5 ml). Sodium hydrogencarbonate (0.053 g; 0.631 mmole) was added and the mixture was stirred for a little while. 4-tert-Butylbenzoyl chloride (0.118 g; 0.6 mmole) was added. The reaction mixture was stirred overnight and then evaporated to dryness. Dichloromethane and water were added to the residue and the phases were separated. The organic phase was dried with magnesium sulfate and the solvent was evaporated. Chromatography of the residue on silica gel(Isolute, SI) using dichloromethane:heptane (1:1), then dichloromethane and finally methanol: dichloromethane (1:99) as eluants gave 0.238 g (89% yield) of 3-{4-[2-{4-(4-[tert-butyl]benzoyl)aminophenyl}ethoxy]phenyl}-2-(S)-ethoxypropanoic acid.

$^1$H-NMR (400 MHz, $CD_3OD$): δ 1.11 (t, J=7 Hz, 3H), 1.35 (s, 9H), 2.85 (dd, J=14, 8 Hz, 1H), 2.96 (dd, J=14, 5 Hz, 1H), 3.04 (t, J=7 Hz, 2H), 3.30–3.37 (m, 1H), 3.54–3.61 (m, 1H), 3.98 (dd, J=8, 5 Hz, 1H), 4.15 (t, J=7 Hz, 2H), 6.81 (d, J=8.3 Hz, 2H), 7.14 (d, J=8.3 Hz, 2H), 7.29 (d, J=8.3 Hz, 2H), 7.54 (d, J=8.8 Hz, 2H), 7.60 (d, J=8.3 Hz, 2H) and 7.86 (d, J=8.8 Hz, 2H). $^{13}$C-NMR (150 MHz, $CD_3OD$): δ 15.31, 31.56(3C), 35.80, 36.23, 39.32, 67.12, 69.79, 81.29, 115.37 (2C), 122.44(2C), 126.51(2C), 128.48(2C), 130.34(2C), 130.76, 131.43(2C), 133.31, 136.24, 138.15, 156.51, 159.06, 168.72, 176.04.

Example 77

2-(S)-Ethoxy-3-(4-{2-[4-(formylamino)phenyl] ethoxy}-phenyl)propanoic Acid Ethyl Ester Formic acid (0.0585 g, 1.27 mmole) was dissolved in dichloromethane (2 ml). Imidazole (0.0874 g; 1.27 mmole) was added into the solution, followed by addition of triethylamine (0.353 ml, 2.54 mmole). The mixture was stirred for a little while and then oxalyl chloride (0.161 g; 1.27 mmole) in dichloromethane (2 ml) was added slowly. The resulting mixture was stirred for 30 minutes. A mixture of 3-{4-[2-(4-aminophenyl)ethoxy]phenyl}-(S)-2-ethoxypropanoic acid ethyl ester hydro chloride (described in Example 41b) (0.5 g, 1.27 mmole) and triethylamine (0.176 ml; 1.27 mmole) in dichloromethane (3 ml) was added into the reaction mixture. The reaction mixture was stirred at room temperature overnight. Water was added and the phases were separated. The organic phase was washed with water, dried with magnesium sulfate and the solvent was evaporated. Chromatography of the residue on silica gel (isolute, SI) using heptane, then ethyl acetate/heptane (5%), followed by ethyl acetate/heptane (10%) and then ethyl acetate/heptane (25%) as eluants gave 0.230 g (47% yield) of 2-(S)-ethoxy-3-(4-{2-[4-(formylamino)phenyl]ethoxy}-phenyl)propanoic acid ethyl ester.

$^1$H-NMR (600 MHz, $CDCl_3$, tautomers): δ 1.14 (t, J=7 Hz, 3H), 1.21 (t, with small splits, J=7 Hz, 3H), 2.90–2.97 (m, 2H), 3.01–3.05 (m, 2H), 3.32–3.37 (m, 1H), 3.56–3.61 (m, 1H), 3.96 (dd, J=7.6, 5.6 Hz, 1H), 4.09–4.09–4.17 (m, 4H), 6.79 (d, d, J=8.7, 8.7 Hz, 2H), 7.03 (d, J=8.4 Hz, 1H), 7.12 (d, d, J=8.7, 8.4 Hz, 2H), J=7.22 (d, J=8.4 Hz, 1H), 7.25 (d, J=8.4 Hz, 1H), 7.47 (d, J=8.4 Hz, 1H), 7.84 and 8.30 (s, s, 1H), 8.41 and 8.65 (d, d, J=11.1 Hz, 11.5 Hz, 1H). $^{13}$C-NMR (125 MHz, $CDCl_3$, tautomers): δ 14.09, 14.95, 34.98(35.09), 60.72, 66.07, 68.29(68.44), 80.20, 114.23 (2C), 118.93(120.05, 2C), 129.12(129.22), 129.39, 130.12 (130.28, 2C), 130.26(2C)134.56(135.10), 135.44, 157.36 (157.41), 159.27(162.63), 172.54.

Example 78

(S)-2-Ethoxy-3-(4-{[4-(formylamino)phenethyl] oxy}phenyl)propanoic Acid

3-{4-[2-(4-Aminophenyl)ethoxy]phenyl}-(S)-2-ethoxypropanoic acid hydro chloride (described in Example 56a) (0.115 g, 0.314 mmole) in tetrahydrofuran (3 ml) was mixed with a mixture of formic acid (0.5 ml) and acetic anhydride (0.3 ml). The resulting mixture was stirred at room temperature overnight. Tetrahydrofuran was evaporated. Ethyl acetate and water were added into the residue. The phases were separated. The organic phase was washed with brine, dried with magnesium sulfate and the solvent was evaporated. Chromatography of the residue on silica gel (Isolute, SI) using dichloromethane, then methanol/dichloromethane (1%), followed by methanol/dichloromethane (2%) as eluants gave 0.07 g (yield 62%) of (S)-2-ethoxy-3-(4-{[4-(formylamino)phenethyl]oxy}phenyl)propanoic acid.

$^1$H-NMR of tautomers (500 MHz, CDCl$_3$): δ 1.21 (t, J=7 Hz, 3H), 2.97–3.12 (m, 4H), 3.43–3.49 (m, 1H), 3.64–3.71 (m, 1H), 4.07–4.10 (dd, J=7.5, 4.5 Hz, 1H), 4.12–4.17 (m, 2H), 6.82–6.86 (m, 2H), 7.07 (d, J=8.3 Hz, 2H of one tautomer), 7.18–7.21 (m, 2H), 7.26 (d, J=8.3 Hz, 2H of one tautomer), 7.30 (d, J=8.3 Hz, 2H of one tautomer), 7.52 (d, J=8.3 Hz, 2H of one tautomer), 7.85 (s, 1H of one tautomer), 8.37 (s, 1H of one tautomer), 8.64 (d, J=11.4 Hz, 1H of one tautomer), 9.12 (d, J=11.4 Hz, 1H of one tautomer). $^{13}$C-NMR of tautomers (125 MHz, CDCl$_3$): δ 14.99, 35.05 (35.15), 37.93, 66.53, 68.29(68.44), 79.78, 114.34(2C), 119.15(120.22, 2C), 128.94(129.04), 129.50(130.22, 2C), 130.42(130.44, 2C), 134.75(135.20), 135.93, 157.48 (157.54), 159.68(163.71), 175.75.

Example 79

2-{4-[2-(4-Phenylsulfanylphenyl)ethoxy]benzyl}butanoic Acid Methyl Ester (a) 2-(4-Hydroxybenzyl)butanoic Acid Methyl Ester 2-[(4-Hydroxyphenyl)methylene]butanoic acid (10.48 g; 54.5 mmol) was refluxed 24 hours in a solution of sulphuric acid (1%) in methanol (150 ml). The solvent was evaporated and water (100 ml) was added. The water phase was extracted twice with ethyl acetate, the organic phases were combined, dried (magnesiumsulfate) and the solvent was evaporated in vacuo. The crude product (9 g, 43.6 mmole) was used directly in the next step without further purification and identification.

It was hydrogenated in methanol using palladium on charcoal (5%, 3 g) as catalyst. The mixture was filtered through celite and the solvent was evaporated. Purification by chromatography on silica gel using dichloromethane:metanol (gradient 0,5–100% methanol) as eluant gave 6.8 g (yield 60% over two steps) of 2-(4-hydroxybenzyl)butanoic acid methyl ester.

$^1$H-NMR (400 MHz, CDCl$_3$): δ 0.91 (t, 3H, J=7.7 Hz), 1.55–1.84 (m, 2H), 2.57 (m, 1H), 2.68 (dd, 1H, J=6.2 Hz and 6.6 Hz), 2.82 (dd, 1H, J=6.2 Hz and 6.6 Hz), 3.61 (s, 3H), 5.58 (s, 1 OH), 6.71 (d, 2H, J=8.4 Hz), 6.99 (d, 2H, J=8.4 Hz). $^{13}$C-NMR (100 MHz, CDCl$_3$): δ 11.73, 25.09, 37.31, 49.57, 51.47, 115.22 .115.22, 129.87, 129.87, 131.26, 154.21, 176.55.

(b) 2-{4-[2-(4-Phenylsulfanylphenyl)ethoxy]benzyl}butanoic Acid Methyl Ester.

2-(4-Phenylsulfanylphenyl)ethanol (0.5 g; 2.17 mmole), azodicarbonyl dipiperidine (0.66 g, 2.6 mmole) and triphenylphosphine (0.68 g, 2.6 mmole) were dissolved in dichloromethane (20 ml) at room temperature. After stirring for 10 minutes 2-(4-hydroxybenzyl)butanoic acid methyl ester (0.54 g, 2.6 mmole) dissolved in dichloromethane (5 ml) was added. After stirring at room temperature over night more azodicarbonyl dipiperidine (0.33 g) and more triphenylphosphine (0.34 g) were added.

Solid material was filtered off after 2 hours and the filtrate was evaporated in vacuo. Purification by chromatography on silica gel using heptane:ethyl acetate (5:1) as eluant gave 0.638 g (yield 70%) of 2-{4-[2-(4-phenylsulfanylphenyl)ethoxy]benzyl}butanoic acid methyl ester.

$^1$H NMR (400 MHz; CDCl$_3$): δ 7.33–7.20 (m, 9H), 7.05 (d, J=8.3 Hz, 2H), 6.79 (d, J=8.3 Hz, 2H), 4.13 (t, J=7.0 Hz, 2H), 3.60 (s, 3H), 3.05 (t, J=7.0, 2H) 2.86, (dd, J=13.7 and 8.4 Hz, 1H), 2.68 (dd, J=13.7 and 6.5 Hz, 1H), 2.54 (m, 1H), 1.59 (m, 2H), 0.90 (t, J=7.3 Hz, 3H).

Example 80

2-{4-[2-(4-Phenylsulfanylphenyl)ethoxy]benzyl}butanoic Acid

Sodium hydroxide (3 ml, 1M) was slowly added to a solution of 2-{4-[2-(4-phenylsulfanylphenyl)ethoxy]benzyl}butanoic acid methyl ester (described in Example 79) (0.59 g, 1.4 mmole) in dioxan (12 ml). The reaction mixture was stirred at room temperature for 12 hours, then at 50° C. for 4 hours. Lithium hydroxide (50 mg) was added and the mixture was stirred at 70° C. for 24 hours. The reaction mixture was acidified with hydrochloric acid (6 M), water (20 ml) was added and the product was extracted with ethyl acetate (2×25 ml), washed with water (25 ml), dried (sodium sulfate) and the solvent was evaporated in vacuo to give 0.53 g (yield 93%) of the desired product.

$^1$H NMR (400 MHz; CDCl$_3$): δ 7.34–7.28 (m, 7H), 7.24 (d, J=8.3 Hz, 2H), 7.10 (d, J=8.7 Hz, 2H), 6.82 (d, J=8.7 Hz, 2H), 4.15 (t, J=7.0 Hz, 2H), 3.08 (t, J=7.0 Hz, 2H), 2.93 (dd, J=13.9 and 7.7 Hz, 1H), 2.72 (dd, J=13.9 and 7.0 Hz, 1H), 2.58 (m, 1H), 1.63 (m, 2H), 0.97 (t, J=7.3 Hz, 3H). $^{13}$C NMR (100 MHz; CDCl$_3$): δ 181.3, 157.3, 137.7, 136.3, 133.2, 131.6, 131.3, 130.5, 129.9, 129.8, 129.1, 126.8, 114.5, 68.3, 49.0, 36.9, 35.4, 24.7, 11.6.

Example 81

2-Ethoxy-3-{4-[2-(4-methylsulfanylphenyl)ethoxy]phenyl}propanoic Acid Ethyl Ester 2-(4-Methylsulfanylphenyl)ethanol was reacted with 2-ethoxy-3-(4-hydroxyphenyl)propanoic acid ethyl (described in Example 20b) ester using the same method as in Example 38(c) to give 2-ethoxy-3-{4-[2-(4-methylsulfanylphenyl)ethoxy]phenyl}propanoic acid ethyl ester.

$^1$H-NMR (400 MHz, CDCl$_3$): δ 1.17 (t, 3H), 1.24 (t, 3H), 2.49 (s, 3H), 2.94–2.97 (m, 2H), 3.05 (t, 2H), 3.32–3.40 (m, 1H), 3.57–3.65 (m, 1H), 3.95–3.99 (m, 1H), 4.11–4.21 (t+q, 4H), 6.82 (d, 2H), 7.15 (d, 2H), 7.2–7.28 (m, 4H).

Example 82

2-Ethoxy-3-{4-[2-(4-methylsulfanylphenyl)ethoxy]phenyl}propanoic Acid

2-Ethoxy-3-{4-[2-(4-methylsulfanylphenyl)ethoxy]phenyl}propanoic acid ethyl ester (described in Example 81) was hydrolyzed using the same method as in Example 2 but with dioxane instead of tetrahydrofuran to give 2-ethoxy-3-{4-[2-(4-methylsulfanylphenyl)ethoxy]-phenyl}propanoic acid.

$^1$H-NMR (400 MHz, CDCl$_3$): δ 1.19 (t, 3H), 2.49 (s, 3H), 2.92–2.99 (dd, 1H) 3.03–3.11 (dd+t, 3H), 3.41–3.50 (m, 1H), 3.59–3.65 (m, 1H), 4.04–4.07 (dd, 1H), 4.14 (t, 2H), 6.83 (d, 2H), 7.16 (d, 2H), 7.20–7.28 (m, 4H). $^{13}$C-NMR (100 MHz; CDCl$_3$): δ 16.1, 17.3, 36.4, 38.8, 68.0, 69.6, 80.9, 115.5, 128.2, 129.7, 130.6, 131.6, 136.4, 137.3, 158.8, 175.9.

Example 83

3-{4-[2-(4-Methylsulfanylphenyl)ethoxy]phenyl}-2-phenoxypropanoic Acid Methyl Ester (a) 3-(4-Benzyloxyphenyl)-2-phenoxypropanoic Acid Methyl Ester 3-(4-Benzyloxyphenyl)-2-hydroxypropanoic acid methyl ester was reacted with phenol using the same method as in Example 38(c) to give 3-(4-benzyloxyphenyl)-2-phenoxypropanoic acid methyl ester.

$^1$H-NMR (400 MHz, CDCl$_3$): δ 3.21 (m, 2H), 3.70 (s, 3H), 4.80 (dd, 1H, J=5.4 Hz; 7.3 Hz), 5.31 (s, 2H), 6.86 (dm, 2H, J=7.8 Hz, unresolved), 6.96 (m, 3H), 7.25 (m, 4H), 7.38 (m, 5H).

(b) 3-(4-Hydroxyphenyl)-2-phenoxypropanoic Acid Methyl Ester 3-(4-Benzyloxyphenyl)-2-phenoxypropanoic acid methyl ester (0.47 g; 1.3 mmole) was hydrogenated in ethyl acetate (20 ml) using Pd/C (18 mg; 5%) as catalyst at atmospheric pressure and room temperature for 23 hours. As the reaction was very slow, the catalyst was changed to palladium hydroxide, ethanol (95%, 10 ml) was added and the pressure was raised to 4 bar. The reaction mixture was filtered through celite and the filtrate was concentrated in vacuo to give 0.34 g (yield 95%) of 3-(4-hydroxyphenyl)-2-phenoxypropanoic acid methyl ester.

$^1$H-NMR (400 MHz; CDCl$_3$): δ 3.19 (m, 2H), 3.72 (s, 3H), 4.79 (dd, 1H, J=5.4 Hz; 7.3 Hz), 6.76 (dm, 2H, J=8.3 Hz, unresolved), 6.85 (dd, 2H, J=1.0 Hz; 8.8 Hz), 6.97 (m, 1H), 7.16 (dm, 2H, J=8.8 Hz, unresolved), 7.27 (m, 2H).

(c) 3-{4-[2-(4-Methylsulfanylphenyl)ethoxy]phenyl}-2-phenoxypropanoic Acid Methyl Ester 3-(4-Hydroxyphenyl)-2-phenoxypropanoic acid methyl ester was reacted with 2-(4-methylsulfanylphenyl)ethanol using the same methods as in Example 38(c) to give 3-{4-[2-(4-methylsulfanylphenyl)ethoxy]phenyl}-2-phenoxypropanoic acid methyl ester.

$^1$H-NMR (400 MHz; CDCl$_3$): δ 2.50 (s, 3H), 3.07 (t, 2H, J=7.0 Hz), 3.22 (m, 2H), 3.74 (s, 3H), 4.16 (t, 2H, J=7.0 Hz), 4.81 (dd, 1H, J=5.2 Hz; 7.5 Hz), 6.87 (m, 4H), 6.99 (t, 1H, J=7.5 Hz), 7.26 (m, 8H).

Example 84

3-{4-[2-(4-Methylsulfanylphenyl)ethoxy]phenyl}-2-phenoxypropanoic Acid

3-{4-[2-(4-Methylsulfanylphenyl)ethoxy]phenyl}-2-phenoxypropanoic acid methyl ester (described in Example 83) was hydrolyzed using the same method as in Example 2 to give 3-{4-[2-(4-methylsulfanyl-phenyl)ethoxy]phenyl}-2-phenoxypropanoic acid.

$^1$H-NMR (400 MHz; CDCl$_3$): δ 2.50 (s, 3H), 3.07 (t, 2H, J=7.3 Hz), 3.26 (d, 2H, J=6.4 Hz), 4.15 (t, 2H, J=6.8 Hz), 4.84 (t, 1H, J=5.4 Hz), 6.88 (m, 4H), 7.05 (dt, 1H, J=1.0 Hz; 7.3 Hz), 7.27 (m, 8H). $^{13}$C-NMR (100 MHz; CDCl$_3$): δ 17.3, 36.3, 39.1, 69.7, 78.7, 115.7, 116.5, 123.2, 128.2, 129.3, 130.6, 130.8, 131.7, 136.4, 137.4, 158.6, 160.0, 177.9.

Example 85

(S)-2-Ethoxy-3-(4-{2-[4-(phenylsulfanyl)phenyl]ethoxy}phenyl)propanoic Acid Ethyl Ester 2-[4-(Phenylsulfanyl)phenyl]-1-ethanol (1.22 g; 5.12 mmole), triphenylphosphine (2 g; 7.6 mmole) and 1,1'-(azodicarbonyl)dipiperidine were dissolved in dichloromethane (15 ml). After 10 minutes a solution of (S)-2-ethoxy-3-(4-hydroxyphenyl)propanoic acid (described in Example 40b) in dichloromethane (15 ml) was added and the reaction mixture was stirred over night at room temperature. The solid material was filtered off and the solvent evaporated. Chromatography of the residue on siliga gel using ethyl acetate:petroleum ether (40–60° C.), (1:99, 5:95 and 10:90) gave 1.24 g (yield 47%) of (S)-2-ethoxy-3-(4-{2-[4-(phenylsulfanyl)phenyl]ethoxy}phenyl)propanoic acid ethyl ester.

$^1$H-NMR (500 MHz; CDCl$_3$): δ 1.21 (t, 3H), 1.28 (t, 3H), 3.00 (m, 2H), 3.11 (m, 2H), 3.40 (m, 1H), 3.65 (m, 1H), 4.01 (m, 1H), 4.16–4.24 (m, 4H), 6.86 (d, 2H), 7.19 (d, 2H), 7.26–7.38 (m, 9H).

Example 86

(S)-2-Ethoxy-3-(4-{2-[4-(phenylsulfanyl)phenyl]ethoxy}phenyl)propanoic Acid (S)-2-Ethoxy-3-(4-{2-[4-(phenylsulfanyl)phenyl]ethoxy}phenyl)propanoic acid ethyl ester (described in Example 85) (0.55 g; 1.22 mmole) was dissolved in tetrahydrofuran (5 ml) and water (5 ml). Lithium hydroxide (0.035 g; 1.46 mmole) was added and the solution was stirred at room temperature 24 hours. Aqueous hydrochloric acid was added to the solution until pH=1. The solvent was evaporated and the residue was redissolved in water and diethyl ether. The phases were separated and the organic layer was washed once with water and dried with sodium sulfate. The solvent was evaporated. Chromatography of the residue on siliga gel using diethyl ether:ethanol (95:5) as eluant gave 0.40 g (yield 78%) of (S)-2-ethoxy-3-(4-{2-[4-(phenylsulfanylphenyl]ethoxy}phenyl)propanoic acid.

$^1$H-NMR (400 MHz; CDCl$_3$): δ 1.18 (t, 3H), 2.97 (m, 1H), 3.07 (m, 3H), 3.42 (m, 1H), 3.63 δ (m, 1H), 4.04 (m, 1H), 4,15 (m, 2), 6.83 (d, 2H), 7.17 (d, 2H), 7.20–7.26 (m, 3H), 7.26–7.35 (m, 6H).

Example 87

2-Ethoxy-3-{4-[2-(4-methanesulfonylphenyl)ethoxy]phenyl}propanoic Acid Ethyl Ester 3-Chloroperoxybenzoic acid (0.73 g; 4.20 mmole) was added to a solution of 2-ethoxy-3-{4-[2-(4-methylsulfanylphenyl)ethoxy]phenyl}propanoic acid ethyl ester (described in Example 81) (0.65 g; 1.68 mmole) in dichloromethane (20 ml) at 0° C. After stirring at room temperature for 3 hours, water (20 ml) was added. The mixture was extracted with ethyl acetate (20 ml), washed with saturated sodium bicarbonate, dried (sodium sulfate) filtered and the solvent was evaporated in vacuo. Purification by chromatography on silica gel using heptane:ethyl acetate (1:1) as eluant gave 0.399 g (yield 56%) of 2-ethoxy-3-{4-[2-(4-methanesulfonylphenyl)ethoxy]phenyl}propanoic acid ethyl ester slightly polluted by 3-chloroperoxybenzoic acid.

$^1$H NMR (600 MHz; CDCl$_3$): δ 7.89 (d, J=8.3 Hz, 2H), 7.49 (d, J=8.3 Hz, 2H), 7.15 (d, J=8.7 Hz, 2H), 6.80 (d, J=8.7 Hz, 2H), 4.19 (t, J=6.5 Hz, 2H), 4.17 (m, 2H), 3.96 (dd, J=7.4 and 5.8 Hz, 1H), 3.60 (m, 1H), 3.34 (m, 1H), 3.17 (t, J=6.5, 2H), 3.05 (s, 3H), 2.95 (m, 2H), 1.23 (t, J=7.1, 3H), 1.16 (t, J=7.0 Hz, 3H).

Example 88

2-Ethoxy-3-{4-[2-(4-methanesulfonylphenyl)ethoxy]phenyl}propanoic Acid

Lithium hydroxide hydrate (57 mg; 1.37 mmole) dissolved in water (2 ml) was added to a solution of 2-ethoxy-3-{4-[2-(4-methanesulfonylphenyl)ethoxy]phenyl}propanoic acid ethyl ester (described in Example 87) (384 mg; 0.91 mmole) in tetrahydrofuran 6 ml. After stirring at room temperature for 2 hours more lithium hydroxide hydrate (30 mg) dissolved in water (1 ml) was added. The reaction mixture was stirred at room temperature for 4 more hours. The reaction mixture was acidified with hydrochloric acid (2 M) to pH 4. Tetrahydrofuran was evaporated in vacuo, water (5 ml) was added and the product was extracted with ethyl acetate (10 ml). The organic phase was washed with water, dried (sodium sulfate) and the solvent was evaporated in vacuo. Purification by chromatography on silica gel using heptane:ethyl acetate:acetic acid (10:10:1) as eluant gave 0.307 g (yield 86%) of 2-ethoxy-3-{4-[2-(4-methanesulfonylphenyl)ethoxy]phenyl}propanoic acid as a pale yellow oil that crystallizes when vacuum dried.

$^1$H-NMR (300 MHz; CDCl$_3$): δ 1.16 (t, 3H, J=7 Hz), 2.87–3.10 (m, 5H), 3.16 (t, 2H, J=6.4 Hz), 3.36–3.48 (m,

1H), 3.53–3.66 (m, 1H), 3.98–4.07 (m, 1H), 4.18 (t, 2H, J=6.4 Hz), 6.75–6.85 (m, 2H), 7.10–7.20 (m, 2H), 7.46–7.55 (m, 2H), 7.86–7.96 (m, 2H). $^{13}$C-NMR (75 MHz; CDCl$_3$): δ 11.4, 35.7, 37.8, 44.6, 66.7, 67.6, 79.8, 114.4, 127.5, 129.0, 129.1, 130.0, 130.6, 145.2, 157.4, 175.4.

Example 89

(S)-2-Ethoxy-3-(4-{2-[4-(phenylsulfonyl)phenyl] ethoxy}phenyl)propanoic Acid Ethyl Ester (S)-2-Ethoxy-3-(4-{2-[4-(phenylsulfanyl)phenyl] ethoxy}phenyl)propanoic acid ethyl ester (described in Example 85) (0.6 g; 1.33 mmole) was dissolved in methylene chloride (10 ml) and 3-chloroperbenzoic acid was added. The solution was stirred 2 hours at 60° C. Participated between water and diethyl ether. The organic layer was washed three times with water, dried with sodium sulfate and the solvent was evaporated. Chromatography of the residue, gradient eluation with diethyl ether: petroleum ether (40–60° C.) 33:67, 50:50 and 67:33 gave 0.31 g (yield 48%) of (S)-2-ethoxy-3-(4-{2-[4-(phenylsulfonyl)phenyl] ethoxy}phenyl)propanoic acid ethyl ester.

Example 90

(S)-2-Ethoxy-3-(4-{2-[4-(phenylsulfonyl)phenyl] ethoxy}phenyl)propanoic Acid (S)-2-Ethoxy-3-(4-{2-[4-(phenylsulfonyl)phenyl] ethoxy}phenyl)propanoic acid ethyl ester (described in Example 89) (0.34 g; 0.70 mmole) was dissolved in THF (5 ml) and water (5 ml). Lithium hydroxide was added to the solution (0.022 g; 0.092 mmole) and the solution was stirred over night at room temperature. Aqueous hydrochloric acid was added until pH=3–4. The solvent was evaporated to a small volume. The remaining product was participated between water and diethyl ether. The water layer was once extracted with diethyl ether. The organic phase was dried with sodium sulfate and the solvent evaporated. Chromatography of the crude product, gradient eluation (99:1, 95:5 and 90:10). The product was isolated as a viscous oil. The oil was dissolved in water and acetonitrile and freezed by liquid nitrogen. Freeze-drying for 24 hours gave 0.18 g (yield 56%) of (S)-2-ethoxy-3-(4-{2-[4-(phenylsulfonyl) phenyl]ethoxy}phenyl)propanoic acid.

$^1$H-NMR (400 MHz; CDCl$_3$): δ 1.07 (t, 3H), 2.83–2.95 (m, 1H), 2.95–3.10 (m, 3H), 3.30–3.44 (m, 1H), 3.44–3.58 (m, 1H), 3.91–4.01 (m, 1H), 4.02–4.13 (m, 2H), 6.72 (d, 2H), 7.10 (d, 2H), 7.37 (d, 2H), 7.43–7.56 (m, 3H), 7.85 (d, 2H), 7.92 (d, 2H).

$^1$H-NMR (500 MHz; CDCl$_3$): δ 1.15 (t, 3H), 1.22 (t, 3H), 2.93 (m, 2H), 3.11 (t, 2H), 3.37 (m, 1H), 3.62 (m, 1H), 3.98 (m, 1H), 4.14–4.22 (m, 4H), 6.76 (d, 2H), 7.13 (d, 2H), 7.42 (d, 2H), 7.50 (d, 2H), 7.56–7.62 (m, 1H), 7.91 (d, 2H), 7.97 (d, 2H).

Example 91

3-{4-[2-(4-tert-Butylcarbamoyloxyphenyl)ethoxy] phenyl}-2-ethoxypropanoic Acid Ethyl Ester tert-Butyl isocyanate (0.14 g; 1.4 mmole) was slowly added to a solution of 2-ethoxy-3-{4-[2-(4-hydroxyphenyl) ethoxy]phenyl}propanoic acid ethyl ester (described in Example 26b) (0.5 g; 1.4 mmole) in toluene (5 ml) and thereafter the reaction mixture was stirred over night. The crude mixture was purified by chromatography on silica gel using ethyl acetate:heptane (gradient 1.25–80% ethyl acetate) as eluant to give 0.13 g (yield 20%) of 3-{4-[2-(4-tert-butylcarbamoyloxyphenyl)ethoxy]phenyl}-2-ethoxypropanoic acid ethyl ester.

$^1$H-NMR (500 MHz; CDCl$_3$): δ 1.16 (t, 3H, J=7 Hz), 1.20 (t, 3H, J=7 Hz), 1.38 (s, 9H), 2.92–2.99 (m, 2H), 3.05 (t, 2H, J=7 Hz), 3.31–3.38 (m, 1H), 3.55–3.64 (m, 1H), 3.94–3.99 (m, 1H), 4.0 (t, 2H, J=7 Hz), 4.16 (q, 2H, J=7 Hz), 5.10 (bs, NH), 6.80 (dm, 2H, J=8.5 Hz, unresolved), 7.05 (dm, 2H, J=8.5 Hz, unresolved), 7.14 (dm, 2H, J=8.5 Hz, unresolved), 7.25 (dm, 2H, J=8.5 Hz, unresolved). $^{13}$C-NMR (125 MHz; CDCl$_3$): δ 14.9, 35.0, 37.8, 66.6, 67.9, 79.6, 114.2, 115.3, 121.9, 124.2, 129.0, 129.8, 130.4, 138.3, 140.9, 147.7, 150.8, 157.4, 176.3.

Example 92

3-{4-[2-(4-tert-Butylcarbamoyloxyphenyl)ethoxy] phenyl}-2-ethoxypropanoic Acid

3-{4-[2-(4-tert-Butylcarbamoyloxyphenyl)ethoxy] phenyl}-2-ethoxypropanoic acid ethyl ester (described in Example 91) was hydrolyzed using the same method as in Example 2 to give 3-{4-[2-(4-tert-butylcarbamoyloxyphenyl)ethoxy]phenyl}-2-ethoxypropanoic acid.

$^1$H-NMR (400 MHz; CDCl$_3$): δ 1.17 (t, 3H, J=7 Hz), 1.32 (s, 9H), 2.90–2.97 (m, 2H), 3.01 (t, 2H, J=7 Hz), 3.40–3.50 (m, 1H), 3.53–3.65 (m, 1H), 4.03 (m, 1H), 4.10 (t, 2H, J=7 Hz), 6.79 (dm, 2H, J=8.5 Hz, unresolved), 6.81 (dm, 2H, J=8.5 Hz, unresolved), 7.11–7.16 (m, 4H).

Example 93

3-{4-[2-(4-benzylcarbamoyloxyphenyl)ethoxy] phenyl}-2-ethoxy-propanoic Acid Ethyl Ester 2-Ethoxy-3-{4-[2-(4-hydroxyphenyl)ethoxy] phenyl}propanoic acid ethyl ester (described in Example 26b) (0.36 g; 1.0 mmol) was dissolved in dry dichloromethane (25 ml) and benzylisocyanate (0.20 g; 0.185 ml; 1.5 mmol) was added followed by addition of triethylamine (0.22 ml; 1.5 mmol). The solution was stirred at room temperature for 3 hours. The dichloromethane phase was washed with diluted acid, sodium hydrogen carbonate and brine, dried with sodium sulfate and evaporated to give 0.4 g (81%) of crude 3-{4-[2-(4-benzylcarbamoyloxyphenyl) ethoxy]phenyl}-2-ethoxypropanoic acid ethyl ester. The crude material was purified on preparative reversed phase HPLC using a gradient of acetonitrile-water-ammonium acetate as mobile phase. Fractions containing pure product were pooled and the acetonitrile removed in vacuum. The residue was dissolved in dichloromethane, washed with water, dried with sodium sulfate and evaporated to give 0.23 g (48%) of pure 3-{4-[2-(4-benzylcarbamoyloxyphenyl) ethoxy]phenyl}-2-ethoxypropanoic acid ethyl ester $^1$H-NMR (300 MHz, CDCl$_3$): δ 1.19 (t, 3H); 1.25 (t, 3H); 2.97 (d, 2H); 3.08 (t, 2H); 3.31–3.44 (m, 1H); 3.56–3.69 (m, 1H); 3.99 (t, 1H); 4.14 (t, 2H); 4.18 (q, 2H); 4.45 (s, 2H); 6.83 (d, 2H), 7.11 (d, 2H); 7.17 (d, 2H); 7.29 (d, 2H); 7.32–7.42 (m, 5H); $^{13}$C-NMR ((75 MHz, CDCl$_3$): δ 14.2, 15.0, 35.1, 38.4, 45.1, 60.7, 66.1, 68.4, 80.3, 114.2, 121.4, 127.4, 127.5, 128.6, 129.2, 129.7, 130.2, 135.2, 137.9, 149.5, 154.6, 157.3, 172.4.

Example 94

2-Ethoxy-3-{4-[2-(4-phenylcarbamoyloxyphenyl) ethoxy]phenyl}propanoic Acid Ethyl Ester 2-Ethoxy-3-{4-[2-(4-phenylcarbamoyloxyphenyl) ethoxy]phenyl}propanoic acid ethyl ester was prepared as described in example Example (93 starting from 2-ethoxy-3-{4-[2-(4-hydroxyphenyl)ethoxy]phenyl}propanoic acid ethyl ester (0.18 g; (0.5 mmol) (described in Example (26b), phenylisocyanate ((0.18 g; (0.16 ml; (1.5 mmol) and triethylamine ((0.22 ml; (1.6 mmol) in dry dichloromethane ((25 ml). After preparative reversed phase HPLC using a gradient of acetonitrile-water-ammonium acetate as mobile phase 0.073 g (30%) of pure 2-ethoxy-3-{4-[2-(4-phenylcarbamoyloxyphenyl)ethoxy]phenyl}propanoic acid ethyl ester was obtained.

$^1$H-NMR ((500 MHz, CDCl$_3$): δ 1.19 (t, 3H); 1.25 (t, 3H); 2.98 (d, 2H); 3.10 (t, 2H); 3.34–3.43 (m, 1H); 3.58–3.68 (m, 1H); 4.00 (t, 1H); 4.16 (t, 2H); 4.19 (q, 2H); 6.84 (d, 2H); 7.11 (t, (1H); 7.16 (d, 2H); 7.17 (d, 2H); 7.32 (d, 2H); 7.35 (t, 2H); 7.46 (d, 2H); 7.08 (bs, 1H); $^3$C-NMR (100.6 MHz, CDCl$_3$): δ 14.2, 15.0, 35.1, 38.4, 60.8, 66.2, 68.5, 80.4, 114.3, 118.7, 121.6, 123.8, 129.1, 129.3, 129.9, 130.4, 135.8, 137.38, 149.1, 151.7, 157.5, 172.5.

Example 95

3-[4-(2-[4-({Benzylamino}carbonylamino)phenyl]ethoxy)phenyl]-(S)-2-ethoxypropanoic Acid 3-{4-[2-(4-Aminophenyl)ethoxy]phenyl}-(S)-2-ethoxypropanoic acid hydro chloride (described in Example 56a) (0.2 g; 0.547 mmole) and sodium hydrogen carbonate (0.053 g; 0.631 mmole) were mixed in tetrahydrofuran (5 ml) and stirred at room temperature for 20 minutes. Benzyl isocyanate (0.087 g; (0.653 mmole) was added. The reaction mixture was stirred at room temperature for 5 hours and then evaporated to dryness. Dichloromethane and water were added to the residue and the phases were separated. The organic phase was dried with magnesium sulfate and the solvent was evaporated.

Chromatography on silica gel (Isolute, SI) using dichloromethane and then methanol (1%) in dichloromethane as eluant gave 0.19 g (75% yield) of 3-[4-(2-[4-({benzylamino}carbonylamino)phenyl]ethoxy)phenyl]-(S)-2-ethoxypropanoic acid $^1$H-NMR ((500 MHz, CDCl$_3$): δ 1.19 (t, J=7 Hz, 3H), 2.97 (dd, J=14.5, 7.5 Hz, 1H), 3.02 (t, J=7 Hz, 2H), 3.07 (dd, J=14.5, 4.5 Hz, 1H), 3.44–3.50 (m, 1H), 3.59–3.65 (m, 1H), (4.06 (dd, J=7.5, 4.5 Hz, 1H), 4.10 (t, J=7 Hz, 2H), 4.43 (d, J=4.5 Hz, 2H), 5.30 (br, 1H), 6.78 (d, J=8.5 Hz, 2H), 7.02 (br, 1H), 7.14 (d, J=8.5 Hz, 2H), 7.18 (d, J=8.5 Hz, 2H), 7.21 (d, J=8.5 Hz, 2H), 7.26–7.35 (m, 5H). $^{13}$C-NMR (125 MHz, CDCl$_3$): δ 15.01, 35.10, 37.91, 44.09, 66.49, 68.44, 79.81. 114.34(2C), 121.99(2C), 127.28, 127.33(2C), 128.58(2C), 128.85, 129.79(2C), 130.42(2C), 134.31, 136.41, 138.77, 156.94, 157.53, 175.37.

Example 96

(S)-2-Ethoxy-3-[4-(2-{4-[({4-[(trifluoromethyl)sulfanyl]anilino}carbonyl)amino]phenyl}ethoxy)phenyl]propanoic Acid 3-{4-[2-(4-Aminophenyl)ethoxy]phenyl}-(S)-2-ethoxypropanoic acid hydro chloride (described in Example 56a) (0.2 g; (0.547 mmole) was dissolved in tetrahydrofuran (5 ml). Sodium hydrogencarbonate (0.051 g; 0.607 mmole) was added and the mixture was stirred for a little while. 4-(Trifluoromethylthio)phenyl isocyanate (0.126 g; 0.575 mmole) was added. The reaction mixture was stirred at room temperature for 6 hours and then evaporated to dryness. Ethyl acetate and water were added to the residue and the phases were separated. The organic phase was dried with magnesium sulfate and the solvent was evaporated. Chromatography of residue on silica gel (isolute, SI) using dichloromethane, methanol:dichloromethane (1:99) and then methanol:dichloromethane (2:98) as eluants gave 0.17 g (57% yield) of (S)-2-ethoxy-3-[4-(2-{4-[({4-[(trifluoromethyl)sulfanyl]anilino}carbonyl)amino]phenyl}ethoxy)phenyl]propanoic acid.

$^1$H-NMR(400 MHz, CD$_3$OD): δ 1.09 (t, J=7 Hz, 3H), 2.84 (dd, J=14, 8 Hz, 1H), 2.93–2.98 (m, 3H), 3.28–3.36 (m, 1H), 3.53–3.60 (m, 1H), 3.97 (dd, 8, 5 Hz, 1H), 4.08 (t, J=7.5 Hz, 2H), 6.77 (d, J=8.5 Hz, 2H), 7.12 (d, J=8.5 Hz, 2H), 7.20 (d, J=8.5 Hz, 2H), 7.35 (d, J=8.5 Hz, 2H), 7.54 (s, 4H). $^{13}$C-NMR (125 MHz, CD$_3$OD): δ 15.31, 36.11, 39.30, 67.12, 69.82, 81.28, 115.34(2C), 117.06, 120.40(2C), 120.76(2C), 130.47(2C), 130.70, 131.17 (q, J=305 Hz), 131.41(2C), 134.77, 138.35, 138.55(2C), 143.93, 154.82, 159.04, 176.12.

Example 97

3-{4-[2-(4-[(tert-Butylamino)carbonyl]aminophenyl)ethoxy]phenyl}-2-(S)-ethoxypropanoic Acid 3-{4-[2-(4-Aminophenyl)ethoxy]phenyl}-(S)-2-ethoxypropanoic acid hydro chloride (described in Example 56a) (0.2 g; 0.547 mmole) and sodium hydrogen carbonate (0.053 g; 0.631 mmole) were mixed in tetrahydrofuran (5 ml) and stirred at room temperature for 20 minutes. 4-tert-Butylisocyanate (0.059 g; 0.595 mmole) was added. The reaction mixture was stirred at room temperature overnight and then evaporated to dryness. Dichloromethane and water were added to the residue and the phases were separated. The organic phase was dried with magnesium sulfate and the solvent was evaporated. Chromatography on silica gel (Isolute, SI) using heptane/dichloromethane(50%), then dichloromethane followed by methanol/dichloromethane (1%) as eluants gave 0.15 g (64% yield) of 3-{4-[2-(4-[(tert-butylamino)carbonyl]aminophenyl)ethoxy]phenyl}-2-(S)-ethoxypropanoic acid.

$^1$H-NMR (600 MHz, CD$_3$OD): δ 1.10 (t, J=7 Hz, 3H), 1.34 (s, 9H), 2.84 (dd, J=14, 8 Hz, 1H), 2.92–2.96 (m, 3H), 3.29–3.34 (m, 1H), 3.54–3.59 (m, 1H), 3.96 (dd, J=8, 4.5 Hz, 1H), 4.06 (t, J=7 Hz, 2H), 6.78 (d, J=8.4 Hz, 2H), 7.11 (d, J=8.4 Hz, 2H), 7.14 (d, J=8.4 Hz, 2H) and 7.22 (d, J=8.4 Hz, 2H). $^{13}$C-NMR (150 MHz, CDCl$_3$): δ 15.31, 29.66 (3C), 36.08, 39.31, 51.04, 67.11, 69.94, 81.29, 115.35(2C), 120.18 (2C), 130.31(2C), 130.69, 131.40(2C), 133.56, 139.35, 157.46, 159.06 and 176.07.

Examples 98 and 99

2-Ethoxy-3-{4-[2-(4-methylaminophenyl)ethoxy]phenyl}propanoic Acid Ethyl Ester and 3-{4-[2-(4-Dimethylaminophenyl)ethoxy]phenyl}-2-ethoxypropanoic Acid Ethyl Ester Formaldehyde (0.273 ml; 3,36 mmole, 37 wt. % solution in water) and Pd/C (100 mg, 10%) were added to a solution of 3-{4-[2-(4-aminophenyl)ethoxy]phenyl}-2-ethoxypropanoic acid ethyl ester (described in Example 62a) (0.96 g; 2,69 mmole) in ethyl acetate (15 ml) and then hydrogenated at atmospheric pressure and room temperature for 4 hours. Filtration through celite and purification by chromatography on silica gel using heptane:ethyl acetate (gradient 4:1 to 1:1) as eluant gave 0.49 g (yield 49%) of 2-ethoxy-3-{4-[2-(4-methylaminophenyl)ethoxy]phenyl}propanoic acid ethyl ester and 0.24 g (yield 23%) of 3-{4-[2-(4-dimethylaminophenyl)ethoxy]phenyl}-2-ethoxypropanoic acid ethyl ester.

2-Ethoxy-3-{4-[2-(4-methylaminophenyl)ethoxy]phenyl}propanoic acid ethyl ester $^1$H NMR (400 MHz; CDCl$_3$): δ 7.13 (d, J=8.5 Hz, 2H), 7.10 (d, J=8.5 Hz, 2H), 6.81 (d, J=8.5 Hz, 2H), 6.58 (d, J=8.5 Hz, 2H), 4.16 (q, J=7.1 Hz, 2H), 4.08 (t, J=7.4 Hz, 2H), 3.96 (dd, J=7.3 and 5.9 Hz, 1H), 3.59 (dq, J=9.2 and 7.0, 1H), 3.34 (dq, J=9.2 and 7.0 Hz, 1H), 2.98 (t, J=7.4 Hz, 2H), 2.94 (m, 2H), $^{13}$C NMR (100 MHz; CDCl$_3$): δ 172.6, 157.7, 147.9, 130.3, 129.7, 129.1, 126.8, 114.3, 112.6, 80.5, 69.2, 66.2, 60.7, 38.5, 34.9, 30.9, 15.1, 14.2.

3-{4-[2-(4-Dimethylaminophenyl)ethoxy]phenyl}-2-ethoxypropanoic acid ethyl ester $^1$H NMR (500 MHz; CD$_3$OD): δ 7.12 (d, J=8.6 Hz, 2H), 7.10 (d, J=8,6 Hz, 2H), 6.80 (d, J=8.6 Hz, 2H), 6.75 (d, J=8.6 Hz, 2H), 4.11 (q, J=7.1 Hz, 2H), 4.07 (t, J=7.0 Hz, 2H), 4.01 (dd, J=7.5 and 5.7 Hz, 1H), 3.55 (m, 1H), 3.36 (m, 1H), 2.93 (t, J=7.0 Hz, 2H), 2.91 (m, 2H), 2.87 (s, 6H), 1.17 (t, J=7.1 Hz, 3H), 1.12 (t, J=7.0 Hz, 3H).

Example 100

3-{4-[2-(4-Dimethylaminophenyl)ethoxy]phenyl}-2-ethoxypropanoic Acid

Lithium hydroxide hydrate (38 mg; 0.90 mmole) dissolved in water (2 ml) was added to a solution of 3-{4-[2-(4-dimethylaminophenyl)ethoxy]phenyl}-2-ethoxypropanoic acid ethyl ester (described in Example 99) (232 mg; 0.60 mmole) in tetrahydrofuran (6 ml). The reaction mixture was stirred at room temperature for 3 hours. The reaction mixture was acidified with hydrochloric acid (2 M) to pH 5. Tetrahydrofuran was evaporated in vacuo, water (5 ml) was added and the mixture was extracted with ethyl acetate (10+5 ml), dried (sodium sulfate) and the solvent was evaporated in vacuo. Purification by filtration on silica gel gave 180 mg (yield 84%) of 3-{4-[2-(4-dimethylaminophenyl)ethoxy]phenyl}-2-ethoxypropanoic acid.

$^1$H NMR(600 MHz; CDCl$_3$): δ 7.15 (d, J=8.3 Hz, 2H), 7.13 (d, J=8.3 Hz, 2H), 6.81 (d, J=8.3 Hz, 2H), 6.74 (d, J=8.3 Hz, 2H), 4.12 (t, J=7.3 Hz, 2H), 4.03 (m, 1H), 3.59 (m, 1H), 3.42 (m, 1H), 3.06 (dd, J=14.1 and 3.8, 1H), 2.99 (t, J=7.3 Hz, 2H), 2.93 (m, 1H), 2.92 (s, 6H), 1.16 (t, J=7.0 Hz, 3H). $^{13}$C NMR(150 MHz; CDCl$_3$): δ 174.9, 157.8, 149.4, 130.4, 129.6, 128.6, 126.6, 114.4, 113.3, 79.9, 69.1, 66.8, 41.0, 37.8, 34.8, 15.0.

Example 101

(S)-2-Ethoxy-3-(4-{2-[4-({3-[(4-methylphenyl)sulfonyl]-3-phenyl-(R/S)-propyl}amino)phenyl]ethoxy}phenyl)propanoic Acid 3-Phenyl-3-(4-methylphenyl)propionaldehyde (0.166 g; 0.57 mmole) was dissolved in tetrahydrofurane(3 ml) and sulfuric acid (4 M; 0.041 ml; 0.164 mmole) was added under stirring, followed by addition of 3-{4-[2-(4-aminophenyl)ethoxy]phenyl}-(S)-2-ethoxypropanoic acid hydro chloride (described in Example 56a) (0.2 g; 0.547 mmole) dissolved in tetrahydrofurane(2 ml). The reaction mixture was stirred for 10 minutes, then cooled to 0° C. in an ice-bath and sodium borohydride (0.042 g; 1.10 mmole) was added. After addition, the cooling bath was removed. The mixture was stirred overnight and then evaporated to remove tetrahydrofurane. Ethyl acetate and water were added into the residue and the organic phase was separated, washed with brine, dried with magnesium sulfate. The solvent was then evaporated. Chromatography on silica gel (Isolute, SI ) using dichloromethane and then methanol (1%) in dichloromethane as eluant gave 0.13 g (40% yield) of (S)-2-ethoxy-3-(4-{2-[4-({3-[(4-methylphenyl)sulfonyl]-3-phenyl-(R/S)-propyl}amino)phenyl]ethoxy}phenyl)propanoic acid.

$^1$H-NMR(500 MHz, CDCl$_3$): δ 1.18 (t, J=7 Hz, 3H), 2.39 (s, 3H), 2.39–2.46 (m, 1H), 2.71–2.78 (m, 1H), 2.92–3.00 (m, 3H), 3.05–3.11 (m, 2H), 3.15–3.22 (m, 1H), 3.43–3.50 (m, 1H), 3.56–3.63 (m, 1H), 4.04–4.10 (m, 3H), 4.24 (dd, J=10.6, 3.9 Hz, 1H), 6.45 (d, J=8.5 Hz, 2H), 6.83 (d, J=8.5 Hz, 2H), 7.05 (d, J=8.5 Hz, 2H), 7.11–7.20 (m, 4H), 7.25–7.34 (m, 5H), 7.39 (d, J=8.5 Hz, 2H). $^{13}$C-NMR(125 MHz, CDCl$_3$): δ 15.03, 21.58, 27.99, 34.89, 37.68, 41.48, 66.77, 69.04, 69.15, 79.79, 113.12(2C), 114.41(2C), 127.25, 128.57(2C), 128.88(2C), 129.00(2C), 129.24(2C), 129.79 (2C), 129.83(2C), 130.44(2C), 132.31, 134.18, 144.46, 147.27, 157.82, 174.05.

Example 102

(S)-2-Ethoxy-3-(4-{2-[4-(3,3,3-trifluoro-2-methyl-(R/S)-propylamino)phenyl]ethoxy}phenyl)propanoic Acid 2-(Trifluoromethyl)propionaldehyde (0.0724 g; 0.574 mmole) was dissolved in tetrahydrofurane (3 ml) and sulfuric acid (4 M; 0.041 ml; 0.164 mmole) was added under stirring, followed by addition of 3-{4-[2-(4-aminophenyl)ethoxy]phenyl}-(S)-2-ethoxypropanoic acid hydro chloride (described in Example 56a) (0.2 g; 0.547 mmole) dissolved in tetrahydrofurane (2 ml). The reaction mixture was stirred for 10 minutes, then cooled to 0° C in an ice-bath and sodium borohydride (0.042 g; 1.10 mmole) was added. After addition, the cooling bath was removed. The mixture was stirred overnight and then evaporated to remove tetrahydrofurane. Ethyl acetate and water were added into the residue and the organic phase was separated, washed with brine, dried with magnesium sulfate. The solvent was then evaporated. Chromatography on silica gel(Isolute, SI ) using dichloromethane and then 1% methanol in dichloromethane as eluant gave 0.13 g (40% yield) of (S)-2-ethoxy-3-(4-{2-[4-(3,3,3-trifluoro-2-methyl-(R/S)-propylamino)phenyl]ethoxy}phenyl)propanoic acid.

$^1$H-NMR (500 MHz, CDCl$_3$): δ 1.20 (t, J=7 Hz, 3H), 1.22 (d, J=7 Hz, 3H), 2.51–2.61 (m, 1H), 2.98 (dd, J=14.5, 8 Hz, 1H), 3.01 (t, J=7 Hz, 2H), 3.08 (dd, J=14.5, 4 Hz, 1H), 3.16 (dd, J=14, 7 Hz, 1H), 3.41–3.47 (m, 1H), 3.52 (dd, J=14, 5.5 Hz, 1H), 3.61–3.67 (m, 1H), 4.06 (dd, J=8,4 Hz, 1H), 4.12 (t, J=7 Hz, 2H), 6.61 (d, J=8 Hz, 2H), 6.85 (d, J=8 Hz, 2H), 7.14 (d, J=8 Hz, 2H), 7.18 (d, J=8 Hz, 2H). $^{13}$C-NMR (125 MHz, CDCl$_3$): δ 11.43, 14.98, 34.84, 37.43 (q, J=25 Hz), 37.89, 43.88, 66.70, 68.99, 79.80, 113.11(2C), 114.37(2C), 127.63, 127.85 (q, J=279 Hz), 128.65, 129.93(2C), 130.39 (2C), 145.62, 157.74, 176.24.

Example 103

3-{4-[2-(4-Cyanophenyl)ethoxy]phenyl}-2-ethoxypropanoic Acid Ethyl Ester

3-{4-[2-(4-Cyanophenyl)ethoxy]phenyl}-2-ethoxypropanoic acid ethyl ester was synthesized using the same method as in Example 38(c) using 2-ethoxy-3-(4-hydroxyphenyl) propanoic acid ethyl ester (described in Example 20b) (6.62 g; 27.78 mmole) and p-cyanophenethyl alcohol (2.73 g; 18.52 mmole). The reaction was interrupted after 2 hours. Purification by chromatography on silica gel using first dichloromethane and then petroleum ether:diethyl ether as eluants gave a mixture of product and starting material which was dissolved in ethyl acetate and washed with sodium hydroxide (1 N). The organic phase was washed with water, dried (sodium sulfate), filtered and the solvent as evaporated to give 4.23 g (yield 62%) of 3-{4-[2-(4-cyanophenyl)ethoxy]phenyl}-2-ethoxypropanoic acid ethyl ester.

$^1$H-NMR (400 MHz; CDCl$_3$): δ 1.16 (t, 3H, J=7 Hz), 1.23 (t, 3H, J=7 Hz), 2.93–2.97 (m, 2H), 3.14 (t, 2H, J=6.4 Hz), 3.3–3.4 (m, 1H), 3.56–3.65 (m, 3H), 3.94–3.99 (m, 1H), 4.14–4.26 (m, 4H), 6.8 (dm, 2H, J=8.6 Hz, unresolved), 7.15 (dm, 2H, J=8.6 Hz, unresolved), 7.4 (dm, 2H, J=8.3 Hz, unresolved), 7.60 (dm, 2H, J=8.3 Hz, unresolved). $^{13}$C-NMR (100 MHz; CDCl$_3$): δ 14.1, 15.0, 35.8, 38.4, 60.7, 66.1, 67.5, 80.2, 110.3, 114.2, 118.8, 129.66, 129.74, 130.4, 132.1, 144.2, 157.2, 172.4.

Example 104

3-{4-[2-(4-Cyanophenyl)ethoxy]phenyl}-2-phenylsulfanylpropionic Acid Ethyl Ester 3-(4-Hydroxyphenyl)-2-phenylsulfanylpropanoic acid ethyl ester was reacted with p-cyanophenethyl alcohol using the same method as in Example 38(c) to give 3-{4-[2-(4-cyanophenyl)ethoxy]phenyl}-2-phenylsulfanylpropionic acid ethyl ester.

$^1$H-NMR (600 MHz; CDCl$_3$): δ 1.08 (t, 3H), 2.99 (dd, 1H), 3.1–3.2 (m, 3H), 3.84 (dd, 1H), 3.97–4.07 (m, 2H), 4.16 (t, 2H), 6.77 (dm, 2H, J=8.7 Hz, unresolved), 7.10 (dm, 2H, J=8.4 Hz, unresolved), 7.26–7.31 (m, 3H), 7.39 (dm, 2H, J=8.0 Hz, unresolved), 7.41–7.45 (m, 2H), 7.60 (dm, 2H, J=8.4 Hz, unresolved).

Example 105

3-{4-[2-(4-Cyanophenyl)ethoxy]phenyl}-2-phenylsulfanylpropanoic Acid

3-{4-[2-(4-Cyanophenyl)ethoxy]phenyl}-2-phenylsulfanylpropionic acid ethyl ester (described in Example 104) was hydrolyzed using the same method as in Example 2 to give 3-{4-[2-(4-cyanophenyl)ethoxy]phenyl}-2-phenylsulfanylpropanoic acid.

$^1$H-NMR (500 MHz; CDCl$_3$): δ 2.96–3.2 (m, 1H), 3.07–3.14 (m, 3H), 3.77–3.83 (m, 1H), 4.14 (t, 2H, J=6.5 Hz), 6.78 (dm, 2H, J=8.8 Hz, unresolved), 7.10 (dm, 2H, J=8.8 Hz, unresolved), 7.23–7.28 (m, 3H), 7.35 (dm, 2H, J=8.3 Hz, unresolved), 7.38–7.43 (m, 2H), 7.56 (dm, 2H, J=8.3 Hz, unresolved). $^{13}$C-NMR (125 MHz; CDCl$_3$): δ 35.7, 36.7, 52.1, 67.5, 110.3, 114.5, 118.8, 128.2, 129.0, 129.70, 129.73, 130.1, 132.1, 132.7, 133.0, 144.1, 157.4, 177.3.

Example 106

2-Ethoxy-3-[4-(2-{4-(isopropylaminocarbonyl)phenyl}ethoxy)-phenyl]propanoic acid Ethyl Ester
(a) 4-[2-(4-Formylphenoxy)ethyl]benzonitrile
p-Hydroxybenzaldehyde (24.9 g; 203.8 mmole) was dissolved in dichloromethane (dry). ADDP (47.2 g; 187 mmole) was added followed by addition of triphenylphosphine (49 g; 187 mmole). The reaction mixture was stirred at room temperature for 45 minutes and then p-cyanophenethyl alcohol (25 g; 110 mmole) dissolved in a small amount of dichloromethane (dry) was added in portions during one hour. The reaction mixture was stirred at room temperature over night, filtered and evaporated. Chromatography of the residue on silica gel using ethyl acetate-:heptane as eluant gave 9.7 g (22.7% yield) of 4-[2-(4-formylphenoxy)ethyl]benzonitrile.

$^1$H-NMR (400 MHz; CDCl$_3$): δ 3.21 (t, 2H), 4.30 (t, 2H), 6.99 (d, 2H), 7.42 (d, 2H), 7.63 (d, 2H), 7.84 (d, 2H), 9.89 (s, 1H). $^{13}$C-NMR(100 MHz CDCl$_3$): δ 36.2, 69.4, 110.8, 116.5, 120.4, 131.3, 131.6, 133.33, 133.73, 145.8, 164.8, 192.8.

(b) 4-[2-(4-Formylphenoxy)ethyl]benzoic Acid

4-[2-(4-Formylphenoxy)ethyl]benzonitrile (9.7 g; 38.6 mmole) was refluxed in sulfuric acid (150 ml) and water (150 ml) for 1 hour. Evaporation gave 10 g (100% yield) of 4-[2-(4-formylphenoxy)ethyl]benzoic acid.

$^1$H-NMR (500 MHz; DMSO-d$_6$): d 3.13 (t, 2H), 4.33 (t, 2H), 7.12 (d, 2H), 7.46 (d, 2H), 7.85 (d, 2H), 7.89 (d, 2H), 9.86 (s, 1H).

(c) 4-[2-(4-Formylphenoxy)ethyl]-N-isopropylbenzamide

4-[2-(4-Formylphenoxy)ethyl]benzoic acid (8.11 g; 30 mmole), TBTU (10.6 g; 33 mmole) and DMAP (8.1 g; 66 mmole) were dissolved in DMF (85 ml). The reaction mixture was cooled on an ice bath and isopropylamine (12 g; 200 mmole) dissolved in DME (100 ml) was added. The reaction mixture was stirred at room temperature over night. A large amount of water was added and the mixture was extracted with ethyl acetate. The organic phase was washed with potassium hydogen sulfate (0.3 M), water and brine and dried with sodium sulfate. Evaporation gave 8 g (85.6% yield) of 4-[2-(4-formylphenoxy)ethyl]-N-isopropylbenzamide.

$^1$H-NMR (600 MHz; DMSO-d$_6$): δ 1.13 (d, 6H), 3.06 (t, 2H), 3.45 (m, 1H), 4.22 (t, 2H), 6.94 (d, 2H), 7.36 (d, 2H), 7.61 (d, 2H), 7.77 (d, 2H), 8.11 (d, 1H), 8.22 (s, 1H).

(d) 2-Ethoxy-3-[4-(2-{4-(isopropylaminocarbonyl)phenyl}ethoxy)phenyl]acrylic acid Ethyl Ester 4-[2-(4-Formylphenoxy)ethyl]-N-isopropylbenzamide (2 g; 6.42 mmole) and (1,2-diethoxy-2-oxoethyl) (trphenyl) phosphonium chloride (3 g; 7 mmole) were dissolved in chloroform. The reaction mixture was cooled on an ice bath. Tetramethylguanidine (1 g; 8.7 mmole) was added in portions. The reaction mixture was stirred over the weekend then the solvent was evaporated. The residue was dissolved in ethyl acetate and the precipitating, triphenylphosphine oxide was filtered off. The filtrate was evaporated. Crystals were obtained by freezing an ethanol/water solution of the residue. The crystals were filtered off and washed with a very cold mixture of ethanol/water and 1.2 g (44.1% yield) of 2-ethoxy-3-[4-(2-{4-(isopropylaminocarbonyl)phenyl}ethoxy)phenyl]acrylic acid ethyl ester was obtained.

$^1$H-NMR (400 MHz; CDCl$_3$): δ 1.27 (d, 6H), 1.37 (t, 6H), 3.15 (t, 2H), 3.98 (q, 2H), 4.22 (t, 2H), 4.29 (m, 3H), 5.93 (bs, 1H), 6.88 (d, 2H), 6.96 (s, 1H), 7.35 (d, 2H), 7.69–7.76 (m, 4H). $^{13}$C-NMR (100.6 MHz CDCl$_3$): δ 15.4, 16.6, 24.0, 36.6, 42.9, 62.1, 68.6, 69.2, 115.6, 125.0, 127.7, 128.1, 130.2, 132.8, 134.4, 142.9, 144.2, 160.2, 166.0, 167.5.

(e) 2-Ethoxy-3-[4-(2-{4-(isopropylaminocarbonyl)phenyl}ethoxy)phenyl]propanoic Acid Ethyl Ester 2-Ethoxy-3-[4-(2-{4-(isopropylaminocarbonyl)phenyl}ethoxy)phenyl]acrylic acid ethyl ester was hydrogenated using the same method as in Example 1(d) to give 2-ethoxy-3-[4-(2-{4-(isopropylaminocarbonyl)phenyl}ethoxy)phenyl]propanoic acid ethyl ester.

$^1$H-NMR (400 MHz; CDCl$_3$): δ 1.17 (t, 3H), 1.21–1.28 (m, 9H), 2.95 (d, 2H), 3.12 (t, 2H), 3.31–3.39 (m, 1H), 3.56–3.64 (m, 1H), 3.96 (t, 1H), 4.13–4.20 (m, 4H), 4.26–4.32 (m, 1H), 5.95 (bs, 1H), 6.8 (d, 2H), 7.14 (d, 2H), 7.33 (d, 2H), 7.71 (d, 2H). $^{13}$C-NMR (100 MHz; CDCl$_3$): δ 15.3, 16.1, 24.0, 36.7, 39.6, 42.9, 61.8, 67.3, 69,2, 81.5, 115.4, 128.1, 130.2, 130.6, 131.5, 134.3, 143.1, 158.5, 167.6, 173.6.

Example 107

2-Ethoxy-3-[4-(2-{4-(isopropylaminocarbonyl) phenyl}-ethoxy)phenyl]propanoic Acid 2-Ethoxy-3-[4-(2-{4-(isopropylaminocarbonyl)phenyl}ethoxy)phenyl]propanoic acid ethyl ester (described in Example 106) (1 g; 2.34 mmole) was dissolved in tetrahydrofuran (10 ml). Lithium hydroxide (0.056 g; 2.34 mmole) dissolved in water (6 ml) was added slowly in portions during 20 minutes. The reaction mixture was stirred at room temperature for 3 hours and then diluted with water followed by careful evaporation of tetrahydrofuran. The residual water phase was extracted once with diethyl ether, then acidified and extracted with ethyl acetate. The ethyl acetate phase was washed with brine, dried with sodium sulfate and evaporated. The residue was dissolved in methanol (10 ml) and sodium hydroxide (0.109 g; 1.73 mmole) in water (3.5 ml) was added. The solution was evaporated and the residue redissolved in water. Freeze drying gave 0.643 g (65.2% yield) of 2-ethoxy-3-[4-(2-{4-(isopropylaminocarbonyl)phenyl}ethoxy)phenyl]propanoic acid.

$^1$H-NMR (400 MHz; $D_2O$): δ 1.04 (t, 3H), 1.2 (d, 6H), 2.73–2.81 (m, 1H), 2.88–2.97 (m, 3H), 3.22–3.31 (m, 1H), 3.45–3.55 (m, 1H), 3.86–3.92 (m, 1H), 4.09 (m, 3H), 6.77 (d, 2H), 7.6 (d, 2H), 7.24 (d, 2H), 7.58 (d, 2H). $^{13}$C-NMR (100 MHz; $D_2O$): δ 15.3, 22.6, 33.8, 39.3, 43.4, 66.7, 69.6, 83.6, 115.9, 128.3, 130.2, 131.4, 132.3, 133.2, 143.9, 170.5, 181.4

Example 108

(S)-2-ethoxy-3-(4-{2-[4-({[2-(methylsulfanyl) anilino]carbothioyl}amino)-phenyl]ethoxy}phenyl) propanoic acid 3-{4-[2-(4-Aminophenyl)ethoxy]phenyl}-(S)-2-ethoxypropanoic acid hydro chloride (described in Example 56a) (0.2 g; 0.547 mmole) was dissolved in tetrahydrofurane (5 ml). Sodium hydrogencarbonate (0.053 g; 0.631 mmole) was added and the mixture was stirred for a little while. 2-(Methylthio)phenyl isocyanate (0.108 g; 0.596 mmole) was then added. The reaction mixture was stirred overnight and then evaporated to dryness. Chromatography of the residue on silica gel using dichloromethane and then methanol in dichloromethane (2%, 4%, 10% and 20%) as eluant gave 0.21 g (75% yield) of 2-(S)-2-ethoxy-3-(4-{2-[4-({[2-(methylsulfanyl)anilino]carbothioyl}amino)phenyl]ethoxy}-phenyl)propanoic acid.

$^1$H-NMR (600 MHz; DMSO-$d_6$): δ 0.96 (t, J=7 Hz, 3H), 2.35 (s, 3H), 2.70 (dd, J=14, 8 Hz, 1H), 2.81 (dd, J=14, 5 Hz, 1H), 2.93 (t, J=6.6 Hz, 2H), 3.18–3.23 (m, 1H), 3.42–3.47 (m, 1H), 3.82 (dd, J=8, 5 Hz, 1H), 4.08 (t, J=6.6 Hz, 2H), 6.76 (d, J=8.7 Hz, 2H), 7.06 (d, J=8.4 Hz, 2H), 7.12 (dd, J=7.7, 7.4 Hz, 1H), 7.19–7.26 (m, 4H), 7.31 (d, J=7.7 Hz, 1H), 7.39 (d, J=8.4 Hz, 2H), 9.21 (s, 1H) and 9.84 (s, 1H). $^{13}$C-NMR (150 MHz, DMSO-$d_6$): δ 15.29, 15.49, 34.88, 38.11, 65.22, 68.46, 80.25, 114.52(2C), 124.37(2C), 125.42, 126.67, 127.57, 129.14, 129.46(2C), 130.28, 130.70(2C), 135.44, 136.47, 136.89, 137.90, 157.34, 174.45, 180.86.

Example 109

2-Isopropoxy-3-[4-({4-[(methylsulfonyl)oxy] phenethyl}-oxy)phenyl]propanoic Acid (a) Benzyl 2-Isopropoxyacetate Benzyl 2-isopropoxyacetate was synthesized using the same method as in Example 58a from isopropoxyacetic acid.

$^1$H-NMR(500 MHz; CDCl$_3$): δ 1.23 (d, J=6 Hz, 6H), 3.68–3.75 (m, 1H), 4.15 (s, 2H), 5.23 (s, 2H), 7.36–7.41 (m, 5H).

(b) Benzyl 3-[4-(Benzyloxy)phenyl]-2-isopropoxy-2-propenoate

Benzyl 3-[4-(benzyloxy)phenyl]-2-isopropoxy-2-propenoate was synthesized from benzyl 2-isopropoxyacetate using the same method as in Example 58b.

$^1$H-NMR of E and Z isomer mixture(400 MHz; CDCl$_3$): d 1.31 (d, J=6 Hz, 6H of one isomer), 1.32 (d, J=6 Hz, 6H of one isomer), 4.45–4.53 (m, 1H), 5.10 (s, 2H), 5.31 (s, 2H of one isomer), 5.32 (s, 2H of one isomer), 6.98–7.01 (m, 2H), 7.07 (s, 1H of one isomer), 7.08 (s, 1H of one isomer), 7.35–7.47 (m, 10H), 7.81–7.85 (m, 2H). $^{13}$C-NMR(100 MHz; CDCl$_3$): δ 22.41(2C), 66.60, 69.85, 74.31, 114.53 (2C), 124.64, 126.79, 127.38(2C), 127.94, 128.10(2C), 128.15, 128.50(4C), 131.84(2C), 135.89, 136.62, 141.64, 159.08, 164.81.

(c) 3-(4-Hydroxyphenyl)-2-isopropoxypropanoic Acid 3-(4-Hydroxyphenyl)-2-isopropoxypropanoic acid was synthesized from benzyl 3-[4-(benzyloxy)phenyl]-2-isopropoxy-2-propenoate using the same method as in Example 58c.

$^1$H-NMR(500 MHz; CDCl$_3$): δ 1.08 (d, J=6 Hz, 3H), 1.21 (d, J=6 Hz, 3H), 2.93 (dd, J=14, 8 Hz, 1H), 3.10 (dd, J=14, 4 Hz, 1H), 3.56–3.63 (m, 1H), 4.14 (dd, J=8, 4 Hz, 1H), 6.80 (d, J=8.3 Hz, 2H), 7.15 (d, J=8.3 Hz, 2H).

(d) 3-(4-Hydroxyphenyl)-2-isopropoxypropanoic Acid methyl Ester

Methyl 3-(4-hydroxyphenyl)-2-isopropoxypropanoate was synthesized using the same method as in Example 58d from 3-(4-hydroxyphenyl)-2-isopropoxypropanoic acid.

$^1$H-NMR(500 MHz; CDCl$_3$): δ 1.00 (d, J=6 Hz, 3H), 1.18 (d, J=6 Hz, 3H), 2.90 (dd, J=14, 8.5 Hz, 1H), 2.98 (dd, J=14, 5 Hz, 1H), 3.50–3.57 (m, 1H), 3.74 (s, 3H), 4.07 (dd, J=8.5, 5 Hz, 1H), 6.78 (d, J=8.3 Hz, 2H) and 7.13(d, J=8.3 Hz).

(e) 2-Isopropoxy-3-[4-(2-{4-methylsulfonyloxy-phenyl}ethoxy)phenyl]propanoic Acid Ethyl Ester 2-Isopropoxy-3-[4-(2-{4-methylsulfonyloxy-phenyl}ethoxy)phenyl]propanoic acid methyl ester was synthesized from 3-(4-hydroxyphenyl)-2-isopropoxypropanoic acid methyl ester and 2-(4-methanesulfonyloxyphenyl) ethylmethanesulfonate (described in Example 1b) using the same method as in Example 58e.

$^1$H-NMR(500 MHz; CDCl$_3$): d 0.99 (d, J=6 Hz, 3H), 1.17 (t, J=6 Hz, 3H), 2.90 (dd, J=13.8, 8.6 Hz, 1H), 2.97 (dd, J=13.8, 5 Hz, 1H), 3.12 (t, J=7 Hz, 2H), 3.15 (s, 3H), 3.50–3.55 (m, 1H), 3.73 (s, 3H), 4.05 (dd, J=8.6, 5 Hz, 1H), 4.17 (t, J=7 Hz, 2H), 6.83 (d, J=8.6 Hz, 2H), 7.17 (d, J=8.6 Hz, 2H), 7.25 (d, J=8.6 Hz, 2H), 7.36 (d, J=8.6 Hz, 2H). $^{13}$C-NMR(100 MHz; CDCl$_3$): d 21.40, 22.49, 35.10, 37.23, 38.82, 51.80, 68.13, 72.39, 78.33, 114.20(2C), 121.90(2C), 129.62, 130.43(2C), 130.51(2C), 137.92, 147.80, 157.32, 173.48.

(f) 2-Isopropoxy-3-[4-(2-{4-methylsulfonyloxy-phenyl}ethoxy)phenyl]propanoic Acid 2-Isopropoxy-3-[4-(2-{4-methylsulfonyloxy-phenyl}ethoxy)phenyl]propanoic acid methyl ester (0.1 g; 0.229 mmole) was dissolved in tetrahydrofuran(2 ml). Lithium hydroxide (0.006 g; 0.25 mmole) in water (2 ml) was added. The reaction mixture was stirred at room temperature for 8 hours. Tetrahydrofuran was evaporated. The remaining water solution was extracted with diethyl ether. The water solution was then acidified with hydorchloric acid (1%) to pH~2 and extracted twice with ethyl acetate. The organic phases were combined and dried with magnesium sulfate. The solvent was evaporated and 0.085 g (88% yield) of 2-isopropoxy-3-[4-(2-{4-methylsulfonyloxy-phenyl}ethoxy)phenyl]propanoic acid was obtained.

$^1$H-NMR(400 MHz; CDCl$_3$): δ 0.99 (d, J=6 Hz, 3H), 1.15 (d, J=6 Hz, 3H), 2.88 (dd, J=13.6, 8.3 Hz, 1H), 3.01–3.11 (m, 3H), 3.11 (s, 3H), 3.49–3.58 (m, 1H), 4.07 (dd, J=8.3, 3.9 Hz, 1H), 4.13 (t, J=6.8 Hz, 2H), 6.80 (d, J=8.3 Hz, 2H), 7.14 (d, J=8.8 Hz, 2H), 7.21 (d, J=8.8 Hz, 2H) and 7.32 (d, J=8.3 Hz, 2H). $^{13}$C-NMR(100 MHz; CDCl$_3$): δ 21.68, 22.16, 35.07, 37.21, 38.29, 68.12, 73.12, 77.73, 114.28(2C), 121.89 (2C), 129.02, 130.49(2C), 130.57(2C), 137.89, 147.79, 157.47 and 175.89.

Biological Activity

The biological activity of the compounds of the invention was tested in obese diabetic mice of the Umeå ob/ob strain. Groups of mice received the test compound by gavage once daily for 7 days. On the last day of the experiment the animals were anesthetized 2 h after dose in a non-fed state and blood was collected from an incised artery. Plasma was analyzed for concentration of glucose, insulin and triglycerides. A group of untreated obese diabetic mice of the same age served as control. The weight of the mice was measured before and after the experiment and the obtained weight gain was compared to the weight gain of the control animals. The individual values for glucose, insulin and triglyceride levels of the mice from the test group were expressed as the percent range of the corresponding values from the control group.

The desired "therapeutic effect" was calculated as the average percent reduction of the three variables glucose, insulin and triglycerides below the levels in the control animals. The therapeutic effect of the tested compounds according to the invention was compared to the same effect in the prior art compound troglitazone, administrered by gavage in the oral dose of 100 μmol/kg for 7 days.

The superior effects of the tested compounds according to the invention compared to that of troglitazone when given in the same oral dose demonstrate the increased potency and efficacy of the claimed compounds.

| Abbreviations | |
|---|---|
| NIDDM | non insulin dependent diabetes mellitus |
| IRS | insulin resistance syndrom |
| VLDL | very low density lipoproteins |
| HDL | high density lipoproteins |
| PPAR | peroxisome proliferator activated receptor |
| LDA | lithium diisopropylamide |
| LHMDS | lithium hexamethyldisilylamine |
| DMF | dimethylformamide |
| DEAD | diethyl azodicarboxylate |
| ADDP | azodicarbonyl dipiperidine |
| EDC | 1-(3-dimethylaminopropyl)-3-ethylcarbodiimide |
| DCC | dicyclohexylcarbodiimide |
| HBTU | O-benzotriazol-1-yl-N,N,N',N'-tetramethyluronium hexafluorophosphate |
| TBTU | O-benzotriazol-1-yl-N,N,N',N'-tetramethyluronium tetrafluoroborate |
| PyBop | benzotriazole-1-yl-oxy-tris-pyrolidino-phosphonium hexafluorophosphate |
| TEA | triethylamine |
| DiPEA | diisopropylethylamine |
| TLC | thin layer chromatography |
| THF | tetrahydrofuran |
| Pd/C | palladium on charcoal |
| HOBtxH$_2$O | 1-hydroxybenzotriazole-hydrate |
| t | triplet |

| Abbreviations | |
|---|---|
| s | singlet |
| d | doublet |
| q | quartet |
| qvint | quintet |
| m | multiplet |
| br | broad |
| DMSO | dimethyl sulfoxide |
| DIBAL | diisobutylaluminium hydride |

What is claimed is:

1. A compound of the formula

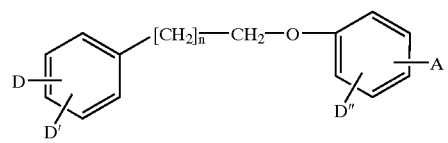

or a strereoisomer, optical isomer or racemate thereof or a pharmaceutically acceptable form of any of the above selected from the group consisting of a salts, a solvate, a crystalline form and any combination thereof, in which formula A is situated in the ortho, meta or para position and represents

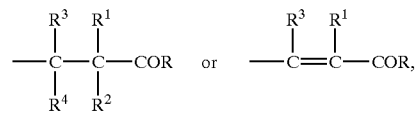

wherein

R is hydrogen;
—OR$^a$, wherein R$^a$ represents hydrogen, alkyl, aryl or alkylaryl;
—NR$^a$R$^b$, wherein R$^a$ and R$^b$ are the same or different and R$^a$ is as defined above and R$^b$ represents hydrogen, alkyl, aryl, alkylaryl, cyano, —OH, —Oalkyl, —Oaryl, —Oalkylaryl, —COR$^c$ or —SO$_2$R$^d$, wherein R$^c$ represents hydrogen, alkyl, aryl or alkylaryl and R$^d$ represents alkyl, aryl or alkylaryl;

R$^1$ is alkyl, aryl, alkenyl, alkynyl, cyano;
—OR$^e$, wherein R$^e$ is alkyl, acyl, aryl or alkylaryl;
—O—[CH$_2$]$_m$—OR$^f$, wherein R$^f$ represents hydrogen, alkyl, acyl, aryl or alkylaryl and m represents an integer 1–8;
—OCONR$^a$R$^c$, wherein R$^a$ and R$^c$ are as defined above;
—SR$^d$, wherein R$^d$ is as defined above;
—SO$_2$NR$^a$R$^f$, wherein R$^f$ and R$^a$ are as defined above;
—SO$_2$OR$^a$, wherein R$^a$ is as defined above;
—COOR$^d$, wherein R$^d$ is as defined above;

R$^2$ is hydrogen, halogen, alkyl, aryl, or alkylaryl,
R$^3$ and R$^4$ are the same or different and each represents hydrogen, alkyl, aryl, or alkylaryl,
n is an integer 1–6,
D is situated in the ortho, meta or para position and represents
—OSO$_2$R$^d$, wherein R$^d$ is as defined above;
—OCONR$^f$R$^a$, wherein R$^f$ and R$^a$ are as defined above;
—NR$^c$COOR$^d$, wherein R$^c$ and R$^d$ are as defined above;

—NR$^c$COR$^a$, wherein R$^c$ and R$^a$ are as defined above;
—NR$^c$R$^d$, wherein R$^c$ and R$^d$ are as defined above;
—NR$^c$SO$_2$R$^d$, wherein R$^c$ and R$^d$ are as defined above;
—NR$^c$CONR$^a$R$^k$, wherein R$^a$, R$^c$ and R$^k$ are the same or different and each represents hydrogen, alkyl, aryl, or alkylaryl;
—NR$^c$CSNR$^a$R$^k$, wherein R$^a$, R$^c$ and R$^k$ are the same or different and each represents hydrogen, alkyl, aryl or alkylaryl;
—SO$_2$R$^d$, wherein R$^d$ is as defined above;
—SOR$^d$, wherein R$^d$ is as defined above;
—SR$^c$, wherein R$^c$ is as defined above;
—SO$_2$NR$^a$R$^f$, wherein R$^f$ and R$^a$ are as defined above;
—SO$_2$OR$^a$, wherein R$^a$ is as defined above;
—CN,
—CONR$^c$R$^a$, wherein R$^c$ and R$^a$ are as defined above;
D' is situated in the ortho, meta or para position and represents hydrogen, alkyl, acyl, aryl, alkylaryl, halogen, —CN, —NO$_2$, —NR$^f$R$^b$, wherein R$^f$ and R$^b$ are as defined above;
—OR$^f$, wherein R$^f$ is as defined above;
—OSO$_2$R$^d$, wherein R$^d$ is as defined above;
D" is situated in the ortho, meta or para position and represents hydrogen, alkyl, acyl, aryl, alkylaryl, halogen, —CN, —NO$_2$, —NR$^f$R$^b$ wherein R$^f$ and R$^b$ are as defined above;
—OR$^f$, wherein R$^f$ is as defined above; or
—OSO$_2$R$^d$, wherein R$^d$ is as defined above,
with the exception of (S)-2-ethoxy-3-[4-(2-{4-methanesulfonyloxyphenyl}ethoxy)phenyl]propanoic acid, and
3-{4-[2-(4-tert-butoxycarbonylaminophenyl)ethoxy]phenyl}-(S)-2-ethoxypropanoic acid.

2. A compound according to claim 1, wherein
A is situated in the meta or para position and represents,

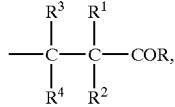

wherein
R is hydrogen;
—OR$^a$;
—NR$^a$R$^b$, wherein R$^a$ and R$^b$ are the same or different and R$^b$ represents hydrogen, alkyl, aryl, alkylaryl, cyano, —OH, —Oalkyl or —Oalkylaryl;
R$^1$ is cyano;
—OR$^d$;
—O[CH$_2$]$_m$—OR$^a$;
R$^2$ is hydrogen or alkyl;
R$^3$ is hydrogen or alkyl;
R$^4$ is hydrogen;
n is an integer 1–3;
D is situated in the ortho, meta or para position and represents —OSO$_2$R$^d$;
—OCONR$^a$R$^c$;
—NR$^c$COOR$^d$;
—NR$^c$COR$^a$;
—NR$^c$R$^d$;
—NR$^c$SO$_2$R$^d$;
—NR$^c$CONR$^a$R$^k$;
—NR$^c$CSNR$^a$R$^k$;
—SO$_2$R$^d$;
—SR$^c$;
—CN;
—CONR$^a$R$^c$;
D' is situated in the ortho, meta or para position and represents hydrogen, alkyl, alkylaryl, halogen, —CN or —NO$_2$;
—OR$^h$, wherein R$^h$ is hydrogen or alkyl; and
D" is situated in the ortho, meta or para position and represents hydrogen, alkyl, alkylaryl, halogen, —CN or —NO$_2$;
—OR$^h$, wherein R$^h$ is as defined above.

3. A compound according to claim 2, wherein
A is situated in the meta or para position;
R is —OR$^a$, wherein R$^a$ is hydrogen, alkyl or alkylaryl;
—NHR$^b$, wherein R$^b$ is hydrogen, alkyl, alkylaryl, cyano, —Oalkyl or —Oalkylaryl;
R$^1$ is —Oalkyl;
R$^2$ is hydrogen or alkyl;
R$^3$ is hydrogen or alkyl;
R$^4$ is hydrogen;
n is an integer 1–3,
D is situated in the ortho, meta or para position and represents
—NR$^c$COOR$^d$; and
D' is hydrogen; and
D" is hydrogen.

4. A compound according to claim 3, wherein
A is situated in the para position;
R is —OH, Oalkyl or —Oalkylaryl;
—NH$_2$, —NHOalkylaryl or —NHCN;
R$^2$ is hydrogen;
R$^3$ is hydrogen;
n is the integer 1; and
D is situated in the para position, and represents —NR$^h$COOR$^d$.

5. A compound according to claim 4, wherein
D is —NR$^j$COOalkyl, wherein R$^j$ represents hydrogen or lower alkyl.

6. A compound according to claim 2, wherein
A is situated in the meta or para position;
R is —OR$^a$, wherein R$^a$ is hydrogen, alkyl or alkylaryl;
—NHR$^b$, wherein R$^b$ is hydrogen, alkyl, alkylaryl, cyano, —Oalkyl or —Oalkylaryl;
R$^1$ is —Oalkyl;
R$^2$ is hydrogen or alkyl;
R$^3$ is hydrogen or alkyl;
R$^4$ is hydrogen;
n is an integer 1–3;
D is situated in the ortho, meta or para position and represents
—NR$^c$COR$^a$, wherein R$^a$ is hydrogen, alkyl, aryl or alkylaryl;
D' is hydrogen; and
D" is hydrogen.

7. A compound according to claim 6, wherein
A is situated in the para position;
R is —OH, —Oalkyl or —Oalkylaryl;
—NH$_2$, —NHOalkylaryl or —NHCN;
R$^2$ is hydrogen;
R$^3$ is hydrogen;
n is the integer 1; and
D is situated in the para position, and represents —NR$^h$COR$^d$.

8. A compound according to claim 7, wherein
D is —NHCOR$^d$.

9. A compound according to claim 2, wherein
A is situated in the meta or para position,
R is —OR$^a$, wherein R$^a$ is hydrogen, alkyl or alkylaryl;
—NHR$^b$, wherein R$^b$ is hydrogen, alkyl, alkylaryl, cyano, —Oalkyl or —Oalkylaryl;
R$^1$ is —Oalkyl,
R$^2$ is hydrogen;
R$^3$ is hydrogen or alkyl;
R$^4$ is hydrogen;
n is an integer 1–3;
D is situated in the ortho, meta or para position and represents —SO$_2$R$^d$;
D' is hydrogen; and
D" is hydrogen.

10. A compound according to claim 9, wherein
A is situated in the para position;
R is —OH, —Oalkyl or Oalkylaryl;
—NH$_2$, —NHOalkylaryl or —NHCN;
R$^3$ is hydrogen;
n is the integer 1; and
D is situated in the para position and represents —SO$_2$R$^d$.

11. A compound according to claim 2, wherein
A is situated in the meta or para position,
R is —OR$^a$, wherein R$^a$ is hydrogen, alkyl or alkylaryl;
—NHR$^b$, wherein R$^b$ is hydrogen, alkyl, alkylaryl, cyano, —Oalkyl or —Oalkylaryl;
R$^1$ is —Oalkyl;
R$^2$ is hydrogen;
R$^3$ is hydrogen or alkyl,
R$^4$ is hydrogen;
n is an integer 1–3,
D is situated in the ortho, meta or para position and represents
—SR$^d$;
D' is hydrogen; and
D" is hydrogen.

12. A compound according to claim 11, wherein
A is situated in the para postion;
R is —OH, —Oalkyl or —Oalkylaryl;
—NH$_2$, —NHOalkylaryl or —NHCN;
R$^3$ is hydrogen;
n is the integer 1; and
D is situated in the para position and represents —SR$^d$.

13. A compound according to claim 2, wherein
A is situated in the meta or para position,
R is —OR$^a$, wherein R$^a$ is hydrogen, alkyl or alkylaryl;
—NHR$^b$, wherein R$^b$ is hydrogen, alkyl, alkylaryl, cyano, —Oalkyl or —Oalkylaryl;
R$^1$ is —Oalkyl;
R is hydrogen or alkyl;
R$^3$ is hydrogen or alkyl;
R$^4$ is hydrogen;
n is an integer 1–3,
D is situated in the ortho, meta or para position and represents —OCONR$^a$R$^c$;
D' is hydrogen; and
D" is hydrogen.

14. A compound according to claim 13, wherein
A is situated in the para position;
R is —OH, —Oalkyl or —Oalkylaryl;
—NH$_2$, —NHOalkylaryl, —NHCN;
R$^2$ is hydrogen;
R$^3$ is hydrogen;
n is the integer 1; and
D is situated in the para position, and represents —OCONHR$^d$.

15. A compound according to claim 14, wherein
D is —OCONHalkyl.

16. A compound according to claim 2, wherein
A is situated in the meta or para position,
R is —OR$^a$, wherein R$^a$ is hydrogen, alkyl or alkylaryl;
—NHR$^b$, wherein R$^b$ is hydrogen, alkyl, alkylaryl, cyano, —Oalkyl or —Oalkylaryl;
R$^1$ is —Oalkyl,
R$^2$ is hydrogen or alkyl;
R$^3$ is hydrogen or alkyl,
R$^4$ is hydrogen;
n is an integer 1–3;
D is situated in the ortho, meta or para position and represents
—NR$^c$SO$_2$R$^d$;
D' is hydrogen; and
D" is hydrogen.

17. A compound according to claim 16, wherein
A is situated in the para position;
R is —OH, —Oalkyl or —Oalkylaryl;
—NH$_2$, —NHOalkylaryl or —NHCN;
R$^2$ is hydrogen;
R$^3$ is hydrogen;
n is the integer 1; and
D is situated in the para position, and represents —NR$^h$SO$_2$R$^d$.

18. A compound according to claim 17, wherein
D is —NR$^h$SO$_2$alkyl.

19. A compound according to claim 2, wherein
A is situated in the meta or para position,
R is —OR$^a$, wherein R$^a$ is hydrogen, alkyl or alkylaryl;
—NHR$^b$, wherein R$^b$ is hydrogen, alkyl, alkylaryl, cyano, —Oalkyl or —Oalkylaryl;
R$^1$ is —Oalkyl;
R$^2$ is hydrogen or alkyl;
R$^3$ is hydrogen or alkyl,
R$^4$ is hydrogen;
n is an integer 1–3;
D is situated in the ortho, meta or para position and represents —NR$^c$R$^d$;
D' is hydrogen; and
D" is hydrogen.

20. A compound according to claim 19, wherein
A is situated in the para position;
R is —OH, —Oalkyl or —Oalkylaryl;
—NH$_2$, —NHOalkylaryl or —NHCN;
R$^2$ is hydrogen;
R$^3$ is hydrogen;
n is the integer 1; and
D is situated in the para position, and represents —NR$^h$R$^d$.

21. A compound according to claim 20, wherein

D is —NR$^h$ alkyl.

22. A compound according to claim 2, wherein

A is situated in the meta or para position,

R is —OR$^a$, wherein R$^a$ is hydrogen, alkyl or alkylaryl;
—NHR$^b$, wherein R$^b$ is hydrogen, alkyl, alkylaryl, cyano, —Oalkyl or —Oalkylaryl;

R$^1$ is —Oalkyl;

R$^2$ is hydrogen or alkyl;

R$^3$ is hydrogen or alkyl,

R$^4$ is hydrogen;

n is an integer 1–3;

D is situated in the ortho, meta or para position and represents
—NR$^c$CONR$^a$R$^k$, wherein R$^a$ is hydrogen, alkyl, aryl or alkylaryl;

D' is hydrogen; and

D" is hydrogen.

23. A compound according to claim 22, wherein

A is situated in the para position;

R is —OH, —Oalkyl or —Oalkylaryl;
—NH$_2$, —NHOalkylaryl or —NHCN;

R$^2$ is hydrogen;

R$^3$ is hydrogen;

n is the integer 1; and

D is situated in the para position, and represents —NHCONHR$^d$.

24. A compound according to claim 23, wherein

D is —NHCONHalkyl.

25. A compound according to claim 2, wherein

A is situated in the meta or para position,

R is —OR$^a$, wherein R$^a$ is hydrogen, alkyl or alkylaryl;
—NHR$^b$, wherein R$^b$ is hydrogen, alkyl, alkylaryl, cyano, —Oalkyl or —Oalkylaryl;

R$^1$ is —Oalkyl;

R$^2$ is hydrogen or alkyl;

R$^3$ is hydrogen or alkyl;

R$^4$ is hydrogen;

n is an integer 1–3;

D is situated in the ortho, meta or para position and represents
—NR$^c$CSNR$^a$R$^k$, wherein R$^a$ is hydrogen, alkyl, aryl or alkylaryl;

D' is hydrogen; and

D" is hydrogen.

26. A compound according to claim 25, wherein

A is situated in the para position;

R is —OH, —Oalkyl or —Oalkylaryl;
—NH$_2$, —NHOalkylaryl or —NHCN;

R$^2$ is hydrogen;

R$^3$ is hydrogen;

n is the integer 1; and

D is situated in the para position, and represents —NHCSNHR$^d$.

27. A compound according to claim 26, wherein

R$^1$ is —Olower alkyl; and

D is —NHCSNHalkyl.

28. A compound according to claim 2, wherein

A is situated in the meta or para position,

R is —OR$^a$, wherein R$^a$ is hydrogen, alkyl or alkylaryl;
—NHR$^b$, wherein R$^b$ is hydrogen, alkyl, alkylaryl, cyano, —Oalkyl or —Oalkylaryl;

R$^1$ is —Oalkyl;

R$^2$ is hydrogen or alkyl;

R$^3$ is hydrogen or alkyl;

R$^4$ is hydrogen;

n is an integer 1–3,

D is situated in the ortho, meta or para position and represents —OSO$_2$R$^d$;

D' is hydrogen; and

D" is hydrogen.

29. A compound according to claim 28, wherein

A is situated in the para position,

R is —OH, —Oalkyl or —Oalkylaryl;
—NH$_2$, —NHOalkylaryl or —NHCN;

R$^2$ is hydrogen;

R$^3$ is hydrogen;

n is the integer 1; and

D is situated in the para position and represents —OSO$_2$alkyl or —OSO$_2$alkylaryl.

30. A compound according to claim 29, wherein

D is —OSO$_2$ alkyl.

31. A compound according to claim 1 selected from

2-Ethoxy-3-[4-(2-{4-methanesulfonyloxyphenyl}ethoxy)phenyl]propanoic acid;

3-{4-[2-(4-tert-Butoxycarbonylaminophenyl)ethoxy]phenyl}-2-ethoxypropanoic acid;

2-Ethoxy-3-{4-[2-(4-methanesulfonylphenyl)ethoxy]phenyl}propanoic acid;

2-Ethoxy-3-{4-[2-(4-methylsulfanylphenyl)ethoxy]phenyl}propanoic acid;

2-Ethoxy-3-[4-(2-{4-isobutyrylaminophenyl}ethoxy)phenyl]propanoic acid;

3-{4-[2-(4-tert-Butylcarbamoyloxyphenyl)ethoxy]phenyl}-2-ethoxypropanoic acid ethyl ester;

2-Ethoxy-3-{4-[2-(4-methanesulfonylaminophenyl)ethoxy]phenyl}propanoic acid;

N-Cyano-2-ethoxy-3-[4-(2-{4-methanesulfonyloxyphenyl}ethoxy)phenyl]propanoic amide;

N-Benzyloxy-2-ethoxy-3-[4-(2-{4-methanesulfonyloxyphenyl}ethoxy)phenyl]propanoic amide;

2-Ethoxy-3-[4-(2-{4-methanesulfonyloxyphenyl}ethoxy)phenyl]propanoic amide;

2-Ethoxy-3-{4-[3-(3-methanesulfonyloxyphenyl)propoxy]phenyl}propanoic acid ethyl ester;

2-Ethoxy-3-(4-{2-[4-(2-propanesulfonyloxy)phenyl]ethoxy}phenyl)propanoic acid;

3-[4-{2-(4-[tert-Butoxycarbonyl(methyl)amino]phenyl)ethoxy}phenyl]-(S)-2-ethoxypropanoic acid;

(S)-2-Ethoxy-3-[4-{2-[4-(methoxycarbonylamino)phenyl)ethoxy]pheyl}propanoic acid;

2-Ethoxy-3-{4-[2-(4-methylcarbamoyloxyphenyl)ethoxy]phenyl}propanoic acid ethyl ester;

3-[4-{2-(4-[Benzyloxycarbonylamino]phenyl)ethoxy}phenyl]-(S)-2-ethoxypropanoic acid;

3-{4-(2-(4-tert-Butoxycarbonylaminophenyl)ethoxy]-3-methoxyphenyl}-2-ethoxypropanoic acid;

3-[4-(2-{4-tert-Butoxycarbonylaminophenyl}ethoxy)phenyl]-2-(2,2,2-trifluoroethoxy)propanoic acid methyl ester; or (S)-2-Ethoxy-3-(4-{2-[4-(phenylsulfonyl)phenyl]ethoxy}phenyl)propanoic acid;

or, where applicable, a stereoisomer, optical isomer or racemate thereof or a pharmaceutically acceptable form of any of the above selected from the group consisting of a salt, a solvate, a crystalline form and any combination thereof.

32. A compound according to any one of claims 1, 30 and 31 wherein the compound is one of the possible enantiomers.

33. A process for preparing a compound according to claim 1, which comprises a) condensing a compound of the formula II

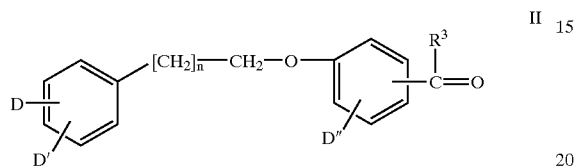

II with a compound of the formula III or IV

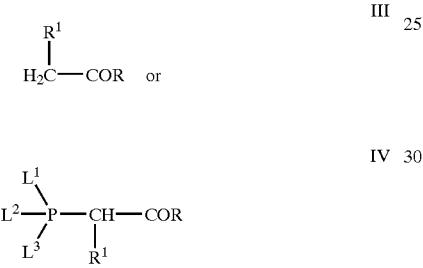

III

IV in which formulas D, D', D", n, R, $R^1$ and $R^3$ are as defined in claim 1 and $L^1=L^2=L^3$ are phenyl or $L^1=L^2$ are $OR^d$ (wherein $R^d$ is as defined in claim 1) and $L^3$ is =O, whereafter, if desired, reducing the double bond and removing protective groups, to the formation of a compound of formula I wherein $R^2$ and $R^4$ are hydrogen, or b) reacting a carbonyl compound of the formula II

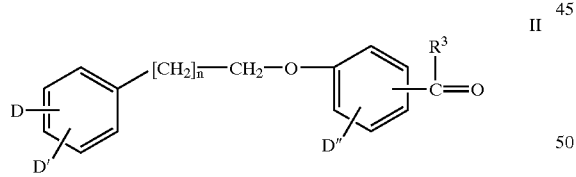

II with a compound of the formula VII

VII in which formulas D, D', D", n, $R^1$ and $R^3$ are as defined in claim 1 and $R^2$ is alkyl, aryl or alkylaryl, followed by dehydroxylation and, if necessary, by removal of protective groups, to the formation of a compound of the formula I, where A is —$CR^3R^4$—$CR^1R^2$—COR, wherein $R^4$ is hydrogen, or c) reacting a compound of the formula VIII

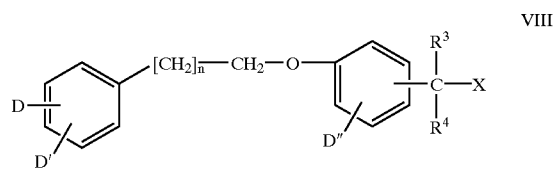

VIII with a compound of the formula VII

VII in which formulas D, D', D", n, R, $R^1$, $R^2$, $R^3$ and $R^4$ are as defined in claim 1 and X is a leaving group, whereafter, if necessary, removing protective groups to the formation of a compound of the formula I wherein A is —$CR^3R^4$—$CR^1R^2$—COR, or d) reacting a compound of the formula V

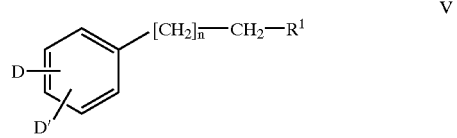

V with a compound of the formula X

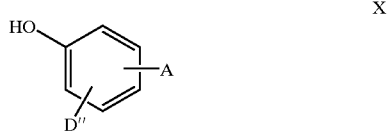

X in which formulas D, D', D", n and A are as defined in claim 1 and $R^1$ is —OH or a leaving group, whereafter, if necessary, removing protective groups, or e) converting a compound of the formula XI

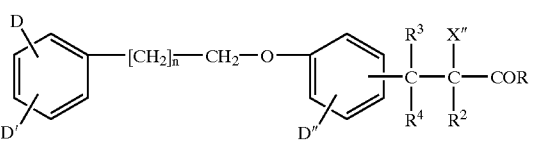

XI in which formula D, D', D", n, R, $R^2$, $R^3$ and $R^4$ are as defined in claim 1 and X" is —OH followed, if necessary, by removal of protective groups, to the formation of a compound of the formula I, wherein A is —$CR^3R^4$—$CR^1R^2$—COR, wherein $R^1$ is —$OR^e$, wherein $R^e$ is as defined in claim 1, —O—$[CH_2]_m$—$OR^f$, wherein m and $R^f$ are as defined in claim 1, —$OCONR^aR^c$, wherein $R^a$ and $R^c$ are as defined in claim 1, or f) reacting a compound of the formula XIII

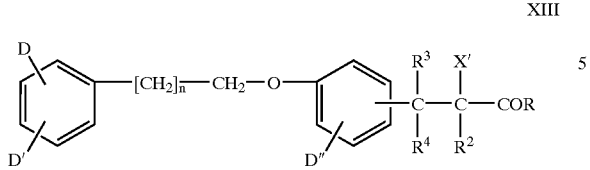

XIII with a thiol, in which formula D, D', D", n, R, $R^2$, $R^3$ and $R^4$ are as defined in claim 1 and X' is halogen, to the formation of a compound of the formula I wherein A is —$CR^3R^4$—$CR^1R^2$—COR, wherein $R^1$ is —$SR^d$, wherein $R^d$ is as defined in claim 1; or g) reacting a compound of the formula XIV

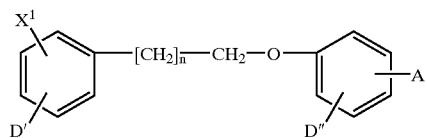

XIV with a suitable reagent and followed by removal of protective groups, in which formula D', D", n and A are as defined in claim 1 and $X^1$ is —OH, —SH or —$NR^cH$ to the formation of a compound of the formula I, wherein D is —$OSO_2R^d$, —$SR^c$, —$OCONR^fR^a$, —$NR^cCOOR^d$, —$NR^cCOR^a$, —$NR^cR^d$, —$NR^cCONR^aR^k$, —$NR^cSO_2R^d$ or —$NR^cCSNR^aR^k$; wherein $R^a$, $R^c$, $R^d$, $R^f$, $R^g$ and $R^k$ are as defined in claim 1, or h) hydrolysis of a compound of the formula I wherein R is —$OR^p$, wherein $R^p$ is a protective group, to the formation of a compound of the formula I wherein R is —OH, or i) reacting a compound of the formula I, wherein R is —OH with a compound of the formula $HNR^aR^b$, wherein $R^a$ and $R^b$ are as defined in claim 1, to the formation of a compound of the formula I wherein R is —$NR^aR^b$, or j) oxidizing a compound of the formula XV

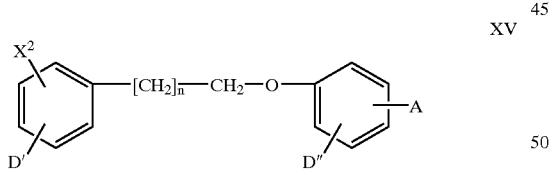

XV and if necessary followed by removal of protective groups, in which formula D', D", n and A are as defined in claim 1 and $X^2$ is —$SOR^d$ or —$SR^d$ wherein $R^d$ is as defined in claim 1, to the formation of a compound of the formula I wherein D is —$SO_2R^d$ or —$SOR^d$; whereafter, if desired, the compound obtained according to any of methods a)–j) is converted to a stereoisomer, a pharmaceutically acceptable salt thereof and/or a solvate thereof.

34. A pharmaceutical formulation comprising a compound according to any one of claims 1, 30, 31 as active ingredient and optionally a substance selected from the group consisting of a pharmaceutically acceptable carrier, adjuvant, diluent and mixtures thereof.

35. A method for the prophylaxis and/or treatment of clinical conditions associated with insulin resistance wherein a therapeutically active amount of a compound according to any one of claims 1, 30 and 31 is administered to a mammal in need of such prophylaxis and/or treatment.

36. A method according to claim 35 wherein the prophylaxis and/or treatment of clinical conditions associated with insulin resistance is the prophylaxis and/or treatment of dyslipidaemia.

37. A method according to claim 36 wherein the prophylaxis and/or treatment of clinical conditions associated with insulin resistance is the prophylaxis and/or treatment of hyperglycaemia in non insulin dependent diabetes mellitus.

38. A pharmaceutical formulation for the prophylaxis and/or treatment of clinical conditions associated with insulin resistance wherein the active ingredient is a compound according to any one of claims 1, 30 and 31.

39. A compound according to claim 4, wherein $R^1$ is —Olower alkyl.

40. A compound according to claim 7, wherein $R^1$ is —Olower alkyl.

41. A compound according to claim 12, wherein $R^1$ is —Olower alkyl.

42. A compound according to claim 15, wherein $R^1$ is —Olower alkyl.

43. A compound according to claim 18, wherein $R^1$ is —Olower alkyl.

44. A compound according to claim 21, wherein $R^1$ is —Olower alkyl.

45. A compound according to claim 24, wherein $R^1$ is —Olower alkyl.

46. A compound according to claim 30, wherein $R^1$ is —Olower alkyl.

47. A compound according to claim 30, wherein $R^1$ is —Olower alkyl.

\* \* \* \* \*

UNITED STATES PATENT AND TRADEMARK OFFICE
CERTIFICATE OF CORRECTION

| | |
|---|---|
| PATENT NO. | : 6,630,600 B1 |
| APPLICATION NO. | : 09/341931 |
| DATED | : October 7, 2003 |
| INVENTOR(S) | : Andersson et al. |

It is certified that error appears in the above-identified patent and that said Letters Patent is hereby corrected as shown below:

Col. 15, lines 41-48
That portion of the formula reading " D' " should read --D"--.

Col. 82, line 25
"a salts" should read --salts--.

Col. 85, line 45
"postion" should read --position--.

Col. 85, line 59
"R" should read --$R^2$--.

Col. 86, line 5
"–NHOalkylaryl," should read -- –NHOalkylaryl or--.

Col. 88, line 57
"pheyl" should read --phenyl--.

Col. 92, line 37
"claim 12" should read --claim 10--.

Col. 92, line 39
"claim 15" should read --claim 12--.

Col. 92, line 42
"claim 18" should read --claim 15--.

Col. 92, line 44
"claim 21" should read --claim 18--.

UNITED STATES PATENT AND TRADEMARK OFFICE
CERTIFICATE OF CORRECTION

PATENT NO. : 6,630,600 B1
APPLICATION NO. : 09/341931
DATED : October 7, 2003
INVENTOR(S) : Andersson et al.

It is certified that error appears in the above-identified patent and that said Letters Patent is hereby corrected as shown below:

Col. 92, line 46
"claim 24" should read --claim 21--.

Col. 92, line 49
"claim 30" should read --claim 24--.

Signed and Sealed this

Fifth Day of February, 2008

JON W. DUDAS
*Director of the United States Patent and Trademark Office*